(12) United States Patent
Carstensen et al.

(10) Patent No.: US 10,808,268 B2
(45) Date of Patent: Oct. 20, 2020

(54) POLYPEPTIDES HAVING ALPHA-GALACTOSIDASE ACTIVITY AND POLYNUCLEOTIDES ENCODING SAME

(71) Applicant: Novozymes A/S, Bagsvaerd (DK)

(72) Inventors: Lone Carstensen, Allerod (DK); Nikolaj Spodsberg, Holte (DK); Morten Gjermansen, Greve (DK); Jesper Salomon, Holte (DK); Kristian B. R. M. Krogh, Holte (DK); Eduardo Antonio Della Pia, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 35 days.

(21) Appl. No.: 16/094,368

(22) PCT Filed: May 24, 2017

(86) PCT No.: PCT/EP2017/062629
§ 371 (c)(1),
(2) Date: Oct. 17, 2018

(87) PCT Pub. No.: WO2017/202966
PCT Pub. Date: Nov. 30, 2017

(65) Prior Publication Data
US 2019/0144902 A1  May 16, 2019

(30) Foreign Application Priority Data
May 24, 2016 (EP) .................................. 16170960

(51) Int. Cl.
| | | |
|---|---|---|
| *C12N 9/40* | (2006.01) | |
| *C12P 19/02* | (2006.01) | |
| *C12P 19/14* | (2006.01) | |
| *A23K 40/10* | (2016.01) | |
| *A23K 10/30* | (2016.01) | |
| *A23K 20/147* | (2016.01) | |
| *A23K 50/75* | (2016.01) | |
| *A23K 50/30* | (2016.01) | |
| *A23K 10/14* | (2016.01) | |
| *A23K 10/16* | (2016.01) | |

(52) U.S. Cl.
CPC .............. *C12P 19/02* (2013.01); *A23K 10/14* (2016.05); *A23K 10/16* (2016.05); *A23K 10/30* (2016.05); *A23K 20/147* (2016.05); *A23K 40/10* (2016.05); *A23K 50/30* (2016.05); *A23K 50/75* (2016.05); *C12N 9/2465* (2013.01); *C12P 19/14* (2013.01); *C12Y 302/01022* (2013.01)

(58) Field of Classification Search
CPC ................................ C12N 9/40; C12N 9/2465
See application file for complete search history.

(56) References Cited

U.S. PATENT DOCUMENTS

| | | | |
|---|---|---|---|
| 6,197,566 B1 | 3/2001 | Knap et al. | |
| 2015/0307562 A1 | 10/2015 | Basu | |
| 2016/0339078 A1 | 11/2016 | Hamil | |

FOREIGN PATENT DOCUMENTS

| | | |
|---|---|---|
| CN | 101457208 A | 6/2009 |
| CN | 104805101 A | 7/2015 |
| EP | 2272964 A2 | 1/2011 |
| EP | 2052078 B1 | 4/2013 |
| WO | 2009/108941 A2 | 9/2009 |

OTHER PUBLICATIONS

Cao et al., Journal of Microbiology and Biotechnology, vol. 19, No. 11, pp. 1295-1300 (2009).
Cao et al., Genbank Accession No. FJ159431 (2011).
Daniell, Geneseq Accession No. AXR38489 (2009).
Dastager et al., ENA Accession No. KSU82091 (2015).
Dastager et al., UniProt Accession No. A0A0V8J599 (2016).
Katrolia et al., Critical Reviews in Biotechnology, vol. 34, No. 4, pp. 307-317 (2014).
Li et al., Letters in Applied Microbiology, vol. 25, No. 1, pp. 1-4 (1997).
Liu et al., UniProt Accession No. A0A0M4FME9 (2015).
Zhu et al., UniProt Accession No. A0A0F7TK13 (2014).
Anonymous, Alignment of the FASTA Sequence of UniProtKB Entry A0A0F7TK13 and SEQ ID No: 3 (2016).

*Primary Examiner* — Tekchand Saidha
(74) *Attorney, Agent, or Firm* — Elias Lambiris

(57) ABSTRACT

The present invention relates to methods of releasing galactose from legumes using polypeptides having alpha-galactosidase activity. The invention also relates to polypeptides having alpha-galactosidase activity, polynucleotides encoding the polypeptides, nucleic acid constructs, vectors, and host cells comprising the polynucleotides as well as methods of 5 producing the polypeptides. The invention also relates to compositions comprising the polypeptides of the invention and the use of the polypeptides in animal feed.

8 Claims, No Drawings

Specification includes a Sequence Listing.

POLYPEPTIDES HAVING ALPHA-GALACTOSIDASE ACTIVITY AND POLYNUCLEOTIDES ENCODING SAME

CROSS-REFERENCE TO RELATED APPLICATIONS

This application is a 35 U.S.C. 371 national application of international application no. PCT/EP2017/062629 filed May 24, 2017, which claims priority or the benefit under 35 U.S.C. 119 of European application no. 16170960.5 filed May 24, 2016, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to methods of releasing galactose from legumes using polypeptides having alpha-galactosidase activity. The invention also relates to polypeptides having alpha-galactosidase activity, polynucleotides encoding the polypeptides, nucleic acid constructs, vectors, and host cells comprising the polynucleotides as well as methods of producing the polypeptides. The invention also relates to compositions comprising the polypeptides of the invention and the use of the polypeptides in animal feed.

Description of the Related Art

Alpha-galactosidase is a glycoside hydrolase enzyme that hydrolyses the terminal alpha-galactosyl moieties from glycolipids and glycoproteins that is present in, e.g. legumes, vegetables, grains, cereals and the like. Alpha-galactosidases are produced by various microorganisms, plants and animals, but mammals are deficient in intestinal alpha-galactosidase production and consequently are incapable of decomposing ingested alpha-galactosides by themselves. Instead, ingested alpha-galactosides are decomposed by microorganisms present in the intestine.

Soybean is a species of legume native to East Asia and is the second biggest feed crop globally and the biggest protein source applied in animal feed. Soybean can be manufactured (defatted) to produce soybean meal (SBM), and SBM is a significant and cheap source of high quality protein for animal feeds. Other common types of legume are chickpea, lupin, lentil, peanut, beans or peas which can also be processed and used as animal feed. Legumes, such as soybean, contain significant amounts of raffinose oligosaccharides which requires an alpha-galactosidase present to release galactose.

Up to 70% of a farmer's expenses is from the cost of animal feed. Thus, there is always an interest by farmers in either reducing feed costs by feeding less, or in obtaining improved animal growth using the same amount of feed. One way of achieving this is to release as much energy from the feed as possible by e.g. using enzymes such as alpha-galactosidases. However, enzymes are also an expense and therefore the alpha-galactosidase should work at a cost-effective dose.

GH36 alpha-galactosidase are known in the prior art, such as disclosed in WO2009/108941 (SEQ ID NO: 597, AXR38459). However, as shown in Example 13, a close analogue of this prior art alpha-galactosidase is not very effective at releasing galactose from soybean meal. Thus, the object of this invention is to provide alpha-galactosidases which are more effective at releasing galactose from legumes than known alpha-galactosidases.

SUMMARY OF THE INVENTION

The present invention relates to a method of releasing galactose from plant based material, comprising treating the plant based material with one or more GH36 polypeptides having alpha-galactosidase activity, wherein the GH36 polypeptide having alpha-galactosidase activity is selected from the group consisting of:

(a) a polypeptide having at least 80% sequence identity to the polypeptide of SEQ ID NO: 2, SEQ ID NO: 5, SEQ ID NO: 8, SEQ ID NO: 12, SEQ ID NO: 14 and SEQ ID NO: 19;

(b) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1 to 50 positions;

(c) a polypeptide comprising the polypeptide of (a) or (b) and a N-terminal and/or C-terminal His-tag and/or HQ-tag;

(d) a polypeptide comprising the polypeptide of (a) or (b) and a N-terminal and/or C-terminal extension of up to 10 amino acids; and (e) a fragment of the polypeptide of (a) or (b) having alpha-galactosidase activity and having at least 90% of the length of the mature polypeptide.

The invention also relates to isolated polypeptide having alpha-galactosidase activity as defined in the claims, polynucleotides encoding the polypeptides of the present invention; nucleic acid constructs; expression vectors; recombinant host cells comprising the polynucleotides and methods of producing the polypeptides. The invention further relates to compositions, such as granules, liquid formulations, animal feed or animal feed additives, comprising the polypeptide of the invention and uses thereof; methods of improving the performance of an animal; methods of preparing an animal feed and methods for improving the nutritional value of an animal feed;

Overview of Sequence Listing

SEQ ID NO: 1 is the gene sequence of GH36 alpha-galactosidase as isolated from *Bacillus deramificans*.

SEQ ID NO: 2 is the amino acid sequence as deduced from SEQ ID NO: 1.

SEQ ID NO: 3 is the amino acid sequence of SEQ ID NO: 2 with His-tag.

SEQ ID NO: 4 is the gene sequence of GH36 alpha-galactosidase as isolated from *Bacillus acidopullulyticus*.

SEQ ID NO: 5 is the amino acid sequence as deduced from SEQ ID NO: 4.

SEQ ID NO: 6 is the amino acid sequence of SEQ ID NO: 5 with His-tag.

SEQ ID NO: 7 is the gene sequence of GH36 alpha-galactosidase as isolated from *Anoxybacillus bogrovensis*.

SEQ ID NO: 8 is the amino acid sequence as deduced from SEQ ID NO: 7.

SEQ ID NO: 9 is the amino acid sequence of SEQ ID NO: 8 with His-tag.

SEQ ID NO: 10 is the gene sequence of GH36 alpha-galactosidase as isolated from *Aspergillus sydowii*.

SEQ ID NO: 11 is the amino acid sequence as deduced from SEQ ID NO: 10.

SEQ ID NO: 12 is the amino acid sequence of the mature GH36 alpha-galactosidase from *Aspergillus sydowii*.

SEQ ID NO: 13 is the cDNA sequence of GH36 alpha-galactosidase as isolated from *Bacillus* sp-19140.

SEQ ID NO: 14 is the amino acid sequence as deduced from SEQ ID NO: 10.

SEQ ID NO: 15 is the amino acid sequence of SEQ ID NO: 14 with His-tag.

SEQ ID NO: 16 is the corrected amino acid sequence of the alpha-galactosidase as disclosed in WO1994/23022.

SEQ ID NO: 17 is the cDNA sequence of GH36 alpha-galactosidase as isolated from *Aspergillus puniceus*.

SEQ ID NO: 18 is the amino acid sequence as deduced from SEQ ID NO: 17.

SEQ ID NO: 19 is the amino acid sequence of the mature GH36 alpha-galactosidase from *Aspergillus puniceus*.

SEQ ID NO: 20 is the amino acid sequence of a mature GH36 alpha-galactosidase from *Parageobacillus thermoglucosidans*.

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-galactosidase: The term "alpha-galactosidase", also called α-D-galactoside galactohydrolase (E.C. 3.2.1.22), means an enzyme that catalyses the hydrolysis of terminal, non-reducing α-D-galactose residues in α-D-galactosides, such as galactose oligosaccharides, galactomannans and galactolipids. Alpha-galactosidase activity can be determined using 4-nitrophenyl α-D-galactopyranoside (available from Megazyme International, Bray, Co. Wicklow, Ireland) as substrate in 100 mM MES (Sigma) buffer pH 7.0±0.05 at room temperature. The enzyme is diluted in 2-fold dilutions and then the 4-nitrophenyl α-D-galactopyranoside substrate is dissolved in the solution containing the enzyme. The alpha-galactosidase activity is followed directly in the buffer by measuring the absorbance of released pNP at 405 nm as function of time. A detailed assay can be found in the alpha-galactosidase assay as described herein. In one aspect, the polypeptides of the present invention have at least 60%, such as at least 70%, at least 75%, at least 80%, at least 85%, at least 90%, at least 95% or at least 100% of the alpha-galactosidase activity of the polypeptide of SEQ ID NO: 12.

Animal: The term "animal" refers to all animals except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

Animal feed: The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio: The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Fragment: The term "fragment" means a polypeptide having one or more (e.g., several) amino acids absent from the amino and/or carboxyl terminus of a mature polypeptide or domain; wherein the fragment has alpha-galactosidase activity.

In one aspect, the fragment comprises at least 90% of the length of the mature polypeptide, such as at least 655 amino acids of SEQ ID NO: 2, at least 660 amino acids of SEQ ID NO: 3, at least 657 amino acids of SEQ ID NO: 5, at least 663 amino acids of SEQ ID NO: 6, at least 658 amino acids of SEQ ID NO: 8, at least 664 amino acids of SEQ ID NO: 9, at least 647 amino acids of SEQ ID NO: 11, at least 647 amino acids of SEQ ID NO: 12, at least 657 amino acids of SEQ ID NO: 14, at least 663 amino acids of SEQ ID NO: 15, at least 661 amino acids of SEQ ID NO: 18, or at least 661 amino acids of SEQ ID NO: 19.

In one aspect, the fragment comprises at least 92% of the length of the mature polypeptide, such as at least 669 amino acids of SEQ ID NO: 2, at least 675 amino acids of SEQ ID NO: 3, at least 672 amino acids of SEQ ID NO: 5, at least 678 amino acids of SEQ ID NO: 6, at least 673 amino acids of SEQ ID NO: 8, at least 678 amino acids of SEQ ID NO: 9, at least 661 amino acids of SEQ ID NO: 11, at least 661 amino acids of SEQ ID NO: 12, at least 672 amino acids of SEQ ID NO: 14, at least 678 amino acids of SEQ ID NO: 15, at least 676 amino acids of SEQ ID NO: 18, or at least 676 amino acids of SEQ ID NO: 19.

In one aspect, the fragment comprises at least 94% of the length of the mature polypeptide, such as at least 684 amino acids of SEQ ID NO: 2, at least 689 amino acids of SEQ ID NO: 3, at least 687 amino acids of SEQ ID NO: 5, at least 692 amino acids of SEQ ID NO: 6, at least 688 amino acids of SEQ ID NO: 8, at least 693 amino acids of SEQ ID NO: 9, at least 675 amino acids of SEQ ID NO: 11, at least 675 amino acids of SEQ ID NO: 12, at least 687 amino acids of SEQ ID NO: 14, at least 692 amino acids of SEQ ID NO: 15, at least 690 amino acids of SEQ ID NO: 18, or at least 690 amino acids of SEQ ID NO: 19.

In one aspect, the fragment comprises at least 96% of the length of the mature polypeptide, such as at least 698 amino acids of SEQ ID NO: 2, at least 704 amino acids of SEQ ID NO: 3, at least 701 amino acids of SEQ ID NO: 5, at least 707 amino acids of SEQ ID NO: 6, at least 702 amino acids of SEQ ID NO: 8, at least 708 amino acids of SEQ ID NO: 9, at least 690 amino acids of SEQ ID NO: 11, at least 690 amino acids of SEQ ID NO: 12, at least 701 amino acids of SEQ ID NO: 14, at least 707 amino acids of SEQ ID NO: 15, at least 705 amino acids of SEQ ID NO: 18, or at least 705 amino acids of SEQ ID NO: 19.

In one aspect, the fragment comprises at least 98% of the length of the mature polypeptide, such as at least 713 amino acids of SEQ ID NO: 2, at least 719 amino acids of SEQ ID NO: 3, at least 716 amino acids of SEQ ID NO: 5, at least 722 amino acids of SEQ ID NO: 6, at least 717 amino acids of SEQ ID NO: 8, at least 723 amino acids of SEQ ID NO: 9, at least 704 amino acids of SEQ ID NO: 11, at least 704 amino acids of SEQ ID NO: 12, at least 716 amino acids of SEQ ID NO: 14, at least 722 amino acids of SEQ ID NO: 15, at least 720 amino acids of SEQ ID NO: 18, or at least 720 amino acids of SEQ ID NO: 19.

In one aspect, the fragment comprises at least 99% of the length of the mature polypeptide, such as at least 720 amino acids of SEQ ID NO: 2, at least 726 amino acids of SEQ ID NO: 3, at least 723 amino acids of SEQ ID NO: 5, at least 729 amino acids of SEQ ID NO: 6, at least 724 amino acids of SEQ ID NO: 8, at least 730 amino acids of SEQ ID NO: 9, at least 711 amino acids of SEQ ID NO: 11, at least 711 amino acids of SEQ ID NO: 12, at least 723 amino acids of SEQ ID NO: 14, at least 729 amino acids of SEQ ID NO: 15, at least 727 amino acids of SEQ ID NO: 18, or at least 727 amino acids of SEQ ID NO: 19.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 728 of SEQ ID NO: 2. In another aspect, the mature polypeptide is amino acids 1 to 734 of SEQ ID NO: 3. In one aspect, the mature polypeptide is amino acids 1 to 731 of SEQ ID NO: 5. In another aspect, the mature polypeptide is amino acids 1 to 737 of SEQ ID NO: 6. In one aspect, the mature polypeptide is amino acids 1 to 732 of SEQ ID NO: 8. In another aspect, the mature polypeptide is amino acids 1 to 738 of SEQ ID NO: 9. In one aspect, the mature polypeptide is amino acids 1 to 719 of SEQ ID NO: 11. In another aspect, the mature polypeptide is amino acids 1 to 719 of SEQ ID NO: 12. In one aspect, the mature polypeptide is amino acids 1 to 731 of SEQ ID NO: 14. In another aspect, the mature polypeptide is amino acids 1 to 737 of SEQ ID NO: 15. In one aspect, the mature polypeptide is amino acids 1 to 735 of SEQ ID NO: 18 and amino acids −29 to −1 of SEQ ID NO: 18 are a signal peptide. In another aspect, the mature polypeptide is amino acids 1 to 735 of SEQ ID NO: 19.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having alpha-galactosidase activity. In one aspect, the mature polypeptide coding sequence is nucleotides 1 to 2184 of SEQ ID NO: 1. In one aspect, the mature polypeptide coding sequence is nucleotides 1 to 2193 of SEQ ID NO: 4. In one aspect, the mature polypeptide coding sequence is nucleotides 1 to 2196 of SEQ ID NO: 7. In one aspect, the mature polypeptide coding sequence is the joined sequence of nucleotides 1 to 85, nucleotides 131 to 734 and nucleotides 787 to 2323 of SEQ ID NO: 10. In one aspect, the mature polypeptide coding sequence is nucleotides 1 to 2193 of SEQ ID NO: 13. In one aspect, the mature polypeptide coding sequence is the joined sequence of nucleotides 1 to 109, nucleotides 173 to 779 and nucleotides 864 to 2439 of SEQ ID NO: 17.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Nutrient Digestibility: The term "nutrient digestibility" means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Operably linked: The term "operably linked" means a configuration in which a control sequence is placed at an appropriate position relative to the coding sequence of a polynucleotide such that the control sequence directs expression of the coding sequence.

Release×g galactose per kg soybean meal: The term "release×g galactose per kg soybean meal" means the amount of galactose in grams which is released into the supernatant after soybean meal has been incubation with an enzyme. For the purpose of the present invention, the release of galactose per kg soybean meal may be determined when performed under the reaction conditions 20 mg polypeptide per kg soybean meal in 10% w/v 0.1M citric acid-phosphate buffer pH 6.5 incubating at 40° C. for 2 hours as described in the Galactose SBM Assay herein.

In a more detailed embodiment, a 10 w/v % slurry of soybean meal is prepared from soybean meal milled to a 0.5 mm particle size and 0.1 M citric acid-phosphate buffer, pH 6.5±0.05. The incubation vessels with the 10 w/v % slurry of soybean meal is heated to a stable temperature of 40±2° C. while stirring. When a stable temperature had been achieved, the six D-(+)-galactose standards are added to the incubation vessels to in-vessel concentrations of 5, 2.5, 1.25, 0.625, 0.313 and 0.157 mg galactose per mL incubation volume. Each standard is incubated in duplicates. The diluted enzymes are then added to their respective incubation vessels in the volumes required to reach their desired concentrations (in mg EP/kg soybean meal). Each enzyme treatment is incubated in triplicates. Additionally, two times three incubation vessels are included without standards or enzyme treatments as blank treatments to obtain the baseline galactose concentration in the soybean meal slurry. The incubation vessels are incubated at 40±2° C., while stirring for 2 hours. After incubation the vessels are centrifuged at 1500 g at 5° C. for 15 minutes. The supernatants are then analyzed in an assay based on the Raffinose/Galactose kit from Megazyme (product name K-RAFGA) and the concentration of galactose is then calculated as described in the Galactose SBM Assay herein.

In an embodiment, the GH36 polypeptide having alpha-galactosidase of the invention releases at least 19 g, such as at least 19.5 g, at least 20 g, at least 20.5 g, at least 21 g, at least 21.5 g, at least 22 g or at least 23 g galactose per kg soybean meal.

Plant based material: The term "plant based material" means that the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Sequence identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the -nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labelled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having alpha-galactosidase activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having alpha-galactosidase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. In one aspect, the variants of the present invention releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In another aspect, the variants of the present invention have at least 60%, such as at least 70%, at least 75%, at least 80%, at least 85%, at least 90%, at least 95% or at least 100% of the alpha-galactosidase activity of the polypeptide of SEQ ID NO: 12 when using the alpha-galactosidase assay as described herein.

DETAILED DESCRIPTION OF THE INVENTION

The inventors have found that certain alpha-galactosidases from glycoside hydrolase family 36 (herein referred to as GH36) are surprisingly good at degrading the raffinose family of oligosaccharides (RFOs), such as the trisaccharide raffinose, the tetrasaccharide stachyose, and the pentasaccharide verbascose. These RFOs are typically found in plants from the taxonomic subclass rosids specifically the subfamily Papilionoideae, such as soy beans, chickpea, beans, lupin, lentil, peanut and peas or the tribe Brassiceae, such as canola or rapeseed.

The degradation of RFO's can be measured as the amount of galactose released into the supernatant when e.g. soybean meal is treated with an alpha-galactosidase. Increased amounts of solubilisation will result in more galactose being released which can be detected using e.g. the Galactose SBM Assay method as described herein.

Methods of Releasing Galactose

Thus the invention relates to a method of releasing galactose from plant based material, comprising treating the plant based material with one or more GH36 polypeptides having alpha-galactosidase activity, wherein the GH36 polypeptide having alpha-galactosidase activity is selected from the group consisting of:

(a) a polypeptide having at least 80% sequence identity to the polypeptide of SEQ ID NO: 2;
(b) a polypeptide having at least 80% sequence identity to the polypeptide of SEQ ID NO: 5;
(c) a polypeptide having at least 80% sequence identity to the polypeptide of SEQ ID NO: 8;
(d) a polypeptide having at least 80% sequence identity to the polypeptide of SEQ ID NO: 12;
(e) a polypeptide having at least 80% sequence identity to the polypeptide of SEQ ID NO: 14;
(f) a polypeptide having at least 80% sequence identity to the polypeptide of SEQ ID NO: 19;
(g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(h) a polypeptide comprising the polypeptide of (a), (b), (c), (d), (e), (f) or (g) and a N-terminal and/or C-terminal His-tag and/or HQ-tag;
(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and
(j) a fragment of the polypeptide of (a), (b), (c), (d), (e), (f) or (g) having alpha-galactosidase activity and having at least 90% of the length of the mature polypeptide.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In an embodiment, the GH36 polypeptide having alpha-galactosidase is obtained or obtainable from the taxonomic order Bacillales, preferably the family Bacillaceae, more preferably the genus *Bacillus*. In an embodiment, the GH36 polypeptide having alpha-galactosidase is obtained or obtainable from the taxonomic order Bacillales, preferably the family Bacillaceae and is selected from the group selected from SEQ ID NO: 2, SEQ ID NO: 5, SEQ ID NO:8 and SEQ ID NO: 14.

In an embodiment, the GH36 polypeptide having alpha-galactosidase is obtained or obtainable from the taxonomic order Eurotiales, preferably the family Aspergillaceae, more preferably the genus *Aspergillus*. In an embodiment, the GH36 polypeptide having alpha-galactosidase is obtained or obtainable from the taxonomic order Eurotiales, preferably the family Aspergillaceae, more preferably the genus *Aspergillus* and is selected from the group selected from SEQ ID NO: 12 and SEQ ID NO: 19.

In an embodiment, the GH36 polypeptide having alpha-galactosidase releases at least 19 g, such as at least 19.5 g, at least 20 g, at least 20.5 g, at least 21 g, at least 21.5 g, at least 22 g or at least 23 g galactose per kg soybean meal. In an embodiment, the GH36 polypeptide having alpha-galactosidase releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a preferred embodiment, the invention relates to a method of releasing galactose from plant based material, comprising treating the plant based material with one or more GH36 polypeptides having alpha-galactosidase activity, wherein the GH36 polypeptide having alpha-galactosidase activity is selected from the group consisting of:

(a) a polypeptide having at least 85% sequence identity to the polypeptide of SEQ ID NO: 2;
(b) a polypeptide having at least 85% sequence identity to the polypeptide of SEQ ID NO: 5;
(c) a polypeptide having at least 85% sequence identity to the polypeptide of SEQ ID NO: 8;
(d) a polypeptide having at least 85% sequence identity to the polypeptide of SEQ ID NO: 12;
(e) a polypeptide having at least 85% sequence identity to the polypeptide of SEQ ID NO: 14;
(f) a polypeptide having at least 85% sequence identity to the polypeptide of SEQ ID NO: 19;
(g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(h) a polypeptide comprising the polypeptide of (a), (b), (c), (d), (e), (f) or (g) and a N-terminal and/or C-terminal His-tag and/or HQ-tag;
(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and
(j) a fragment of the polypeptide of (a), (b), (c), (d), (e), (f) or (g) having alpha-galactosidase activity and having at least 90% of the length of the mature polypeptide.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In an embodiment, the GH36 polypeptide having alpha-galactosidase is obtained or obtainable from the taxonomic order Bacillales, preferably the family Bacillaceae, more preferably the genus *Bacillus*. In an embodiment, the GH36 polypeptide having alpha-galactosidase is obtained or obtainable from the taxonomic order Bacillales, preferably the family Bacillaceae and is selected from the group selected from SEQ ID NO: 2, SEQ ID NO: 5, SEQ ID NO:8 and SEQ ID NO: 14.

In an embodiment, the GH36 polypeptide having alpha-galactosidase is obtained or obtainable from the taxonomic order Eurotiales, preferably the family Aspergillaceae, more preferably the genus *Aspergillus*. In an embodiment, the GH36 polypeptide having alpha-galactosidase is obtained or obtainable from the taxonomic order Eurotiales, preferably the family Aspergillaceae, more preferably the genus *Aspergillus* and is selected from the group selected from SEQ ID NO: 12 and SEQ ID NO: 19.

In an embodiment, the GH36 polypeptide having alpha-galactosidase releases at least 19 g, such as at least 19.5 g, at least 20 g, at least 20.5 g, at least 21 g, at least 21.5 g, at least 22 g or at least 23 g galactose per kg soybean meal. In an embodiment, the GH36 polypeptide having alpha-galactosidase releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a more preferred embodiment, the invention relates to a method of releasing galactose from plant based material, comprising treating the plant based material with one or more GH36 polypeptides having alpha-galactosidase activity, wherein the GH36 polypeptide having alpha-galactosidase activity is selected from the group consisting of:
 (a) a polypeptide having at least 90% sequence identity to the polypeptide of SEQ ID NO: 2;
 (b) a polypeptide having at least 90% sequence identity to the polypeptide of SEQ ID NO: 5;
 (c) a polypeptide having at least 90% sequence identity to the polypeptide of SEQ ID NO: 8;
 (d) a polypeptide having at least 90% sequence identity to the polypeptide of SEQ ID NO: 12;
 (e) a polypeptide having at least 90% sequence identity to the polypeptide of SEQ ID NO: 14;
 (f) a polypeptide having at least 90% sequence identity to the polypeptide of SEQ ID NO: 19;
 (g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (h) a polypeptide comprising the polypeptide of (a), (b), (c), (d), (e), (f) or (g) and a N-terminal and/or C-terminal His-tag and/or HQ-tag;
 (i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and
 (j) a fragment of the polypeptide of (a), (b), (c), (d), (e), (f) or (g) having alpha-galactosidase activity and having at least 90% of the length of the mature polypeptide.

In an embodiment, the plant based material is from the the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In an embodiment, the GH36 polypeptide having alpha-galactosidase is obtained or obtainable from the taxonomic order Bacillales, preferably the family Bacillaceae, more preferably the genus *Bacillus*. In an embodiment, the GH36 polypeptide having alpha-galactosidase is obtained or obtainable from the taxonomic order Bacillales, preferably the family Bacillaceae and is selected from the group selected from SEQ ID NO: 2, SEQ ID NO: 5, SEQ ID NO:8 and SEQ ID NO: 14.

In an embodiment, the GH36 polypeptide having alpha-galactosidase is obtained or obtainable from the taxonomic order Eurotiales, preferably the family Aspergillaceae, more preferably the genus *Aspergillus*. In an embodiment, the GH36 polypeptide having alpha-galactosidase is obtained or obtainable from the taxonomic order Eurotiales, preferably the family Aspergillaceae, more preferably the genus *Aspergillus* and is selected from the group selected from SEQ ID NO: 12 and SEQ ID NO: 19.

In an embodiment, the GH36 polypeptide having alpha-galactosidase releases at least 19 g, such as at least 19.5 g, at least 20 g, at least 20.5 g, at least 21 g, at least 21.5 g, at least 22 g or at least 23 g galactose per kg soybean meal. In an embodiment, the GH36 polypeptide having alpha-galactosidase releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a more preferred embodiment, the invention relates to a method of releasing galactose from plant based material, comprising treating the plant based material with one or more GH36 polypeptides having alpha-galactosidase activity, wherein the GH36 polypeptide having alpha-galactosidase activity is selected from the group consisting of:
 (a) a polypeptide having at least 95% sequence identity to the polypeptide of SEQ ID NO: 2;
 (b) a polypeptide having at least 95% sequence identity to the polypeptide of SEQ ID NO: 5;
 (c) a polypeptide having at least 95% sequence identity to the polypeptide of SEQ ID NO: 8;
 (d) a polypeptide having at least 95% sequence identity to the polypeptide of SEQ ID NO: 12;
 (e) a polypeptide having at least 95% sequence identity to the polypeptide of SEQ ID NO: 14;
 (f) a polypeptide having at least 95% sequence identity to the polypeptide of SEQ ID NO: 19;
 (g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 positions;

(h) a polypeptide comprising the polypeptide of (a), (b), (c), (d), (e), (f) or (g) and a N-terminal and/or C-terminal His-tag and/or HQ-tag;

(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and (j) a fragment of the polypeptide of (a), (b), (c), (d), (e), (f) or (g) having alpha-galactosidase activity and having at least 90% of the length of the mature polypeptide.

In an embodiment, the GH36 polypeptide comprises or consists of amino acids 1 to 728 of SEQ ID NO: 2, amino acids 1 to 734 of SEQ ID NO: 3, amino acids 1 to 731 of SEQ ID NO: 5, amino acids 1 to 737 of SEQ ID NO: 6, amino acids 1 to 732 of SEQ ID NO: 8, amino acids 1 to 738 of SEQ ID NO: 9, amino acids 1 to 719 of SEQ ID NO: 11, amino acids 1 to 719 of SEQ ID NO: 12, amino acids 1 to 731 of SEQ ID NO: 14 and/or amino acids 1 to 737 of SEQ ID NO: 15.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In an embodiment, the GH36 polypeptide having alpha-galactosidase is obtained or obtainable from the taxonomic order Bacillales, preferably the family Bacillaceae, more preferably the genus *Bacillus*. In an embodiment, the GH36 polypeptide having alpha-galactosidase is obtained or obtainable from the taxonomic order Bacillales, preferably the family Bacillaceae and is selected from the group selected from SEQ ID NO: 2, SEQ ID NO: 5, SEQ ID NO:8 and SEQ ID NO: 14.

In an embodiment, the GH36 polypeptide having alpha-galactosidase is obtained or obtainable from the taxonomic order Eurotiales, preferably the family Aspergillaceae, more preferably the genus *Aspergillus*. In an embodiment, the GH36 polypeptide having alpha-galactosidase is obtained or obtainable from the taxonomic order Eurotiales, preferably the family Aspergillaceae, more preferably the genus *Aspergillus* and is selected from the group selected from SEQ ID NO: 12 and SEQ ID NO: 19.

In an embodiment, the GH36 polypeptide having alpha-galactosidase releases at least 19 g, such as at least 19.5 g, at least 20 g, at least 20.5 g, at least 21 g, at least 21.5 g, at least 22 g or at least 23 g galactose per kg soybean meal. In an embodiment, the GH36 polypeptide having alpha-galactosidase releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

Polypeptides Having Alpha-Galactosidase Activity

In a second aspect the invention relates to polypeptides having alpha-galactosidase activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 2.

In a continuation of the second aspect, the invention relates to polypeptides having alpha-galactosidase activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 3.

In one embodiment, the polypeptide preferably comprises or consists of the amino acid sequence of SEQ ID NO: 2 or an allelic variant thereof; comprises the amino acid sequence of SEQ ID NO: 2 and a N-terminal and/or C-terminal His-tag and/or HQ-tag such as SEQ ID NO: 3; or is a fragment thereof having alpha-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 2. In another embodiment, the polypeptide comprises or consists of amino acids 1 to 728 of SEQ ID NO: 2. In another embodiment, the polypeptide comprises or consists of the mature polypeptide of SEQ ID NO: 3. In another embodiment, the polypeptide comprises or consists of amino acids 1 to 734 of SEQ ID NO: 3. In an embodiment, the polypeptide has been isolated.

In a continuation of the second aspect, the invention relates to a polypeptide having alpha-galactosidase activity encoded by a polynucleotide having a sequence identity to the mature polypeptide coding sequence of SEQ ID NO: 1 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the second aspect, the polypeptide releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a continuation of the second aspect, the invention relates to variants of SEQ ID NO: 2 having alpha-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 2 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 2 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 2 is not more than 10, e.g., 1, 2, 3, 4, 5, 6, 7, 8, 9 or 10. In another embodiment, the number of substitutions and/or deletions and/or insertions in SEQ ID NO: 2 is not more than 10, e.g., 1, 2, 3, 4, 5, 6, 7, 8, 9 or 10. In a further embodiment, the number of substitutions in SEQ ID NO: 2 is not more than 10, e.g., 1, 2, 3, 4, 5, 6, 7, 8, 9 or 10. In a further embodiment, the number of conservative substitutions in SEQ ID NO: 2 is not more than 10, e.g., 1, 2, 3, 4, 5, 6, 7, 8, 9 or 10.

In an embodiment of the second aspect, the variant releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuNal, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-galactosidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Gouet et al defined the catalytic amino acids for the GH36 alpha-galactosidase AgaA (Uniprot Q9ALJ4) from *Geobacillus stearothermophilus* (J. Biol. Chem., 2012, 287(47), 39642-39652) as Asp478 and Asp548. Using an alignment program, the alpha-galactosidases of the invention can be aligned to AgaA and the catalytic amino acids determined, as shown below. In one embodiment, no alteration is made to the catalytic amino acids.

| Sequence | Amino Acid number for AgaA | | | | | | | | | | | | Number of catalytic amino acid |
| --- | --- | --- | --- | --- | --- | --- | --- | --- | --- | --- | --- | --- | --- |
| | 472 | 473 | 474 | 475 | 476 | 477 | 478 | 479 | 480 | 481 | 482 | 483 | |
| AgaA | I | T | Y | V | K | W | D | M | N | R | H | M | 478 |
| SEQ ID NO: 2 | I | S | Y | V | K | W | D | M | N | R | H | M | 478 |
| SEQ ID NO: 5 | I | S | Y | V | K | W | D | M | N | R | H | M | 478 |
| SEQ ID NO: 8 | I | S | Y | V | K | W | D | M | N | R | H | M | 478 |
| SEQ ID NO: 12 | I | S | Y | I | K | W | D | N | N | R | G | M | 480 |
| SEQ ID NO: 14 | I | S | Y | V | K | W | D | M | N | R | H | M | 478 |
| SEQ ID NO: 19 | I | T | Y | I | K | W | D | N | N | R | G | M | 491 |

-continued

| Sequence | Amino Acid number for AgaA | | | | | | | | | | | | Number of catalytic amino acid |
|---|---|---|---|---|---|---|---|---|---|---|---|---|---|
| | 542 | 543 | 544 | 545 | 546 | 547 | 548 | 549 | 550 | 551 | 552 | 553 | |
| AgaA | P | Q | T | W | T | S | D | N | T | D | A | V | 548 |
| SEQ ID NO: 2 | P | Q | V | W | T | S | D | N | T | D | A | I | 548 |
| SEQ ID NO: 5 | P | Q | T | W | T | S | D | N | T | D | A | V | 548 |
| SEQ ID NO: 8 | P | Q | T | W | T | S | D | N | T | D | A | I | 548 |
| SEQ ID NO: 12 | P | Q | I | W | T | S | D | N | T | D | G | V | 542 |
| SEQ ID NO: 14 | P | Q | T | W | T | S | D | N | T | D | A | V | 548 |
| SEQ ID NO: 19 | P | Q | I | W | T | S | D | N | T | D | G | V | 553 |

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In a third aspect, the invention relates to polypeptides having alpha-galactosidase activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 5. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 5.

In a continuation of the third aspect, the invention relates to polypeptides having alpha-galactosidase activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 6.

In one embodiment, the polypeptide preferably comprises or consists of the amino acid sequence of SEQ ID NO: 5 or an allelic variant thereof; comprises the amino acid sequence of SEQ ID NO: 5 and a N-terminal and/or C-terminal His-tag and/or HQ-tag such as SEQ ID NO: 6; or is a fragment thereof having alpha-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 5. In another embodiment, the polypeptide comprises or consists of amino acids 1 to 731 of SEQ ID NO: 5. In another embodiment, the polypeptide comprises or consists of the mature polypeptide of SEQ ID NO: 6. In another embodiment, the polypeptide comprises or consists of amino acids 1 to 737 of SEQ ID NO: 6. In an embodiment, the polypeptide has been isolated.

In a continuation of the third aspect, the invention relates to a polypeptide having alpha-galactosidase activity encoded by a polynucleotide having a sequence identity to the mature polypeptide coding sequence of SEQ ID NO: 4 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the third aspect, the polypeptide releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a continuation of the third aspect, the invention relates to variants of SEQ ID NO: 5 having alpha-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 5 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 5 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 5 is not more than 10, e.g., 1, 2, 3, 4, 5, 6, 7, 8, 9 or 10. In another embodiment, the number of substitutions and/or deletions and/or insertions in SEQ ID NO: 5 is not more than 10, e.g., 1, 2, 3, 4, 5, 6, 7, 8, 9 or 10. In a further embodiment, the number of substitutions in SEQ ID NO: 5 is not more than 10, e.g., 1, 2, 3, 4, 5, 6, 7, 8, 9 or 10. In a further embodiment, the number of conservative substitutions in SEQ ID NO: 5 is not more than 10, e.g., 1, 2, 3, 4, 5, 6, 7, 8, 9 or 10. Examples of amino acid changes, conservative substitutions and fusion peptides are described in the second aspect herein.

In an embodiment of the third aspect, the variant releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a fourth aspect, the invention relates to polypeptides having alpha-galactosidase activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 8.

In a continuation of the fourth aspect, the invention relates to polypeptides having alpha-galactosidase activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 9. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 9.

In one embodiment, the polypeptide preferably comprises or consists of the amino acid sequence of SEQ ID NO: 8 or an allelic variant thereof; comprises the amino acid sequence of SEQ ID NO: 8 and a N-terminal and/or C-terminal His-tag and/or HQ-tag such as SEQ ID NO: 9; or is a fragment thereof having alpha-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 8. In another embodiment, the polypeptide comprises or consists of amino acids 1 to 731 of SEQ ID NO: 8. In another embodiment, the polypeptide comprises or consists of the mature polypeptide of SEQ ID NO: 9. In another embodiment, the polypeptide comprises or consists of amino acids 1 to 737 of SEQ ID NO: 9. In an embodiment, the polypeptide has been isolated.

In a continuation of the fourth aspect, the invention relates to a polypeptide having alpha-galactosidase activity encoded by a polynucleotide having a sequence identity to the mature polypeptide coding sequence of SEQ ID NO: 7 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fourth aspect, the polypeptide releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a continuation of the fourth aspect, the invention relates to variants of SEQ ID NO: 8 having alpha-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 8 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 8 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 8 is not more than 10, e.g., 1, 2, 3, 4, 5, 6, 7, 8, 9 or 10. In another embodiment, the number of substitutions and/or deletions and/or insertions in SEQ ID NO: 8 is not more than 10, e.g., 1, 2, 3, 4, 5, 6, 7, 8, 9 or 10. In a further embodiment, the number of substitutions in SEQ ID NO: 8 is not more than 10, e.g., 1, 2, 3, 4, 5, 6, 7, 8, 9 or 10. In a further embodiment, the number of conservative substitutions in SEQ ID NO: 8 is not more than 10, e.g., 1, 2, 3, 4, 5, 6, 7, 8, 9 or 10. Examples of amino acid changes, conservative substitutions and fusion peptides are described in the second aspect herein.

In an embodiment of the fourth aspect, the variant releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a fifth aspect, the invention relates to polypeptides having alpha-galactosidase activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 11. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 11.

In a continuation of the fifth aspect, the invention relates to polypeptides having alpha-galactosidase activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 12.

In one embodiment, the polypeptide preferably comprises or consists of the amino acid sequence of SEQ ID NO: 12 or an allelic variant thereof; comprises the amino acid sequence of SEQ ID NO: 12 and a N-terminal and/or C-terminal His-tag and/or HQ-tag; or is a fragment thereof having alpha-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 12. In another embodiment, the polypeptide comprises or consists of amino acids 1 to 719 of SEQ ID NO: 11. In another embodiment, the polypeptide comprises or consists of the mature polypeptide of SEQ ID NO: 11. In another embodiment, the polypeptide comprises or consists of amino acids 1 to 719 of SEQ ID NO: 12. In an embodiment, the polypeptide has been isolated.

In a continuation of the fifth aspect, the invention relates to a polypeptide having alpha-galactosidase activity encoded by a polynucleotide having a sequence identity to the mature polypeptide coding sequence of SEQ ID NO: 10 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifth aspect, the polypeptide releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a continuation of the fifth aspect, the invention relates to variants of SEQ ID NO: 12 having alpha-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 12 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 12 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In another embodiment, the number of substitutions and/or deletions and/or insertions in SEQ ID NO: 12 is not more than 10, e.g., 1, 2, 3, 4, 5, 6, 7, 8, 9 or 10. In a further embodiment, the number of substitutions in SEQ ID NO: 12 is not more than 10, e.g., 1, 2, 3, 4, 5, 6, 7, 8, 9 or 10. In a further embodiment, the number of conservative substitutions in SEQ ID NO: 12 is not more than 10, e.g., 1, 2, 3, 4, 5, 6, 7, 8, 9 or 10. Examples of amino acid changes, conservative substitutions and fusion peptides are described in the second aspect herein.

In an embodiment of the fifth aspect, the variant releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a sixth aspect, the invention relates to polypeptides having alpha-galactosidase activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 14.

In a continuation of the sixth aspect, the invention relates to polypeptides having alpha-galactosidase activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 15. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 15.

In one embodiment, the polypeptide preferably comprises or consists of the amino acid sequence of SEQ ID NO: 14 or an allelic variant thereof; comprises the amino acid sequence of SEQ ID NO: 14 and a N-terminal and/or C-terminal His-tag and/or HQ-tag such as SEQ ID NO: 15; or is a fragment thereof having alpha-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 14. In another embodiment, the polypeptide comprises or consists of amino acids 1 to 731 of SEQ ID NO: 14. In another embodiment, the polypeptide comprises or consists of the mature polypeptide of SEQ ID NO: 15. In another embodiment, the polypeptide comprises or consists of amino acids 1 to 737 of SEQ ID NO: 15. In an embodiment, the polypeptide has been isolated.

In a continuation of the sixth aspect, the invention relates to a polypeptide having alpha-galactosidase activity encoded by a polynucleotide having a sequence identity to the mature polypeptide coding sequence of SEQ ID NO: 13 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the sixth aspect, the polypeptide releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a continuation of the sixth aspect, the invention relates to variants of SEQ ID NO: 14 having alpha-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 14 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 14 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 14 is not more than 10, e.g., 1, 2, 3, 4, 5, 6, 7, 8, 9 or 10. In another embodiment, the number of substitutions and/or deletions and/or insertions in SEQ ID NO: 14 is not more than 10, e.g., 1, 2, 3, 4, 5, 6, 7, 8, 9 or 10. In a further embodiment, the number of substitutions in SEQ ID NO: 14 is not more than 10, e.g., 1, 2, 3, 4, 5, 6, 7, 8, 9 or 10. In a further embodiment, the number of conservative substitutions in SEQ ID NO: 14 is not more than 10, e.g., 1, 2, 3, 4, 5, 6, 7, 8, 9 or 10. Examples of amino acid changes, conservative substitutions and fusion peptides are described in the second aspect herein.

In an embodiment of the sixth aspect, the variant releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a seventh aspect, the invention relates to polypeptides having alpha-galactosidase activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 18. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 18.

In a continuation of the seventh aspect, the invention relates to polypeptides having alpha-galactosidase activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 19. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 19.

In one embodiment, the polypeptide preferably comprises or consists of the amino acid sequence of SEQ ID NO: 19 or an allelic variant thereof; comprises the amino acid sequence of SEQ ID NO: 19 and a N-terminal and/or C-terminal His-tag and/or HQ-tag; or is a fragment thereof having alpha-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 19. In another embodiment, the polypeptide comprises or consists of amino acids 1 to 735 of SEQ ID NO: 18. In another embodiment, the polypeptide comprises or consists of the mature polypeptide of SEQ ID NO: 18. In another embodiment, the polypeptide comprises or consists of amino acids 1 to 735 of SEQ ID NO: 19. In an embodiment, the polypeptide has been isolated.

In a continuation of the seventh aspect, the invention relates to a polypeptide having alpha-galactosidase activity encoded by a polynucleotide having a sequence identity to the mature polypeptide coding sequence of SEQ ID NO: 17 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the seventh aspect, the polypeptide releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

In a continuation of the seventh aspect, the invention relates to variants of SEQ ID NO: 19 having alpha-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 19 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 19 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 19 is not more than 10, e.g., 1, 2, 3, 4, 5, 6, 7, 8, 9 or 10. In another embodiment, the number of substitutions and/or deletions and/or insertions in SEQ ID NO: 19 is not more than 10, e.g., 1, 2, 3, 4, 5, 6, 7, 8, 9 or 10. In a further embodiment, the number of substitutions in SEQ ID NO: 19 is not more than 10, e.g., 1, 2, 3, 4, 5, 6, 7, 8, 9 or 10. In a further embodiment, the number of conservative substitutions in SEQ ID NO: 19 is not more than 10, e.g., 1, 2, 3, 4, 5, 6, 7, 8, 9 or 10. Examples of amino acid changes, conservative substitutions and fusion peptides are described in the second aspect herein.

In an embodiment of the seventh aspect, the variant releases at least at least 19 g, such as at least 19.5 g, such as at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

Granules Comprising Polypeptides Having Alpha-Galactosidase Activity

In an eighth aspect, the invention relates to a granule comprising one or more polypeptides having alpha-galactosidase activity, wherein the polypeptide is selected from the group consisting of:
 (a) a polypeptide having at least 80% sequence identity to the polypeptide of SEQ ID NO: 2;
 (b) a polypeptide having at least 80% sequence identity to the polypeptide of SEQ ID NO: 5;
 (c) a polypeptide having at least 80% sequence identity to the polypeptide of SEQ ID NO: 8;
 (d) a polypeptide having at least 80% sequence identity to the polypeptide of SEQ ID NO: 12;
 (e) a polypeptide having at least 80% sequence identity to the polypeptide of SEQ ID NO: 14;
 (f) a polypeptide having at least 80% sequence identity to the polypeptide of SEQ ID NO: 19;
 (g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (h) a polypeptide comprising the polypeptide of (a), (b), (c), (d), (e), (f) or (g) and a N-terminal and/or C-terminal His-tag and/or HQ-tag;
 (i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and
 (j) a fragment of the polypeptide of (a), (b), (c), (d), (e), (f) or (g) having alpha-galactosidase activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment of the eighth aspect, the invention relates to a granule comprising one or more polypeptides having alpha-galactosidase activity, wherein the polypeptide is selected from the group consisting of:
 (a) a polypeptide having at least 85% sequence identity to the polypeptide of SEQ ID NO: 2;
 (b) a polypeptide having at least 85% sequence identity to the polypeptide of SEQ ID NO: 5;
 (c) a polypeptide having at least 85% sequence identity to the polypeptide of SEQ ID NO: 8;
 (d) a polypeptide having at least 85% sequence identity to the polypeptide of SEQ ID NO: 12;
 (e) a polypeptide having at least 85% sequence identity to the polypeptide of SEQ ID NO: 14;
 (f) a polypeptide having at least 85% sequence identity to the polypeptide of SEQ ID NO: 19;
 (g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(h) a polypeptide comprising the polypeptide of (a), (b), (c), (d), (e), (f) or (g) and a N-terminal and/or C-terminal His-tag and/or HQ-tag;

(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and (j) a fragment of the polypeptide of (a), (b), (c), (d), (e), (f) or (g) having alpha-galactosidase activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment of the eighth aspect, the invention relates to a granule comprising one or more polypeptides having alpha-galactosidase activity, wherein the polypeptide is selected from the group consisting of:

(a) a polypeptide having at least 90% sequence identity to the polypeptide of SEQ ID NO: 2;

(b) a polypeptide having at least 90% sequence identity to the polypeptide of SEQ ID NO: 5;

(c) a polypeptide having at least 90% sequence identity to the polypeptide of SEQ ID NO: 8;

(d) a polypeptide having at least 90% sequence identity to the polypeptide of SEQ ID NO: 12;

(e) a polypeptide having at least 90% sequence identity to the polypeptide of SEQ ID NO: 14;

(f) a polypeptide having at least 90% sequence identity to the polypeptide of SEQ ID NO: 19;

(g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(h) a polypeptide comprising the polypeptide of (a), (b), (c), (d), (e), (f) or (g) and a N-terminal and/or C-terminal His-tag and/or HQ-tag;

(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and (j) a fragment of the polypeptide of (a), (b), (c), (d), (e), (f) or (g) having alpha-galactosidase activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment of the eighth aspect, the invention relates to a granule comprising one or more polypeptides having alpha-galactosidase activity, wherein the polypeptide is selected from the group consisting of:

(a) a polypeptide having at least 95% sequence identity to the polypeptide of SEQ ID NO: 2;

(b) a polypeptide having at least 95% sequence identity to the polypeptide of SEQ ID NO: 5;

(c) a polypeptide having at least 95% sequence identity to the polypeptide of SEQ ID NO: 8;

(d) a polypeptide having at least 95% sequence identity to the polypeptide of SEQ ID NO: 12;

(e) a polypeptide having at least 95% sequence identity to the polypeptide of SEQ ID NO: 14;

(f) a polypeptide having at least 95% sequence identity to the polypeptide of SEQ ID NO: 19;

(g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 positions;

(h) a polypeptide comprising the polypeptide of (a), (b), (c), (d), (e), (f) or (g) and a N-terminal and/or C-terminal His-tag and/or HQ-tag;

(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and (j) a fragment of the polypeptide of (a), (b), (c), (d), (e), (f) or (g) having alpha-galactosidase activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment to any part of the eighth aspect, the GH36 polypeptide having alpha-galactosidase is obtained or obtainable from the taxonomic order Bacillales, preferably the family Bacillaceae, more preferably the genus *Bacillus*. In an embodiment, the GH36 polypeptide having alpha-galactosidase is obtained or obtainable from the taxonomic order Bacillales, preferably the family Bacillaceae and is selected from the group selected from SEQ ID NO: 2, SEQ ID NO: 5, SEQ ID NO:8 and SEQ ID NO: 14.

In one embodiment to any part of the eighth aspect, the GH36 polypeptide having alpha-galactosidase is obtained or obtainable from the taxonomic order Eurotiales, preferably the family Aspergillaceae, more preferably the genus *Aspergillus*. In an embodiment, the GH36 polypeptide having alpha-galactosidase is obtained or obtainable from the taxonomic order Eurotiales, preferably the family Aspergillaceae, more preferably the genus *Aspergillus* and is selected from the group selected from SEQ ID NO: 12 and SEQ ID NO: 19.

In one embodiment to any part of the eighth aspect, the composition comprises at least 0.01 mg of polypeptide (enzyme protein) per kilogram of composition, such as at least 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition. In one embodiment, the composition comprises at most 250 g of polypeptide per kilogram of composition, such as at most 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 250 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g, 75 g or 100 g per kilogram of composition and 150 g, 100 g, 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment to any part of the eighth aspect, the granule comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the eighth aspect, the granule comprises a core particle and one or more coatings. In a preferred embodiment, the coating comprises salt and/or wax and/or flour. Preferred formulations are disclosed in the formulation section below.

In one embodiment to any part of the eighth aspect, the granule comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment to any part of the eighth aspect, the granule comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

Liquid Formulations Comprising Polypeptides Having Alpha-Galactosidase Activity

In a ninth aspect, the invention relates to a liquid formulation comprising one or more polypeptides having alpha-galactosidase activity, wherein the liquid formulation comprises:
  (A) 0.001% to 25% w/w of polypeptide having alpha-galactosidase activity wherein the polypeptide having alpha-galactosidase activity is selected from the group consisting of:
    (a) a polypeptide having at least 80%, e.g., at least 85%, at least 90% or at least 95% sequence identity to the polypeptide of SEQ ID NO: 2;
    (b) a polypeptide having at least 80%, e.g., at least 85%, at least 90% or at least 95% sequence identity to the polypeptide of SEQ ID NO: 5;
    (c) a polypeptide having at least 80%, e.g., at least 85%, at least 90% or at least 95% sequence identity to the polypeptide of SEQ ID NO: 8;
    (d) a polypeptide having at least 80%, e.g., at least 85%, at least 90% or at least 95% sequence identity to the polypeptide of SEQ ID NO: 12;
    (e) a polypeptide having at least 80%, e.g., at least 85%, at least 90% or at least 95% sequence identity to the polypeptide of SEQ ID NO: 14;
    (f) a polypeptide having at least 80%, e.g., at least 85%, at least 90% or at least 95% sequence identity to the polypeptide of SEQ ID NO: 19;
    (g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
    (h) a polypeptide comprising the polypeptide of (a), (b), (c), (d), (e), (f) or (g) and a N-terminal and/or C-terminal His-tag and/or HQ-tag;
    (i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and
    (j) a fragment of the polypeptide of (a), (b), (c), (d), (e), (f) or (g) having alpha-galactosidase activity and having at least 90% of the length of the mature polypeptide; and
  (B) water.

In one embodiment of the ninth aspect, the invention relates to a liquid formulation comprising one or more polypeptides having alpha-galactosidase activity, wherein the liquid formulation comprises:
  (A) 0.001% to 25% w/w of polypeptide having alpha-galactosidase activity wherein the polypeptide having alpha-galactosidase activity is selected from the group consisting of:
    (a) a polypeptide having at least 80%, e.g., at least 85%, at least 90% or at least 95% sequence identity to the polypeptide of SEQ ID NO: 2;
    (b) a polypeptide having at least 80%, e.g., at least 85%, at least 90% or at least 95% sequence identity to the polypeptide of SEQ ID NO: 5;
    (c) a polypeptide having at least 80%, e.g., at least 85%, at least 90% or at least 95% sequence identity to the polypeptide of SEQ ID NO: 8;
    (d) a polypeptide having at least 80%, e.g., at least 85%, at least 90% or at least 95% sequence identity to the polypeptide of SEQ ID NO: 12;
    (e) a polypeptide having at least 80%, e.g., at least 85%, at least 90% or at least 95% sequence identity to the polypeptide of SEQ ID NO: 14;
    (f) a polypeptide having at least 80%, e.g., at least 85%, at least 90% or at least 95% sequence identity to the polypeptide of SEQ ID NO: 19;
    (g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(h) a polypeptide comprising the polypeptide of (a), (b), (c), (d), (e), (f) or (g) and a N-terminal and/or C-terminal His-tag and/or HQ-tag;

(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and (j) a fragment of the polypeptide of (a), (b), (c), (d), (e), (f) or (g) having alpha-galactosidase activity and having at least 90% of the length of the mature polypeptide;

(B) 20% to 80% w/w of polyol; and (C) water.

In one embodiment of the ninth aspect, the invention relates to a liquid formulation comprising one or more polypeptides having alpha-galactosidase activity, wherein the liquid formulation comprises:

(A) 0.001% to 25% w/w of polypeptide having alpha-galactosidase activity wherein the polypeptide having alpha-galactosidase activity is selected from the group consisting of:

(a) a polypeptide having at least 80%, e.g., at least 85%, at least 90% or at least 95% sequence identity to the polypeptide of SEQ ID NO: 2;

(b) a polypeptide having at least 80%, e.g., at least 85%, at least 90% or at least 95% sequence identity to the polypeptide of SEQ ID NO: 5;

(c) a polypeptide having at least 80%, e.g., at least 85%, at least 90% or at least 95% sequence identity to the polypeptide of SEQ ID NO: 8;

(d) a polypeptide having at least 80%, e.g., at least 85%, at least 90% or at least 95% sequence identity to the polypeptide of SEQ ID NO: 12;

(e) a polypeptide having at least 80%, e.g., at least 85%, at least 90% or at least 95% sequence identity to the polypeptide of SEQ ID NO: 14;

(f) a polypeptide having at least 80%, e.g., at least 85%, at least 90% or at least 95% sequence identity to the polypeptide of SEQ ID NO: 19;

(g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(h) a polypeptide comprising the polypeptide of (a), (b), (c), (d), (e), (f) or (g) and a N-terminal and/or C-terminal His-tag and/or HQ-tag;

(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and (j) a fragment of the polypeptide of (a), (b), (c), (d), (e), (f) or (g) having alpha-galactosidase activity and having at least 90% of the length of the mature polypeptide;

(B) 0.001% to 2.0% w/w preservative; and (C) water.

In one embodiment of the ninth aspect, the invention relates to a liquid formulation comprising one or more polypeptides having alpha-galactosidase activity, wherein the liquid formulation comprises:

(A) 0.001% to 25% w/w of polypeptide having alpha-galactosidase activity wherein the polypeptide having alpha-galactosidase activity is selected from the group consisting of:

(a) a polypeptide having at least 80%, e.g., at least 85%, at least 90% or at least 95% sequence identity to the polypeptide of SEQ ID NO: 2;

(b) a polypeptide having at least 80%, e.g., at least 85%, at least 90% or at least 95% sequence identity to the polypeptide of SEQ ID NO: 5;

(c) a polypeptide having at least 80%, e.g., at least 85%, at least 90% or at least 95% sequence identity to the polypeptide of SEQ ID NO: 8;

(d) a polypeptide having at least 80%, e.g., at least 85%, at least 90% or at least 95% sequence identity to the polypeptide of SEQ ID NO: 12;

(e) a polypeptide having at least 80%, e.g., at least 85%, at least 90% or at least 95% sequence identity to the polypeptide of SEQ ID NO: 14;

(f) a polypeptide having at least 80%, e.g., at least 85%, at least 90% or at least 95% sequence identity to the polypeptide of SEQ ID NO: 19;

(g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(h) a polypeptide comprising the polypeptide of (a), (b), (c), (d), (e), (f) or (g) and a N-terminal and/or C-terminal His-tag and/or HQ-tag;

(i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and (j) a fragment of the polypeptide of (a), (b), (c), (d), (e), (f) or (g) having alpha-galactosidase activity and having at least 90% of the length of the mature polypeptide;

(B) 20% to 80% w/w of polyol;

(C) 0.001% to 2.0% w/w preservative; and (D) water.

In one embodiment to any part of the ninth aspect, the GH36 polypeptide having alpha-galactosidase is obtained or obtainable from the taxonomic order Bacillales, preferably the family Bacillaceae, more preferably the genus *Bacillus*. In an embodiment, the GH36 polypeptide having alpha-galactosidase is obtained or obtainable from the taxonomic order Bacillales, preferably the family Bacillaceae and is selected from the group selected from SEQ ID NO: 2, SEQ ID NO: 5, SEQ ID NO:8 and SEQ ID NO: 14.

In one embodiment to any part of the ninth aspect, the GH36 polypeptide having alpha-galactosidase is obtained or obtainable from the taxonomic order Eurotiales, preferably the family Aspergillaceae, more preferably the genus *Aspergillus*. In an embodiment, the GH36 polypeptide having alpha-galactosidase is obtained or obtainable from the taxonomic order Eurotiales, preferably the family Aspergillaceae, more preferably the genus *Aspergillus* and is selected from the group selected from SEQ ID NO: 12 and SEQ ID NO: 19.

In one embodiment to any part of the ninth aspect, the liquid formulation comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the ninth aspect, the liquid formulation comprises one or more polyols, preferably a polyol selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment to any part of the ninth aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol. In one embodiment to any part of the ninth aspect, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600. In one embodiment to any part of the ninth aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment to any part of the ninth aspect, the preservative is selected from the group consisting of sodium sorbate, potassium sorbate, sodium benzoate and potassion benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.001% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassion benzoate or any combination thereof.

In one embodiment to any part of the ninth aspect, the liquid formulation comprises 0.01% to 25% w/w polypeptide having alpha-galactosidase activity, preferably 0.05% to 20% w/w polypeptide having alpha-galactosidase activity, more preferably 0.2% to 15% w/w polypeptide having alpha-galactosidase activity, more preferably 0.5% to 15% w/w polypeptide having alpha-galactosidase activity or most preferably 1.0% to 10% w/w polypeptide having alpha-galactosidase activity.

In one embodiment to any part of the ninth aspect, the liquid formulation comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment to any part of the ninth aspect, the liquid formulation comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

Sources of Polypeptides Having Alpha-Galactosidase Activity

A polypeptide having alpha-galactosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one embodiment, the polypeptide is from a bacterium of the class Bacilli, such as from the order Bacillales, or from the family Bacillaceae, or from the genus *Bacillus* or from the species *Bacillus acidopullulyticus, Bacillus* sp-19140 or *Bacillus deramificans*. In another embodiment, the polypeptide is from a bacterium of the class Bacilli, such as from the order Bacillales, or from the family Bacillaceae, or from the genus *Anoxybacillus* or from the species *Anoxybacillus bogrovensis*.

In a further embodiment, the polypeptide is from a fungus of the class Eurotiomycetes, such as from the order Eurotiales, or from the family Aspergillaceae, or from the genus *Aspergillus* or from the species *Aspergillus unguis* or *Aspergillus puniceus*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus triose* phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP),

*Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus nigeralpha*-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus nigeralpha*-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a Pseudomonas cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the *Fungi Imperfecti* (*Blastomycetes*). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium mer-* darium, *Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Bacillus* cell. In another aspect, the cell is a *Bacillus deramificans*, a *Bacillus* sp-19140 or a *Bacillus acidopullulyticus* cell. In a further, the cell is an *Anoxybacillus* cell. In another aspect, the cell is an *Anoxybacillus bogrovensis* cell.

In one aspect, the cell is an *Aspergillus* cell. In another aspect, the cell is an *Aspergillus sydowii* cell. In another aspect, the cell is an *Aspergillus puniceus* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected u778sing methods known in the art that are specific for the polypeptides alpha-galactosidase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the alpha-galactosidase activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In an embodiment, the composition comprises one or more polypeptides of the invention and one or more formulating agents, as described below.

In one aspect, the invention relates to a composition comprising one or more polypeptides having alpha-galactosidase activity of the invention and one or more formulating agents, wherein the polypeptide having alpha-galactosidase activity releases at least 19 g galactose per kg soybean meal when performed under the reaction conditions 20 mg polypeptide per kg soybean meal in 10% w/v 0.1M citric acid-phosphate buffer pH 6.5 incubating at 40° C. for 2 hours. In an embodiment, the alpha-galactosidase activity releases at least at least 19 g, such as at least 19.5 g, such as at least 20 g, at least 20.5 g, at least 21 g, at least 21.5 g, at least 22 g or at least 23 g galactose per kg soybean meal.

The compositions may further comprise multiple enzymatic activities, such as one or more (e.g., several) enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

The compositions may further comprise one or more microbes. In an embodiment, the microbe is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp.*, Carnobacterium* sp.*, Clostridium butyricum, Clostridium* sp.*, Enterococcus faecium, Enterococcus* sp.*, Lactobacillus* sp.*, Lactobacillus acidophilus, Lactobacillus farciminus, Lactobacillus rhamnosus, Lactobacillus reuteri, Lactobacillus salivarius, Lactococcus lactis, Lactococcus* sp.*, Leuconostoc* sp.*, Megasphaera elsdenii, Megasphaera* sp.*, Pediococcus acidilactici, Pediococcus* sp.*, Propionibacterium thoenii, Propionibacterium* sp. and *Streptococcus* sp. or any combination thereof.

Formulation

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1, 2-propylene glycol, 1, 3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the alpha-galactosidase of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the alpha-galactosidase of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 μm thick, particularly at least 0.5 μm, at least 1 μm or at least 5 μm. In some embodiments the thickness of the coating is below 100 μm, such as below 60 μm, or below 40 μm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 μm, such as less than 10 μm or less than 5 μm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93.0%), NH4H2PO4 (CH20° C.=93.1%), (NH4)2SO4(CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H2O), zinc sulfate heptahydrate (ZnSO4.7H2O), sodium phosphate dibasic heptahydrate (Na2HPO4.7H2O), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the alpha-galactosidase of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:

(a) a core comprising an alpha-galactosidase according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Plant Based Material

In an embodiment, the plant based material is from the taxonomic subclass rosids such as the taxonomic order Fabales or the the taxonomic order Brassicales.

In one embodiment, the plant based material from is from the family Fabaceae, such as the subfamilies Caesalpinioideae or Mimosoideae or Papilionoideae. In an embodiment, the plant based material from is from the sub-family Papilionoideae, such as the tribe Abreae or Amorpheae or Bossiaeeae or Brongniartieae or Cicereae or Crotalarieae or Dalbergieae or Desmodieae or Dipterygeae or Euchresteae or Fabeae or Galegeae or Genisteae or Hedysareae or Hypocalypteae or Indigofereae or Loteae or Millettieae or Mirbelieae or Phaseoleae or Podalyrieae or Psoraleeae or Robinieae or Sesbanieae or Sophoreae or Swartzieae or Thermopsideae or Trifolieae.

In one embodiment, the plant based material from the sub-family Papilionoideae is from the tribe Phaseoleae, such as the genus *Adenodolichos* or *Alistilus* or Amphicarpaea or *Ancistrotropis* or *Apios* or *Atylosia* or *Bionia* or *Bolusafra* or *Butea* or *Cajanus* or *Calopogonium* or *Camptosema* or *Canavalia* or *Centrosema* or *Cleobulia* or *Clitoria* or *Cochlianthus* or *Cochliasanthus* or Collaea or *Cologania* or *Condylostylis* or *Cratylia* or *Cymbosema* or Decorsea or *Dioclea* or *Dipogon* or *Dolichopsis* or *Dolichos* or *Dumasia* or *Dunbaria* or *Eriosema* or *Erythrina* or *Flemingia* or *Galactia* or *Glycine* or *Hardenbergia* or *Helicotropis* or *Kennedia* or *Lablab* or *Leptospron* or *Macroptilium* or *Macrotyloma* or *Mastersia* or *Mucuna* or *Mysanthus* or *Neonotonia* or *Neorautanenia* or *Nesphostylis* or *Nogra* or *Ophrestia* or *Otoptera* or *Oxyrhynchus* or *Pachyrhizus* or *Paracalyx* or *Phaseolus* or *Phylacium* or *Physostigma* or *Pseudeminia* or *Pseudovigna* or *Psophocarpus* or *Pueraria* or *Ramirezella* or *Rhodopis* or *Rhynchosia* or *Shuteria* or *Sigmoidotropis* or *Sinodolichos* or *Spathionema* or *Spatholobus* or *Sphenostylis* or *Strongylodon* or *Strophostyles* or *Teramnus* or *Teyleria* or *Vandasina* or Vatovaea or *Vigna* or *Wajira*.

In one embodiment, the plant based material from the sub-family Papilionoideae is from the genus *Glycine*, such as the species *Glycine aff. tabacina* or *Glycine albicans* or *Glycine aphyonota* or *Glycine arenaria* or *Glycine argyrea* or *Glycine canescens* or *Glycine clandestina* or *Glycine curvata* or *Glycine cyrtoloba* or *Glycine dolichocarpa* or *Glycine falcata* or *Glycine gracei* or *Glycine hirticaulis* or *Glycine lactovirens* or *Glycine latifolia* or *Glycine latrobeana* or *Glycine microphylla* or *Glycine peratosa* or *Glycine pindanica* or *Glycine pullenii* or *Glycine rubiginosa* or *Glycine stenophita* or *Glycine syndetika* or *Glycine tabacina* or *Glycine tomentella* or *Glycine* sp. T1 or *Glycine* sp. T5 or *Glycine gracilis* or *Glycine max* (soy bean) or *Glycine max*×*Glycine soja* or *Glycine soja* (wild soybean).

In one embodiment, the plant based material from the sub-family Papilionoideae is from the genus *Cajanus* such as the species *Cajanus cajan* (pigeon pea), *Cajanus cajanifolius* and *Cajanus scarabaeoide*.

In one embodiment, the plant based material from the sub-family Papilionoideae is from the genus *Phaseolus*, such as the species *Phaseolus acutifolius* (tepary bean) or *Phaseolus acutifolius* var. *latifolius* or *Phaseolus albescens* or *Phaseolus albiflorus* or *Phaseolus albinervus* or *Phaseolus altimontanus* or *Phaseolus amblyosepalus* or *Phaseolus angustissimus* or *Phaseolus augusti* or *Phaseolus bolivianus* or *Phaseolus campanulatus* or *Phaseolus carteri* or *Phaseolus chiapasanus* or *Phaseolus coccineus* (scarlet runner bean) or *Phaseolus coccineus* subsp. *coccineus* or *Phaseolus coccineus* subsp. *polyanthus* or *Phaseolus costaricensis* or *Phaseolus dasycarpus* or *Phaseolus dumosus* or *Phaseolus esperanzae* or *Phaseolus esquincensis* or *Phaseolus filiformis* (slimjim bean) or *Phaseolus glabellus* or *Phaseolus gladiolatus* or *Phaseolus grayanus* or *Phaseolus hintonii* or *Phaseolus jaliscanus* or *Phaseolus juquilensis* or *Phaseolus laxiflorus* or *Phaseolus leptostachyus* or *Phaseolus lignosus* or *Phaseolus lunatus* (lima bean) or *Phaseolus macrolepis* or *Phaseolus maculatifolius* or *Phaseolus maculatus* (co-colmeca bean) or *Phaseolus maculatus* subsp. *ritensis* or *Phaseolus macvaughii* or *Phaseolus magnilobatus* or *Phaseolus marechalii* or *Phaseolus micranthus* or *Phaseolus microcarpus* or *Phaseolus mollis* or *Phaseolus neglectus* or *Phaseolus nelsonii* or *Phaseolus nodosus* or *Phaseolus*

*novoleonensis* or *Phaseolus oaxacanus* or *Phaseolus oligospermus* or *Phaseolus pachyrrhizoides* or *Phaseolus parvifolius* or *Phaseolus parvulus* or *Phaseolus pauciflorus* or *Phaseolus pedicellatus* or *Phaseolus perplexus* or *Phaseolus persistentus* or *Phaseolus plagiocylix* or *Phaseolus pluriflorus* or *Phaseolus polymorphus* or *Phaseolus polystachios* or *Phaseolus polystachios* subsp. *sinuatus* or *Phaseolus polystachios* subsp. *smilacifolius* or *Phaseolus reticulatus* or *Phaseolus rotundatus* or *Phaseolus salicifolius* or *Phaseolus sonorensis* or *Phaseolus talamancensis* or *Phaseolus tenellus* or *Phaseolus texensis* or *Phaseolus tuerckheimii* or *Phaseolus vulgaris* (French bean) or *Phaseolus vulgaris* var. *aborigineus* or *Phaseolus vulgaris* var. *nanus* or *Phaseolus xanthotrichus* or *Phaseolus xolocotzii* or *Phaseolus zimapanensis*.

In one embodiment, the plant based material from the sub-family Papilionoideae is from the tribe Cicereae, such as the genus *Cicer*, such as the species *Cicer anatolicum* or *Cicer arietinum* (chickpea) or *Cicer bijugum* or *Cicer canariense* or *Cicer chorassanicum* or *Cicer cuneatum* or *Cicer echinospermum* or *Cicer flexuosum* or *Cicer floribundum* or *Cicer graecum* or *Cicer incisum* or *Cicer isauricum* or *Cicer judaicum* or *Cicer kermanense* or *Cicer macracanthum* or *Cicer microphyllum* or *Cicer montbretii* or *Cicer multijugum* or *Cicer nuristanicum* or *Cicer oxyodon* or *Cicer pinnatifidum* or *Cicer pungens* or *Cicer rechingeri* or *Cicer reticulaturn* or *Cicer songaricum* or *Cicer spiroceras* or *Cicer stapfianum* or *Cicer subaphyllum* or *Cicer tragacanthoides* or *Cicer yamashitae*

In one embodiment, the plant based material from the sub-family Papilionoideae is from the tribe Genisteae, such as the genus *Adenocarpus* or *Anarthrophyllum* or *Argyrocytisus* or *Argyrolobium* or *Calicotome* or *Chamaecytisus* or *Cytisophyllum* or *Cytisus* or *Dichilus* or *Echinospartum* or *Erinacea* or *Genista* or *Gonocytisus* or *Hesperolaburnum* or *Laburnum* or *Lembotropis* or *Lupinus* or *Melolobium* or *Petteria* or *Podocytisus* or *Polhillia* or *Retama* or *Sellocharis* or *Spartium* or *Stauracanthus* or *Teline* or *Ulex*

In one embodiment, the plant based material from the sub-family Papilionoideae is from the tribe Fabeae, such as the genus *Lathyrus* or *Lens* or *Pisum* or *Vavilovia* or *Vicia*.
In one embodiment, the plant based material from the sub-family Papilionoideae is from the genus *Lens*, such as the species *Lens culinaris* (lentil) or *Lens culinaris* subsp. *culinaris* or *Lens culinaris* subsp. *odemensis* or *Lens culinaris* subsp. *tomentosus* or *Lens cyanea* or *Lens ervoides* or *Lens lamottei* or *Lens nigricans* or *Lens orientalis* (ye bing dou).

In one embodiment, the plant based material from the sub-family Papilionoideae is from the genus *Vicia*, such as the species *Vicia garinensis* or *Vicia sojakii* or *Vicia rechingeri* or *Vicia kurdica* or *Vicia multijuga* or *Vicia akhmaganica* or *Vicia variabilis* or *Vicia variegata* or *Vicia persica* or *Vicia kotschyana* or *Vicia hirta* or *Vicia gregaria* or *Vicia ciceroidea* or *Vicia cappadocica* or *Vicia balansae* or *Vicia aucheri* or *Vicia* sp. 'telaponensis' or *Vicia venulosa* or *Vicia subvillosa* or *Vicia stenophylla* or *Vicia sicula* or *Vicia sibthorpii* or *Vicia semiglabra* or *Vicia scandens* or *Vicia pinetorum* or *Vicia picta* or *Vicia pectinata* or *Vicia paucifolia* or *Vicia palaestina* or *Vicia onobrychioides* or *Vicia ochroleuca* or *Vicia nataliae* or *Vicia montevidensis* or *Vicia monardii* or *Vicia minutiflora* or *Vicia menziesii* or *Vicia megalotropis* or *Vicia malosana* or *Vicia lunata* or *Vicia leucantha* or *Vicia leavenworthii* or *Vicia larissae* or *Vicia iranica* or *Vicia incana* or *Vicia hololasia* or *Vicia glauca* or *Vicia freyniana* or *Vicia floridana* or *Vicia filicaulis* or *Vicia ferreirensis* or *Vicia exigua* or *Vicia dennesiana* or *Vicia cypria* or *Vicia cretica* or *Vicia costata* or *Vicia claessensii* or *Vicia chaetocalyx* or *Vicia cassia* or *Vicia capreolata* or *Vicia caesarea* or *Vicia biennis* or *Vicia baicalensis* or *Vicia altissima* or *Vicia alpestris* or *Vicia acutifolia* or *Vicia pubescens* or *Vicia cirrhosa* or *Vicia koeieana* or *Vicia ramuliflora* or *Vicia multicaulis* or *Vicia parviflora* or *Vicia vicioides* or *Vicia tenuifolia* or *Vicia orobus* or *Vicia nigra* or *Vicia incisa* or *Vicia epetiolaris* or *Vicia crocea* or *Vicia sparsiflora* or *Vicia nummularia* or *Vicia dichroantha* or *Vicia cassubica* or *Vicia monantha* (bard vetch) or *Vicia cinerea* or *Vicia oroboides* or *Vicia tibetica* or *Vicia caroliniana* (Carolina or wood vetch) or *Vicia disperma* or *Vicia esdraelonensis* or *Vicia pulchella* or *Vicia mexicana* or *Vicia leucophaea* or *Vicia humilis* or *Vicia barbazitae* or *Vicia pyrenaica* or *Vicia qatmensis* or *Vicia lathyroides* or *Vicia cuspidata* or *Vicia dionysiensis* or *Vicia abbreviata* or *Vicia sepium* or *Vicia sericocarpa* or *Vicia noeana* or *Vicia hyrcanica* or *Vicia hybrida* or *Vicia galeata* or *Vicia ciliatula* or *Vicia assyriaca* or *Vicia tigridis* or *Vicia anatolica* or *Vicia sylvatica* or *Vicia dumetorum* or *Vicia mollis* or *Vicia aintabensis* or *Vicia peregrina* or *Vicia lutea* (yellow vetch) or *Vicia grandiflora* or *Vicia articulata* or *Vicia americana* or *Vicia michauxii* or *Vicia vicina* or *Vicia venosa* or *Vicia tetrasperma* or *Vicia ervilia* or *Vicia benghalensis* (purple or winter vetch) or *Vicia angustipinnata* or *Vicia amurensis* or *Vicia unijuga* or *Vicia pseudo-orobus* or *Vicia pisiformis* or *Vicia nipponica* or *Vicia nigricans* or *Vicia linearifolia* or *Vicia japonica* or *Vicia hirticalycina* or *Vicia fauriae* or *Vicia chosenensis* or *Vicia bungei* or *Vicia bifolia* or *Vicia amoena* or *Vicia montbretii* or *Vicia serratifolia* or *Vicia paucijuga* or *Vicia kalakhensis* or *Vicia johannis* or *Vicia hyaeniscyamus* or *Vicia galilaea* or *Vicia eristalioides* or *Vicia bithynica* or *Vicia melanops* or *Vicia ludoviciana* or *Vicia pannonica* or *Vicia narbonensis* or *Vicia villosa* or *Vicia hirsuta* or *Vicia sativa* (spring vetch) or *Vicia faba* (broad bean or fava bean) or *Vicia cracca* (bird vetch).

In one embodiment, the plant based material from the sub-family Papilionoideae is from the genus *Pisum*, such as the species *Pisum abyssinicum* (Abyssinian pea) or *Pisum fulvum* or *Pisum sativum* (pea) or *Pisum sativum* subsp. *asiaticum* or *Pisum sativum* subsp. *elatius* (wild pea) or *Pisum sativum* var. *pumilio* (Syrian fodder pea) or *Pisum sativum* subsp. *jomardii* or *Pisum sativum* subsp. *Sativum* or *Pisum sativum* var. *arvense* or *Pisum sativum* var. *choresmicum* or *Pisum sativum* var. *macrocarpon* (snow pea) or *Pisum sativum* var. *ponderosum* or *Pisum sativum* var. *tibetanicum* or *Pisum sativum* subsp. *transcaucasicum*

In one embodiment, the plant based material from the sub-family Papilionoideae is from the tribe Dalbergieae, such as the genus *Adesmia* or *Aeschynomene* or *Amicia* or *Andira* or *Arachis* or *Brya* or *Bryaspis* or *Cascaronia* or *Centrolobium* or *Chaetocalyx* or *Chapmannia* or *Cranocarpus* or *Cyclocarpa* or *Dalbergia* or *Diphysa* or *Discolobium* or *Etaballia* or *Fiebrigiella* or *Fissicalyx* or *Geissaspis* or *Geoffroea* or *Grazielodendron* or *Humularia* or *Hymenolobium* or *Inocarpus* or *Kotschya* or *Machaerium* or *Maraniona* or *Nissolia* or *Ormocarpopsis* or *Ormocarpum* or *Paramachaerium* or *Peltiera* or *Pictetia* or *Platymiscium* or *Platypodium* or *Poiretia* or *Pterocarpus* or *Ramorinoa* or *Riedeliella* or *Smithia* or *Soemmeringia* or *Steinbachiella* or *Stylosanthes* or *Tipuana* or *Weberbauerella* or *Zornia*.

In one embodiment, the plant based material from the sub-family Papilionoideae is from the genus *Arachis*, such as the species *Appressipila* (amendoim bravo) or *Arachis batizocoi* or *Arachis brevipetiolata* or *Arachis burcheffii* or *Arachis burkartii* or *Arachis cardenasii* or *Arachis chiq-*

*uitana* or *Arachis correntina* or *Arachis cruziana* or *Arachis decora* or *Arachis diogoi* or *Arachis duranensis* or *Arachis duranensis×Arachis stenosperma* or *Arachis glabrata* (amendoim-bravo) or *Arachis glabrata* var. *glabrata* or *Arachis glabrata* var. *hagenbeckii* or *Arachis glabrata×Arachis hypogaea* or *Arachis glandulifera* or *Arachis guaranitica* or *Arachis helodes* or *Arachis hermannii* or *Arachis hoehnei* or *Arachis hypogaea* (peanut) or *Arachis hypogaea* subsp. *Fastigiata* or *Arachis hypogaea* var. *vulgaris* (Spanish peanut) or *Arachis hypogaea* subsp. *Hypogaea* or *Arachis hypogaea* var. *hirsuta* or *Arachis ipaensis* or *Arachis ipaensis×Arachis magna* or *Arachis kempff-mercadoi* or *Arachis kretschmeri* or *Arachis kuhlmannii* or *Arachis linearifolia* or *Arachis lutescens* or *Arachis magna* or *Arachis major* or *Arachis matiensis* or *Arachis microsperma* or *Arachis monticola* or *Arachis palustris* or *Arachis paraguariensis* or *Arachis paraguariensis* subsp. *capibarensis* or *Arachis paraguariensis* subsp. *paraguariensis* or *Arachis pflugeae* or *Arachis pintoi* or *Arachis praecox* or *Arachis pusilla* (amendoim de caracar) or *Arachis repens* or *Arachis rigonii* or *Arachis schinini* or *Arachis simpsonii* or *Arachis stenophylla* or *Arachis stenosperma* or *Arachis stenosperma×Arachis cardenasii* or *Arachis sylvestris* (amendoim do porco) or *Arachis trinitensis* or *Arachis triseminata* or *Arachis tuberosa* or *Arachis valida* or *Arachis villosa* or *Arachis villosulicarpa* or *Arachis wiffiamsii*.

In one aspect, the plant based material is from the taxonomic order Brassicales, such as the family Brassicaceae, preferably the tribe Brassiceae, more preferably the family *Brassica*.

In one embodiment, the plant based material from the tribe Brassiceae is from the family *Brassica*, such as *Brassica aucheri*, *Brassica balearica*, *Brassica barrelled*, *Brassica carinata* (Abyssinian mustard), *Brassica carinata×Brassica napus*, *Brassica carinata×Brassica rapa*, *Brassica cretica*, *Brassica deflexa*, *Brassica desnottesii*, *Brassica drepanensis*, *Brassica elongata*, *Brassica fruticulosa*, *Brassica fruticulosa* subsp. *cossoniana*, *Brassica fruticulosa* subsp. *mauritanica*, *Brassica fruticulosa* subsp. *rifana*, *Brassica gravinae*, *Brassica hilarionis*, *Brassica hybrid cultivar*, *Brassica incana*, *Brassica insularis*, *Brassica insularis* subsp. *insularis*, *Brassica juncea* (Indian mustard), *Brassica juncea* var. *crassicaulis*, *Brassica juncea* var. *gemmifera*, *Brassica juncea* var. *gracilis*, *Brassica juncea* var. *juncea*, *Brassica juncea* var. *multiceps*, *Brassica juncea* var. *multisecta*, *Brassica juncea* var. *napiformis* (jie cai ge da), *Brassica juncea* var. *rugosa*, *Brassica juncea* var. *strumata*, *Brassica juncea* var. *subintegrifolia*, *Brassica juncea* var. *tumida* (zha cai), *Brassica juncea* var. *utilis*, *Brassica macrocarpa*, *Brassica maurorum*, *Brassica montana*, *Brassica napus* (rape), *Brassica napus* subsp. *rapifera* (Swedish turnip), *Brassica napus* var. *napus* (annual rape), *Brassica napus×Brassica rapa*, *Brassica nigra* (black mustard), *Brassica nigra* var. *abyssinica*, *Brassica oleracea*, *Brassica oleracea* var. *albiflora*, *Brassica oleracea* var. *alboglabra* (Chinese kale), *Brassica oleracea* var. *botrytis* (cauliflower), *Brassica oleracea* var. *capitata* (cabbage), *Brassica oleracea* var. *costata* (Bedford cabbage), *Brassica oleracea* var. *gemmifera* (Brussels sprouts), *Brassica oleracea* var. *gongylodes* (kohlrabi), *Brassica oleracea* var. *italica* (asparagus broccoli), *Brassica oleracea* var. *medullosa* (marrow-stem kale), *Brassica oleracea* var. *oleracea*, *Brassica oleracea* var. *ramosa* (branching bush kale), *Brassica oleracea* var. *sabauda*, *Brassica oleracea* var. *viridis* (kale), *Brassica oleracea×Brassica rapa* subsp. *pekinensis*, *Brassica oxyrrhina*, *Brassica procumbens*, *Brassica rapa* (field mustard), *Brassica rapa* subsp. *chinensis* (bok-choy), *Brassica rapa* var. *parachinensis* (cai xin), *Brassica rapa* var. *purpuraria* (purple stem mustard), *Brassica rapa* subsp. *narinosa*, *Brassica rapa* subsp. *nipposinica* (mizuna), *Brassica rapa* var. *perviridis* (kabuna), *Brassica rapa* subsp. *oleifera* (biennial turnip rape), *Brassica rapa* (Nippo-oleifera Group), *Brassica rapa* subsp. *pekinensis* (Chinese cabbage), *Brassica rapa* subsp. *rapa* (turnip), *Brassica rapa* var. *oleifera*, *Brassica rapa×Brassica nigra*, *Brassica repanda*, *Brassica repanda* subsp. *baldensis*, *Brassica repanda* subsp. *blancoana*, *Brassica repanda* subsp. *cadevallii*, *Brassica repanda* subsp. *confusa*, *Brassica repanda* subsp. *glabrescens*, *Brassica repanda* subsp. *gypsicola*, *Brassica repanda* subsp. *latisiliqua*, *Brassica repanda* subsp. *maritima*, *Brassica repanda* subsp. *repanda*, *Brassica repanda* subsp. *saxatilis*, *Brassica rupestris*, *Brassica ruvo* (broccoletto), *Brassica souliei*, *Brassica souliei* subsp. *amplexicaulis*, *Brassica spinescens*, *Brassica toumefortii*, *Brassica villosa* or *Brassica villosa* subsp. *Bivoniana*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Animal Feed and Animal Feed Additives

The present invention also relates to animal feed compositions and animal feed additives comprising one or more alpha-galactosidases of the invention. In an embodiment, the animal feed or animal feed additive comprises a formulating agent and one or more alpha-galactosidases of the invention. In a further embodiment, the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one alpha-galactosidase as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samensteling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

The animal feed composition of the invention may also contain insect protein, such as protein from mealworm, housefly or black soldier fly larvae, typically in meal form. Insect meal may replace fishmeal entirely or in part, and thus may constitute 0-10% of the total feed.

In still further particular embodiments, the animal feed composition of the invention contains 0-80% maize; and/or 0-80% sorghum; and/or 0-70% wheat; and/or 0-70% barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Brassicaceae, Amaranthaceae, and Poaceae, such as soybean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Amaranthaceae, e.g. beet, sugar beet, spinach or quinoa. Other examples of vegetable protein sources are rapeseed, crambe and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) alpha-galactosidase/enzyme preparation may also be added before or during the feed ingredient step. Typically a liquid alpha-galactosidase/enzyme preparation comprises the alpha-galactosidase of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the alpha-galactosidase can be prepared by freezing a mixture of liquid enzyme solution with a bulking agent such as ground soybean meal, and then lyophilizing the mixture.

In an embodiment, the animal feed or animal feed additive comprises one or more additional enzymes. In an embodiment, the animal feed comprises one or more microbes. In an embodiment, the animal feed comprises one or more vitamins. In an embodiment, the animal feed comprises one or more minerals. In an embodiment, the animal feed comprises one or more amino acids. In an embodiment, the animal feed comprises one or more other feed ingredients.

In another embodiment, the animal feed or animal feed additive comprises the polypeptide of the invention, one or more formulating agents and one or more additional enzymes. In an embodiment, the animal feed or animal feed additive comprises the polypeptide of the invention, one or more formulating agents and one or more microbes. In an embodiment, the animal feed comprises the polypeptide of the invention, one or more formulating agents and one or more vitamins. In an embodiment, the animal feed or animal feed additive comprises one or more minerals. In an embodiment, the animal feed or animal feed additive comprises the polypeptide of the invention, one or more formulating agents and one or more amino acids. In an embodiment, the animal feed or animal feed additive comprises the polypeptide of the invention, one or more formulating agents and one or more other feed ingredients.

In a further embodiment, the animal feed or animal feed additive comprises the polypeptide of the invention, one or more formulating agents and one or more components selected from the list consisting of: one or more additional enzymes; one or more microbes; one or more vitamins; one or more minerals; one or more amino acids; and one or more other feed ingredients.

In an embodiment, the animal feed additive comprises one or more formulating agents, preferably as described herein below.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

The final enzyme concentration in the diet is within the range of 0.01-200 mg enzyme protein per kg diet, preferably between 0.1-100 mg/kg diet, more preferably 0.5-50 mg, even more preferably 1-25 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; 5-50; 10-30; 20-30; 10-20; 15-25; or 1-10;—all these ranges being in mg alpha-galactosidase protein per kg feed (ppm).

For determining mg alpha-galactosidase protein per kg feed, the alpha-galactosidase is purified from the feed composition, and the specific activity of the purified alpha-galactosidase is determined using a relevant assay (see under alpha-galactosidase activity). The alpha-galactosidase activity of the feed composition as such is also determined using the same assay, and on the basis of these two determinations, the dosage in mg alpha-galactosidase protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The same principles apply for determining mg alpha-galactosidase protein in feed additives. Of course, if a sample is available of the alpha-galactosidase used for preparing the feed additive or the feed, the specific activity is determined from this sample (no need to purify the alpha-galactosidase from the feed composition or the additive).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, galactanase, mannanase, dextranase, lysozyme and galactosidase is described in Henrissat et al, "The carbohydrate-active enzymes database (CAZy) in 2013", *Nucl. Acids Res.* (1 Jan. 2014) 42 (D1): D490-D495; see also www.cazy.org.

Thus the composition of the invention may also comprise at least one other enzyme selected from the group comprising of acetylxylan esterase (EC 3.1.1.23), acylglycerol lipase (EC 3.1.1.72), alpha-amylase (EC 3.2.1.1), beta-amylase (EC 3.2.1.2), arabinofuranosidase (EC 3.2.1.55), cellobiohydrolases (EC 3.2.1.91), cellulase (EC 3.2.1.4), feruloyl esterase (EC 3.1.1.73), galactanase (EC 3.2.1.89), alpha-galactosidase (EC 3.2.1.22), beta-galactosidase (EC 3.2.1.23), beta-glucanase (EC 3.2.1.6), beta-glucosidase (EC 3.2.1.21), triacylglycerol lipase (EC 3.1.1.3), lysophospholipase (EC 3.1.1.5), lysozyme (EC 3.2.1.17), alpha-mannosidase (EC 3.2.1.24), beta-mannosidase (mannanase) (EC 3.2.1.25), phytase (EC 3.1.3.8, EC 3.1.3.26, EC 3.1.3.72), phospholipase A1 (EC 3.1.1.32), phospholipase A2 (EC 3.1.1.4), phospholipase D (EC 3.1.4.4), protease (EC 3.4), pullulanase (EC 3.2.1.41), pectinesterase (EC 3.1.1.11), xylanase (EC 3.2.1.8, EC 3.2.1.136), beta-xylosidase (EC 3.2.1.37), or any combination thereof.

In a particular embodiment the composition of the invention comprises a galactanase (EC 3.2.1.89) and a beta-galactosidase (EC 3.2.1.23).

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococcus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis*: 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1 \times 10^6$ and $1 \times 10^{12}$ CFU/kg of dry matter, and more preferably between $1 \times 10^7$ and $1 \times 10^{11}$ CFU/kg of dry matter. In a more preferred embodiment the bacterial count of each of the bacterial strains in the animal feed composition is between $1 \times 10^8$ and $1 \times 10^{10}$ CFU/kg of dry matter.

The bacterial count of each of the bacterial strains in the animal feed composition is between $1 \times 10^5$ and $1 \times 10^{15}$ CFU/animal/day, preferably between $1 \times 10^7$ and $1 \times 10^{13}$ CFU/animal/day, and more preferably between $1 \times 10^8$ and $1 \times 10^{12}$ CFU/animal/day. In a more preferred embodiment the bacterial count of each of the bacterial strains in the animal feed composition is between $1 \times 10^9$ and $1 \times 10^{11}$ CFU/animal/day.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Gallipro®, Gallipro® Max, Probios® Guard, Lactiferm® and Bioplus® (Chr Hansen), PoultryStar®, PoultryStar® sol, PoultryStar® me, AquaStar® (Biomin), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

Examples of commercial products are Crina® (DSM Nutritional Products); Cinergy™, Cinergy™ FIT, Biacid™, (Cargill), Digestarom® and Digestarom® DC (Biomin) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate).

Examples of commercial products are VevoVitall® (DSM Nutritional Products), Amasil®, Luprisil®, Lupro-Grain®, Lupro-Cid®, Lupro-Mix®, Lupro-Mix® NA (BASF), n-Butyric Acid AF (OXEA), Biacid™, Prohacid™ Classic and Prohacid™ Advance™ (Cargill), Biotronic® (Biomin) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |

TABLE 1-continued

Typical vitamin recommendations

| Vitamin | Piglet diet | Broiler diet |
|---|---|---|
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antimicrobial peptides and anti-fungal polypeptides.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are 018, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid. Examples of amino acids which are used in animal feed are lysine, alanine, beta-alanine, threonine, methionine and tryptophan.

Methods of Improving Animal Performance

In another aspect, the invention relates to a method of improving one or more performance parameters of an animal comprising administering to the animal the polypeptide of the invention or a composition, an animal feed or an animal feed additive comprising one or more polypeptides of the invention.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

In one embodiment, the animal feed comprises one or more formulating agents as defined herein. In one embodiment, the animal feed comprises one or more additional enzymes as defined herein. In one embodiment, the animal feed comprises one or more microbes as defined herein. In one embodiment, the animal feed comprises plant based material from the subclass rosids. In a preferred embodiment, the animal feed has been pelleted.

In an embodiment, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In one embodiment, the polypeptide of the invention is SEQ ID NO: 2. In one embodiment, the polypeptide of the invention is SEQ ID NO: 3. In one embodiment, the polypeptide of the invention is SEQ ID NO: 5. In one embodiment, the polypeptide of the invention is SEQ ID NO: 6. In one embodiment, the polypeptide of the invention is SEQ ID NO: 8. In one embodiment, the polypeptide of the invention is SEQ ID NO: 9. In one embodiment, the polypeptide of the invention is SEQ ID NO: 11. In one embodiment, the polypeptide of the invention is SEQ ID NO: 12. In one embodiment, the polypeptide of the invention is SEQ ID NO: 14. In one embodiment, the polypeptide of the invention is SEQ ID NO: 15. In one embodiment, the polypeptide of the invention is SEQ ID NO: 18. In one embodiment, the polypeptide of the invention is SEQ ID NO: 19.

In one embodiment, the term 'improving one or more performance parameters of an animal' means that there is an increase in body weight gain. In another embodiment, the term 'improving one or more performance parameters of an animal' means that there is an improved feed conversion ratio. In a further embodiment, 'the term 'improving one or more performance parameters of an animal' means that there is an increased feed efficiency. In a further embodiment, the term 'improving one or more performance parameters of an animal' means that there is an increase in body weight gain and/or an improved feed conversion ratio and/or an increased feed efficiency.

Method for Improving the Nutritional Value of Animal Feed

The term improving the nutritional value of an animal feed means improving the availability of nutrients in the feed. The nutritional values refers in particular to improving the solubilisation and degradation of the raffinose family of oligosaccharides (RFOs), such as the trisaccharide raffinose, the tetrasaccharide stachyose, and the pentasaccharide verbascose, thereby increasing the amount of galactose released which can be utilised by the animal. Consequently, an improved galactose release will result in an improvement of the nutritional value of the feed, thus resulting in increased growth rate and/or weight gain and/or feed conversion (i.e. the weight of ingested feed relative to weight gain).

Thus the invention further relates to a method for improving the nutritional value of an animal feed comprising treating the animal feed with the polypeptide of the invention or a composition or an animal feed additive comprising one or more polypeptides of the invention. In an embodiment, the animal feed will have improved nutrient digestibility.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

In one embodiment, the polypeptide of the invention is SEQ ID NO: 2. In one embodiment, the polypeptide of the invention is SEQ ID NO: 3. In one embodiment, the polypeptide of the invention is SEQ ID NO: 5. In one embodiment, the polypeptide of the invention is SEQ ID NO: 6. In one embodiment, the polypeptide of the invention is SEQ ID NO: 8. In one embodiment, the polypeptide of the invention is SEQ ID NO: 9. In one embodiment, the polypeptide of the invention is SEQ ID NO: 11. In one embodiment, the polypeptide of the invention is SEQ ID NO: 12. In one embodiment, the polypeptide of the invention is SEQ ID NO: 14. In one embodiment, the polypeptide of the invention is SEQ ID NO: 15. In one embodiment, the polypeptide of the invention is SEQ ID NO: 18. In one embodiment, the polypeptide of the invention is SEQ ID NO: 19.

Method for Reducing the Antinutritional Effects of an Animal Feed

An excessive amount of oligosaccharides in the hindgut can result in antinutritional effects due to flatulence production. By reducing the amount of oligosaccharide fermentation, the antinutritional effects of some animal feeds can be reduced resulting in improved gut and animal health.

Thus the invention further relates to a method for reducing the antinutritional effects of an animal feed comprising adding to the feed the polypeptide of the invention or a composition or an animal feed additive comprising one or more polypeptides of the invention.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

In one embodiment, the polypeptide of the invention is SEQ ID NO: 2. In one embodiment, the polypeptide of the invention is SEQ ID NO: 3. In one embodiment, the polypeptide of the invention is SEQ ID NO: 5. In one embodiment, the polypeptide of the invention is SEQ ID NO: 6. In one embodiment, the polypeptide of the invention is SEQ ID NO: 8. In one embodiment, the polypeptide of the invention is SEQ ID NO: 9. In one embodiment, the polypeptide of the invention is SEQ ID NO: 11. In one embodiment, the polypeptide of the invention is SEQ ID NO: 12. In one embodiment, the polypeptide of the invention is SEQ ID NO: 14. In one embodiment, the polypeptide of the invention is SEQ ID NO: 15. In one embodiment, the polypeptide of the invention is SEQ ID NO: 18. In one embodiment, the polypeptide of the invention is SEQ ID NO: 19.

Methods of Preparing an Animal Feed

In another aspect, the invention relates to a method of preparing an animal feed, comprising mixing the polypeptide of the invention or a composition, an animal feed or an animal feed additive comprising one or more polypeptides of the invention with plant based material.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

In one embodiment, the polypeptide of the invention is SEQ ID NO: 2. In one embodiment, the polypeptide of the invention is SEQ ID NO: 3. In one embodiment, the polypeptide of the invention is SEQ ID NO: 5. In one embodiment, the polypeptide of the invention is SEQ ID NO: 6. In one embodiment, the polypeptide of the invention is SEQ ID NO: 8. In one embodiment, the polypeptide of the invention is SEQ ID NO: 9. In one embodiment, the polypeptide of the invention is SEQ ID NO: 11. In one embodiment, the polypeptide of the invention is SEQ ID NO: 12. In one embodiment, the polypeptide of the invention is SEQ ID NO: 14. In one embodiment, the polypeptide of the invention is SEQ ID NO: 15. In one embodiment, the polypeptide of the invention is SEQ ID NO: 18. In one embodiment, the polypeptide of the invention is SEQ ID NO: 19.

Uses

The present invention is also directed to methods for using the polypeptides having alpha-galactosidase activity, or compositions thereof, for e.g. animal feed. The present invention is also directed to processes for using the polypeptides having alpha-galactosidase activity, or compositions thereof, such as e.g. those described below.

Use in Animal Feed

The present invention is also directed to methods for using the alpha-galactosidases of the invention in animal feed.

The term animal includes all animals. Examples of animals are non-ruminants, and ruminants. Ruminant animals include, for example, animals such as sheep, goats, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

In the use according to the invention the alpha-galactosidases can be fed to the animal before, after, or simultaneously with the diet. The latter is preferred.

In a particular embodiment, the alpha-galactosidase, in the form in which it is added to the feed, or when being included in a feed additive, is well-defined. Well-defined means that the alpha-galactosidase preparation is at least 50% pure as determined by Size-exclusion chromatography (see Example 12 of WO 01/58275). In other particular embodiments the alpha-galactosidase preparation is at least 60, 70, 80, 85, 88, 90, 92, 94, or at least 95% pure as determined by this method.

A well-defined alpha-galactosidase preparation is advantageous. For instance, it is much easier to dose correctly to the feed a alpha-galactosidase that is essentially free from interfering or contaminating other alpha-galactosidases. The term dose correctly refers in particular to the objective of obtaining consistent and constant results, and the capability of optimizing dosage based upon the desired effect.

For the use in animal feed, however, the alpha-galactosidase need not be that pure; it may e.g. include other enzymes, in which case it could be termed an alpha-galactosidase preparation.

The alpha-galactosidase preparation can be (a) added directly to the feed, or (b) it can be used in the production of one or more intermediate compositions such as feed additives or premixes that is subsequently added to the feed (or used in a treatment process). The degree of purity described above refers to the purity of the original alpha-galactosidase preparation, whether used according to (a) or (b) above.

Preferred Embodiments of the Invention

Preferred embodiments of the invention are described in the set of items below.
1. A method of releasing galactose from plant based material, comprising treating the plant based material with one or more GH36 polypeptides having alpha-galactosidase activity, wherein the GH36 polypeptide having alpha-galactosidase activity is selected from the group consisting of:
   (a) a polypeptide having at least 80% sequence identity to the polypeptide of SEQ ID NO: 2;
   (b) a polypeptide having at least 80% sequence identity to the polypeptide of SEQ ID NO: 5;
   (c) a polypeptide having at least 80% sequence identity to the polypeptide of SEQ ID NO: 8;
   (d) a polypeptide having at least 80% sequence identity to the polypeptide of SEQ ID NO: 12;
   (e) a polypeptide having at least 80% sequence identity to the polypeptide of SEQ ID NO: 14;
   (f) a polypeptide having at least 80% sequence identity to the polypeptide of SEQ ID NO: 19;
   (g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (h) a polypeptide comprising the polypeptide of (a), (b), (c), (d), (e), (f) or (g) and a N-terminal and/or C-terminal His-tag and/or HQ-tag;
   (i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and
   (j) a fragment of the polypeptide of (a), (b), (c), (d), (e), (f) or (g) having alpha-galactosidase activity and having at least 90% of the length of the mature polypeptide.
2. A method of releasing galactose from plant based material, comprising treating the plant based material with one or more GH36 polypeptides having alpha-galactosidase activity, wherein:
   (A) the GH36 polypeptide releases at least 19 g galactose per kg soybean meal; and
   (B) the GH36 polypeptide having alpha-galactosidase activity is selected from the group consisting of:
      (a) a polypeptide having at least 80% sequence identity to the polypeptide of SEQ ID NO: 2;
      (b) a polypeptide having at least 80% sequence identity to the polypeptide of SEQ ID NO: 5;
      (c) a polypeptide having at least 80% sequence identity to the polypeptide of SEQ ID NO: 8;
      (d) a polypeptide having at least 80% sequence identity to the polypeptide of SEQ ID NO: 12;
      (e) a polypeptide having at least 80% sequence identity to the polypeptide of SEQ ID NO: 14;
      (f) a polypeptide having at least 80% sequence identity to the polypeptide of SEQ ID NO: 19;
      (g) a variant of the polypeptide selected from the group consisting of SEQ ID NO: 2, SEQ ID NO: 5, SEQ ID NO: 8, SEQ ID NO: 12, SEQ ID NO: 14 and SEQ ID NO: 19, wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
      (h) a polypeptide comprising the polypeptide of (a), (b), (c), (d), (e), (f) or (g) and a N-terminal and/or C-terminal His-tag and/or HQ-tag;
      (i) a polypeptide comprising the polypeptide of (a), (b), (c), (d), (e), (f) or (g) and a N-terminal and/or C-terminal extension of up to 10 amino acids, e.g. 1, 2, 3, 4, 5, 6, 7, 8, 9 or 10 amino acids; and (j) a fragment of the polypeptide of (a), (b), (c), (d), (e), (f) or (g) having alpha-galactosidase activity and having at least 90% of the length of the mature polypeptide.

3. The method according to any of items 1 to 2, wherein the GH36 polypeptide releases at least 19 g, such as at least 19.5 g, at least 20 g, at least 20.5 g, at least 21 g, at least 21.5 g, at least 22 g or at least 23 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

4. The method according to any of items 1 to 3, wherein the GH36 polypeptide comprises or consists of amino acids 1 to 728 of SEQ ID NO: 2, amino acids 1 to 734 of SEQ ID NO: 3, amino acids 1 to 731 of SEQ ID NO: 5, amino acids 1 to 737 of SEQ ID NO: 6, amino acids 1 to 732 of SEQ ID NO: 8, amino acids 1 to 738 of SEQ ID NO: 9, amino acids 1 to 719 of SEQ ID NO: 11, amino acids 1 to 719 of SEQ ID NO: 12, amino acids 1 to 731 of SEQ ID NO: 14, amino acids 1 to 737 of SEQ ID NO: 15, amino acids 1 to 735 of SEQ ID NO: 18, or amino acids 1 to 735 of SEQ ID NO: 19.

5. The method according to any of items 1 to 4, wherein the plant based material is from the taxonomic subclass rosids.

6. The method according to any of items 1 to 4, wherein the plant based material is from the family Fabaceae, preferably the sub-family Papilionoideae.

7. The method according to any of items 1 to 4, wherein the plant based material is from the tribe Phaseoleae, Cicereae, Genisteae, Fabeae, Dalbergieae or Phaseoleae.

8. The method according to any of items 1 to 4, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

9. An isolated polypeptide having alpha-galactosidase activity, selected from the group consisting of:
(a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 2;
(b) a polypeptide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 5;
(c) a polypeptide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 8;
(d) a polypeptide having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 12;
(e) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 14;
(f) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 19;
(g) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;
(h) a polypeptide encoded by a polynucleotide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 4;
(i) a polypeptide encoded by a polynucleotide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7;
(j) a polypeptide encoded by a polynucleotide having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 12;
(k) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 14;
(l) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 19;
(m) a variant of SEQ ID NO: 2 wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(n) a variant of SEQ ID NO: 5 wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (o) a variant of SEQ ID NO: 8 wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (p) a variant of SEQ ID NO: 12 wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (q) a variant of SEQ ID NO: 14 wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (r) a variant of SEQ ID NO: 19 wherein the variant has alpha-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (s) a polypeptide comprising the polypeptide of (a), (b), (c), (d), (e), (f), (g), (h), (i), (j), (k), (l), (m), (n), (o), (p), (q) or (r) and a N-terminal and/or C-terminal His-tag and/or HQ-tag;
  (t) a polypeptide comprising the polypeptide of (a), (b), (c), (d), (e), (f), (g), (h), (i), (j), (k), (l), (m), (n), (o), (p), (q) or (r) and a N-terminal and/or C-terminal extension of up to 10 amino acids, e.g. 1, 2, 3, 4, 5, 6, 7, 8, 9 or 10 amino acids; and
  (u) a fragment of the polypeptide of (a), (b), (c), (d), (e), (f), (g), (h), (i), (j), (k), (l), (m), (n), (o), (p), (q) or (r) alpha-galactosidase activity and having at least 90% of the length of the mature polypeptide.

10. The polypeptide according to item 9, wherein the polypeptide comprises or consists of amino acids 1 to 728 of SEQ ID NO: 2, amino acids 1 to 734 of SEQ ID NO: 3, amino acids 1 to 731 of SEQ ID NO: 5, amino acids 1 to 737 of SEQ ID NO: 6, amino acids 1 to 732 of SEQ ID NO: 8, amino acids 1 to 738 of SEQ ID NO: 9, amino acids 1 to 719 of SEQ ID NO: 11 or amino acids 1 to 719 of SEQ ID NO: 12, amino acids 1 to 731 of SEQ ID NO: 14, amino acids 1 to 737 of SEQ ID NO: 15, amino acids 1 to 735 of SEQ ID NO: 18, or amino acids 1 to 735 of SEQ ID NO: 19.

11. A composition comprising one or more polypeptides of any of items 9 to 10.

12. The composition of item 11 further comprising one or more formulating agents.

13. The composition of item 12, wherein the one or more formulating agent is selected from the group consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose or any combination thereof.

14. The composition of any of items 11 to 13 further comprising one or more additional enzymes.

15. The composition of item 14, wherein the one or more additional enzymes is selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

16. The composition of any of items 11 to 15 further comprising one or more microbes.

17. The composition of item 16, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

18. The composition of any of items 11 to 17 further comprising plant based material.

19. The composition of item 18, wherein the plant based material is from the taxonomic subclass rosids.

20. The composition of item 18, wherein the plant based material is from the family Fabaceae, preferably the sub-family Papilionoideae.

21. The composition of item 18, wherein the plant based material is from the tribe Phaseoleae, Cicereae, Genisteae, Fabeae, Dalbergieae or Phaseoleae or any combination thereof.

22. The composition of item 18, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

23. A granule comprising one or more polypeptides of any of items 9 to 10 or the composition of any of items 11 to 17.

24. The granule of item 23 wherein the granule is coated.

25. The granule of item 24 wherein the coating comprises a salt and/or wax and/or a flour.
26. An animal feed additive comprising one or more polypeptides of any of items 9 to 10, the composition of any of items 11 to 17 or the granule of any of items 23 to 25 and one or more components selected from the list consisting of:
   one or more vitamins;
   one or more minerals;
   one or more amino acids;
   one or more prebiotics;
   one or more phytogenics;
   one or more organic acids; and
   one or more other feed ingredients.
27. An animal feed comprising plant based material and one or more polypeptides of any of items 9 to 10, the composition of any of items 11 to 17, the granule of any of items 23 to 25 or the animal feed additive of item 26.
28. The animal feed of item 27, wherein the plant based material is from the subclass rosids, preferably the family Fabaceae, more preferably the sub-family Papilionoideae or even more preferably is from the tribe Phaseoleae, Cicereae, Genisteae, Fabeae, Dalbergieae or Phaseoleae or any combination thereof.
29. The animal feed of item 27, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
30. A pelleted animal feed comprising plant based material and one or more polypeptides of any of items 9 to 10, the composition of any of items 11 to 17, the granule of any of items 23 to 25 or the animal feed additive of item 26.
31. The pelleted animal feed of item 30, wherein the plant based material is from the subclass rosids, preferably the family Fabaceae, more preferably the sub-family Papilionoideae or eeven more preferably is from the tribe Phaseoleae, Cicereae, Genisteae, Fabeae, Dalbergieae or Phaseoleae or any combination thereof.
32. The pelleted animal feed of item 30, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
33. The pelleted animal feed of any of items 30 to 32, wherein the polypeptide of any of items 9 to 10, the composition of any of items 11 to 17, the granule of any of items 23 to 25 or the animal feed additive of item 26 is sprayed onto the pellet.
34. A liquid formulation comprising the polypeptide of any of items 9 to 10 or the composition of any of items 11 to 17.
35. The liquid formulation of item 34, wherein the polypeptide having alpha-galactosidase activity is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.
36. The liquid formulation of any of items 34 to 35, wherein the formulation further comprises 20% to 80% w/w of polyol.
37. The liquid formulation of item 36, wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600 or any combination thereof.
38. The liquid formulation of any of items 34 to 37, wherein the formulation further comprises 0.01% to 2.0% w/w preservative.
39. The liquid formulation of item 38, wherein the preservative is selected from the group consisting of sodium sorbate, potassium sorbate, sodium benzoate and potassion benzoate or any combination thereof.
40. The liquid formulation of any of items 34 to 39 further comprising one or more components selected from the list consisting of:
   one or more enzymes;
   one or more microbes;
   one or more vitamins;
   one or more minerals;
   one or more amino acids;
   one or more phytogenics;
   one or more prebiotics;
   one or more organic acids; and
   one or more other feed ingredients.
41. A method of preparing an animal feed comprising applying the liquid formulation of any of items 34 to 40 onto plant based material.
42. The method of item 41, wherein the liquid formulation is applied via a spray.
43. The method of any of items 41 to 42, wherein the plant based material is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
44. The method of any of items 41 to 43, wherein the plant based material is in pelleted form.
45. A pelleted animal feed prepared using the method of any of items 41 to 44.
46. A method of improving one or more performance parameters of an animal comprising administering to one or more animals one or more polypeptides of any of items 9 to 10, the composition of any of items 11 to 17, the granule of any of items 23 to 25, the animal feed additive of item 26, the animal feed of any of items 27 to 29, the pelleted animal feed of any of items 30 to 33 or 45 or the liquid formulation of any of items 34 to 39.
47. The method of item 46, wherein the performance parameter is selected from the list consisting of body weight gain (BWG), European Production Efficiency Factor (EPEF) and Feed Conversion Ratio (FCR) or any combination thereof.
48. A method for improving the nutritional value of an animal feed, comprising adding to the feed one or more polypeptides of any of items 9 to 10, the composition of any of items 11 to 17, the granule of any of items 23 to 25, the animal feed additive of item 26 or the liquid formulation of any of items 34 to 39.

49. A method for reducing the antinutritional effects of an animal feed, comprising adding to the feed one or more polypeptides of any of items 9 to 10, the composition of any of items 11 to 17, the granule of any of items 23 to 25, the animal feed additive of item 26 or the liquid formulation of any of items 34 to 39.

50. A method of preparing an animal feed, comprising mixing one or more polypeptides of any of items 9 to 10, the composition of any of items 11 to 17, the granule of any of items 23 to 25, the animal feed additive of item 26 or the liquid formulation of any of items 34 to 39 with plant based material.

51. A method of releasing galactose from plant based material, comprising mixing one or more polypeptides of any of items 9 to 10, the composition of any of items 11 to 17, the granule of any of items 23 to 25, the animal feed additive of item 26 or the liquid formulation of any of items 34 to 39 with the plant based material.

52. The methods of any of items 46 to 51, wherein the plant based material is from the taxonomic subclass rosids.

53. The methods of any of items 46 to 51, wherein the plant based material is from the family Fabaceae, preferably the sub-family Papilionoideae.

54. The methods of any of items 46 to 51, wherein the plant based material is from the tribe Phaseoleae, Cicereae, Genisteae, Fabeae, Dalbergieae or Phaseoleae or any combination thereof.

55. The methods of any of items 46 to 51, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

56. Use of the polypeptide of any of items 9 to 10, the composition of any of items 11 to 17, the granule of any of items 23 to 25, the animal feed of any of items 27 to 29, the pelleted animal feed of any of items 30 to 33 or 45 or the liquid formulation of any of items 34 to 39:

in animal feed;
in animal feed additives;
in the preparation of a composition for use in animal feed;
for improving the nutritional value of an animal feed;
for increasing digestibility of the animal feed;
for improving one or more performance parameters in an animal; and/or
for releasing galactose from plant based material of the taxonomic subclass rosids.

57. A polynucleotide encoding the polypeptide of any of items 9 to 10.

58. A nucleic acid construct or expression vector comprising the polynucleotide of item 57 operably linked to one or more control sequences that direct the production of the polypeptide in an expression host.

59. A recombinant host cell comprising the polynucleotide of item 57 operably linked to one or more control sequences that direct the production of the polypeptide.

60. A method of producing the polypeptide of any of items 9 to 10, comprising:
    (a) cultivating a cell, which in its wild-type form produces the polypeptide, under conditions conductive for production of the polypeptide; and
    (b) recovering the polypeptide.

61. A method of producing the polypeptide of any of items 9 to 10, comprising:
    (a) cultivating the recombinant host cell of item 59 under conditions conducive for production of the polypeptide; and
    (b) recovering the polypeptide.

62. A transgenic plant, plant part or plant cell transformed with a polynucleotide encoding the polypeptide of any of items 9 to 10.

63. A whole broth formulation or cell culture composition comprising a polypeptide of any of items 9 to 10.

The present invention is further described by the following examples that should not be construed as limiting the scope of the invention.

EXAMPLES

Strains

The alpha-galactosidases were derived from strains isolated from environmental samples by standard microbiological isolation techniques. Strains were identified and taxonomy was assigned based on DNA sequencing of the 16S ribosomal genes (Table 2).

TABLE 2

Isolation of strains

| Strain | Source | Country | Year | SEQ ID NO of gene | SEQ ID NO of polypeptide |
| --- | --- | --- | --- | --- | --- |
| Bacillus deramificans | Soil sample (humus) | Denmark | May 2002 | 1 | 2 |
| Bacillus acidopullulyticus[1] | Soil sample | Rio de Janeiro, Brazil. | September 1980 | 4 | 5 |
| Anoxybacillus bogrovensis | Soil sample | Bulgaria | May 2003 | 7 | 8 |
| Aspergillus sydowii | Environmental sample | Denmark | January 2013 | 10 | 11 |
| Bacillus sp-19140 | Soil sample | Australia | 1990 | 13 | 14 |
| Aspergillus puniceus | Environmental sample | Denmark | December 2010 | 17 | 18 |

[1]Deposited as NCIB 11610

Chromosomal DNA isolated from pure cultures of the individual strains with the DNeasy Blood & Tissue Kit from Qiagen (Hilden, Germany) was subjected to full genome sequencing using Illumina technology. Genome sequencing, the subsequent assembly of reads and the gene discovery (i.e. annotation of gene functions) is known to the person skilled in the art and the service can be purchased commercially.

The genome sequence was analyzed for alpha-galactosidases from the CAZY database family GH36 (Lombard et al. The Carbohydrate-active enzymes database CAZy. Nucleic Acids Res 2013, 42:D490-D495.) This analysis identified three gene encoding putative alpha-galactosidases with the nucleotide sequences given in SEQ ID NO: 1, 4, 7, 10 and 13.

Alpha-Galactosidase Assay

Alpha-galactosidase activity can be determined using 4-nitrophenyl α-D-galactopyranoside (product code O-PNPBGAL, available from Megazyme International, Bray, Co. Wicklow, Ireland) as follows.

The enzyme was diluted using 100 mM MES (Sigma) buffer pH 7.0±0.05 in 2-fold dilutions and then the 4-nitrophenyl α-D-galactopyranoside (1 mg/ml in 100 mM MES buffer pH 7.0±0.05, prepared immediately before use) was added in the solution containing the enzyme. The respective galactosidase activity was followed directly in the buffer by measuring the absorbance of released pNP (para-nitro-phenol) at 405 nm for 5 minutes as function of time at room temperature (typically 23° C.). A concentration of 1 mg/mL of enzyme is a good starting point; it will however depend from enzyme to enzyme and their specific activity.

The activity is calculated as the slope of a plot of absorbance versus time (units: mOD/min) using the 1-5 minute time window and the 0-2 absorbance window. The activity can then be converted to specific activity by dividing the activity for the concentration of the enzyme (units: (mOD/min)/(mg/ml)).

Galactose SBM Assay

Introduction

The concentration of galactose monosaccharides in a solution was measured spectrophotometrically after enzymatic hydrolysis of a galactose-rich substrate; soybean meal.

Summarizing, the enzyme(s) were incubated in a 10 w/v % slurry of soybean meal at pH 6.5±0.05 for 2 hours at 40±2° C. The supernatant was then analyzed in an assay based on the Raffinose/Galactose kit from Megazyme (product name K-RAFGA). First α-D-galactose in the supernatant was converted to β-D-galactose with the enzyme galactose mutarotase. Then β-D-galactose was oxidised by NAD+ to D-galactonic acid in the presence of β-galactose dehydrogenase. The amount of NADH formed in this reaction was stoichiometric with the amount of D-Galactose in the supernatant. NADH concentration was then measured by the increase in absorbance at 340 nm.

Soybean Meal Slurry

A 10 w/v % slurry of soybean meal was prepared from soybean meal milled to a 0.5 mm particle size and 0.1 M citric acid-phosphate buffer, pH 6.5±0.05.

0.1 M citric acid-phosphate buffer, pH 6.5±0.05 was heated to a temperature of approximately 40° C. while stirring. The preheated buffer was then transferred to the soybean meal. The resulting slurry was stirred while being heated (temperature was not monitored at this point— heating was only applied to ensure that temperature would not decrease too much while the slurry stirred). The slurry was then transferred with a pre-wetted wide-bore pipette to the vessel in which it should be incubated. The slurry was pipetted from an approximately central point in the mix. The time elapsed from the mixing of the slurry until transfer to the last incubation vessel was, at most, 15 minutes. Stirring speed was adjusted in such a way that particles were evenly distributed in the slurry.

Dilution of Enzymes

The enzymes were diluted to their desired concentrations in ultrapure water. The concentration to which the enzymes were diluted to was based on the prior concentration of the enzyme in mg enzyme protein per mL (mg EP/mL) and the mass (kg) of dry matter (soybean meal) in each incubation vessel.

$$V_{enzyme}(\text{mL}) = \frac{c_{enzyme}\left(\text{mg}\frac{EP}{\text{mL}}\right)}{m_{SBM}(\text{kg})}$$

D-(+)-Galactose Standards

A standard curve was prepared from D-(+)-galactose and ultrapure water. A D-(+)-galactose stock was prepared by dissolving D-(+)-galactose in ultrapure water to a final concentration of 250 mg galactose per mL. The stock solution was diluted in a two-fold dilution row to obtain six standards with concentrations of 250, 125, 62.5, 31.25, 15.625 and 7.813 mg galactose per mL.

Incubation of α-Galactosidases on Soybean Meal

The incubation vessels with the 10 w/v % slurry of soybean meal were heated to a stable temperature of 40±2° C. while stirring. When a stable temperature had been achieved, the six D-(+)-galactose standards were added to the incubation vessels to in-vessel concentrations of 5, 2.5, 1.25, 0.625, 0.313 and 0.157 mg galactose per mL incubation volume. Each standard was incubated in duplicates.

The diluted enzymes were then added to their respective incubation vessels in the volumes required to reach their desired concentrations (in mg EP/kg soybean meal). Each enzyme treatment was incubated in triplicates.

Additionally, two times three incubation vessels were included without standards or enzyme treatments as blank treatments to obtain the baseline galactose concentration in the soybean meal slurry.

The incubation vessels were incubated at 40±2° C., while stirring for 2 hours. After incubation the vessels were centrifuged at 1500 g at 5° C. for 15 minutes.

Determination of Galactose Concentration

The supernatants in the now centrifuged incubation vessels were then analyzed in an assay based on the Raffinose/Galactose kit from Megazyme (product name K-RAFGA). Three reagents from the K-RAFGA kit was used in the assay: Assay Buffer (supplied and ready in Bottle 1 in the kit), β-NAD reagent (supplied in Bottle 2 in the kit, prepared as described in the kit prior to use) and GalDH+GalM solution (supplied in Bottle 3 in the kit, diluted 1:1 in ultrapure water prior to use). All steps described in the following were carried out using an Eppendorf 5075 automated pipetting system.

First the supernatants from the centrifuged incubation vessels were diluted 10 times in 0.1 M citric acid-phosphate buffer, pH 6.5±0.05 (1 part supernatant plus 9 parts 0.1 M citric acid-phosphate buffer, pH 6.5±0.05).

69 μL of each diluted supernatant was then transferred to a new vessel and 34 μL of ultrapure water was added to the diluted supernatants (which will be referred to as assay samples from here on out). Then 69 μL Assay Buffer was added to the assay samples followed by dilution in 687 μL ultrapure water. 34 μL β-NAD reagent was added to the assay samples, followed by addition of 14 μL GalDH+GalM solution and vigorous mixing.

262 μL of each assay sample was then transferred to a 96 well micro titer plate. Absorbance in each well of the 96 well micro titer plate was measured at 340 nm at 40±2° C. for a duration of 20 minutes or until absorbance in each well had reached a stable level. When a stable absorbance had been reached this stable absorbance was used in later calculations. Calculation of Galactose Concentration Absorbance of the assay samples from the galactose standards in the incubation vessels were used as a standard curve (6 standards, 5, 2.5, 1.25, 0.625, 0.313 and 0.157 mg galactose per mL incubation volume, n=2 per standard). An equation for the galactose standard curve was calculated in excel, where y is OD340 and x is galactose concentration in mg galactose per mL incubation volume:

$$OD_{340} = a * c_{gal}\left(\frac{mg}{mL}\right) + b$$

Galactose concentration in mg galactose per mL incubation volume for each sample was then given by:

$$c_{gal}\left(\frac{mg}{mL}\right) = \frac{OD_{340} - b}{a}$$

Galactose concentrations were then calculated on a dry-matter basis (g galactose per kg soybean meal) and are reported in the examples below:

$$c_{gal}\left(\frac{g}{kg}SBM\right) = \frac{c_{gal}\left(\frac{mg}{mL}\right) * V_{sample}(mL)}{m_{SBM}(g)}$$

Example 1: Cloning of GH36 Alpha-Galactosidases (SEQ ID NO: 1, 4, 7 and 13)

The genes encoding the alpha-galactosidases were amplified by PCR and fused with regulatory elements, affinity purification tag and homology regions for recombination into the *B. subtilis* genome. The linear integration construct was a SOE-PCR fusion product (Horton, R. M., Hunt, H. D., Ho, S. N., Pullen, J. K. and Pease, L. R. (1989) *Engineering hybrid genes without the use of restriction enzymes, gene splicing by overlap extension*, Gene 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

Furthermore the expression construct results in the addition of a carboxy-terminal poly histidine tail consisting of 6 consecutive histidine residues.

The SOE-PCR product was transformed into *Bacillus subtilis* and integrated in the chromosome by homologous recombination into the pectate lyase locus. Subsequently one recombinant *Bacillus subtilis* clone containing the respective alpha-galactosidase expression construct was selected and was cultivated on a rotary shaking table in 500 ml baffled Erlenmeyer flasks each containing 100 ml rich starch based media. After 3-5 days cultivation time at 30° C. to 37° C., enzyme containing supernatants were harvested by centrifugation and the enzymes were purified by immobilized metal affinity chromatography.

Example 2: Purification of GH36 Alpha-Galactosidases (SEQ ID NO: 3, 6, 9 and 15)

The pH of the supernatant from experiment 1 was adjusted to pH 8, filtrated through a 0.2 µM filter, and then applied to a 5 ml HisTrap™ excel column (GE Healthcare Life Sciences, Pittsburgh, USA). Prior to loading, the column had been equilibrated in 5 column volumes (CV) of 50 mM Tris/HCl pH 8. In order to remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column (GE Healthcare Life Sciences, Pittsburgh, USA)., equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Example 3: Cloning of GH36 Alpha-Galactosidase (SEQ ID NO: 10)

The alpha-galactosidase with nucleotide sequence SEQ ID NO: 10 and the peptide translation of the protein shown in SEQ ID NO: 11 was PCR amplified from genomic DNA isolated from *Aspergillus sydowii* and cloned into the expression vector pDAu222 as described in WO 2013024021 using BamHI and XhoI restriction sites.

The sequence of the alpha-galactosidase encoding gene cloned in the expression vector was confirmed and the expression construct was transformed into the *Aspergillus oryzae* strain MT3568 (WO 11/057140) to produce the secreted mature peptide with protein sequence SEQ ID NO: 12. Transformants were selected on acetamide during regeneration from protoplasts and subsequently re-isolated under selection (Christensen et al., 1988, *Biotechnology* 6, 1419-1422 and WO 04/032648).

For production of the recombinant alpha-galactosidase, a single *Aspergillus transformant* was cultured in two 500 ml baffled flasks each containing 150 ml of DAP-4C-1 medium (WO 12/103350). The cultures were shaken on a rotary table at 100 RPM at 30° C. for 4 days. The culture broth subsequently was separated from cellular material by passage through a 0.22 um filter and purified as described in Example 4.

Example 4: Purification of GH36 Alpha-Galactosidase (SEQ ID NO: 12)

The broth was diluted 50:50 with 3.6M ammonium sulphate, stirred for 30 minutes and then filtered through a 0.2 µm filter. The sample was applied to a 5 ml HiTrap™ Phenyl (FF) column (GE Healthcare, Piscataway, N.J., USA) on an Äkta purifier. Prior to loading, the column had been equilibrated in 5 column volumes (CV) of 50 mM HEPES+1.8M ammonium sulphate pH 7. In order to remove unbound material, the column was washed with 5 CV of 50 mM HEPES+1.8M ammonium sulphate pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

Example 5: Hydrolysis of Soybean Meal (SBM) with GH36 Alpha-Galactosidases

The release of galactose from soybean meal of three GH36 alpha-galactosidases of the invention (SEQ ID NO: 3, 6 and 9) and a prior art GH36 alpha-galactosidases (SEQ ID NO: 16) were determined using the Galactose SBM Assay and the results are presented in tables 3 and 4 below.

TABLE 3

Release of galactose from soybean meal using a GH36 alpha-galactosidase (SEQ ID NO: 3, 6, 9 and 16)

| GH36 alpha-galactosidase | Conc. [mg EP/kg] | Mean Galactose Release (g gal/kg SBM) | Significance[1] |
|---|---|---|---|
| SEQ ID NO: 3 | 20 | 26.0 | A |
| SEQ ID NO: 6 | 20 | 24.1 | B |
| SEQ ID NO: 9 | 20 | 20.3 | C |
| SEQ ID NO: 16 | 20 | 18.2 | D |
| Blank | — | −0.4 | E |

[1]Means not sharing a common letter are significantly different ($p < 0.05$).

TABLE 4

Release of galactose from soybean meal using a GH36 alpha-galactosidase (SEQ ID NO: 3, 6, 9 and 16)

| GH36 alpha-galactosidase | Conc. [mg EP/kg] | Mean Galactose Release (g gal/kg SBM) | Significance[1] |
|---|---|---|---|
| SEQ ID NO: 3 | 20 | 25.9 | A |
| SEQ ID NO: 6 | 20 | 25.1 | A |
| SEQ ID NO: 9 | 20 | 20.6 | B |
| SEQ ID NO: 16 | 20 | 18.5 | BC |
| Blank | — | −0.6 | D |

[1]Means not sharing a common letter are significantly different ($p < 0.05$).

The results show that the alpha-galactosidases of the invention (SEQ ID NO: 3, 6 and 9) are significantly more active in releasing galactose from soybean meal than the prior art sequence (SEQ ID NO: 16).

Example 6: Hydrolysis of Soybean Meal (SBM) with GH36 Alpha-Galactosidases

The release of galactose from soybean meal of two GH36 alpha-galactosidases of the invention (SEQ ID NO: 3 and 12) and a prior art GH36 alpha-galactosidases (SEQ ID NO: 16) were determined using the Galactose SBM Assay and the results are presented in tables 5 and 6 below.

TABLE 5

Release of galactose from soybean meal using a GH36 alpha-galactosidase (SEQ ID NO: 3, 12 and 16)

| GH36 alpha-galactosidase | Conc. [mg EP/kg] | Mean Galactose Release (g gal/kg SBM) | Significance[1] |
|---|---|---|---|
| SEQ ID NO: 3 | 20 | 24.4 | A |
| SEQ ID NO: 12 | 20 | 20.6 | B |
| SEQ ID NO: 16 | 20 | 16.1 | C |
| Blank | — | 0.7 | D |

[1]Means not sharing a common letter are significantly different ($p < 0.05$).

TABLE 6

Release of galactose from soybean meal using a GH36 alpha-galactosidase (SEQ ID NO: 3, 12 and 16)

| GH36 alpha-galactosidase | Conc. [mg EP/kg] | Mean Galactose Release (g gal/kg SBM) | Significance[1] |
|---|---|---|---|
| SEQ ID NO: 3 | 20 | 23.3 | A |
| SEQ ID NO: 12 | 20 | 19.4 | B |
| SEQ ID NO: 16 | 20 | 16.9 | C |
| Blank | — | −0.0 | D |

[1]Means not sharing a common letter are significantly different ($p < 0.05$).

The results show that the alpha-galactosidases of the invention (SEQ ID NO: 3 and 12) are significantly more active in releasing galactose from soybean meal than the prior art sequence (SEQ ID NO: 16).

Example 7: Hydrolysis of Soybean Meal (SBM) with GH36 Alpha-Galactosidases

The release of galactose from soybean meal of four GH36 alpha-galactosidases of the invention (SEQ ID NO: 3, 6, 9 and 12) and a prior art GH36 alpha-galactosidases (SEQ ID NO: 16) were determined using the Galactose SBM Assay and the results are presented in table 7 below.

TABLE 7

Release of galactose from soybean meal using a GH36 alpha-galactosidase (SEQ ID NO: 3, 6, 9, 12 and 16)

| GH36 alpha-galactosidase | Conc. [mg EP/kg] | Mean Galactose Release (g gal/kg SBM) | Significance[1] |
|---|---|---|---|
| SEQ ID NO: 3 | 20 | 24.4 | A |
| SEQ ID NO: 6 | 20 | 21.5 | B |
| SEQ ID NO: 12 | 20 | 20.5 | B |
| SEQ ID NO: 9 | 20 | 19.1 | C |
| SEQ ID NO: 16 | 20 | 18.1 | C |
| Blank | — | −0.1 | D |

[1]Means not sharing a common letter are significantly different ($p < 0.05$).

The results show that the alpha-galactosidases of the invention (SEQ ID NO: 3, 6, 9 and 12) all numerically release more galactose from soybean meal than the prior art sequence (SEQ ID NO: 16) and alpha-galactosidases SEQ ID NO: 3, 6 and 12 release a significantly higher amount of galactose from soybean meal than the prior art sequence.

Example 8: Hydrolysis of Soybean Meal (SBM) with GH36 Alpha-Galactosidases

The release of galactose from soybean meal of two GH36 alpha-galactosidases of the invention (SEQ ID NO: 3 and 15) and a prior art GH36 alpha-galactosidases (SEQ ID NO: 16) were determined using the Galactose SBM Assay and the results are presented in table 8 below.

TABLE 8

Release of galactose from soybean meal using a GH36 alpha-galactosidase (SEQ ID NO: 3, 15 and 16)

| GH36 alpha-galactosidase | Conc. [mg EP/kg] | Mean Galactose Release (g gal/kg SBM) | Significance[1] |
|---|---|---|---|
| SEQ ID NO: 15 | 20 | 25.4 | A |
| SEQ ID NO: 3 | 20 | 22.3 | A |

TABLE 8-continued

Release of galactose from soybean meal using a GH36 alpha-galactosidase (SEQ ID NO: 3, 15 and 16)

| GH36 alpha-galactosidase | Conc. [mg EP/kg] | Mean Galactose Release (g gal/kg SBM) | Significance[1] |
|---|---|---|---|
| SEQ ID NO: 16 | 20 | 15.9 | B |
| Blank | — | −1.2 | C |

[1]Means not sharing a common letter are significantly different (p < 0.05).

The results show that the alpha-galactosidases of the invention (SEQ ID NO: 3 and 15) are significantly more active in releasing galactose from soybean meal than the prior art sequence (SEQ ID NO: 16).

Example 9: Animal Feed and Animal Feed Additives Comprising an Alpha-Galactosidase Animal Feed Additive A premix formulation of an alpha-galactosidase of the invention (e.g. SEQ ID NO: 2, 3, 5, 6, 8, 9, 11, 12, 14, 15, 18 or 19) containing 0.01 g to 10 g enzyme protein per kilo of premix (optionally formulated as a coated granule) is added to the following premix:

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Animal Feed

This is an example of an animal feed (broiler feed) comprising the animal feed additive as described above:
62.55% Maize
33.8% Soybean meal (50% crude protein)
1.0% Soybean oil
0.2% DL-Methionine
0.22% DCP (dicalcium phosphate)
0.76% CaCO$_3$ (calcium carbonate)
0.32% Sand
0.15% NaCl (sodium chloride)
1% of the above Premix The ingredients are mixed, and the feed is pelleted at the desired temperature, e.g. 60, 65, 75, 80, 85, 90 or even 95° C.

Liquid Formulation

A liquid formulation of an alpha-galactosidase of the invention (e.g. SEQ ID NO: 2, 3, 5, 6, 8, 9, 11, 12, 14, 15, 18 or 19) comprises 0.1% to 10 w/w enzyme protein, 40-60% glycerol, 0.1 to 0.5% sodium benzoate and water. The liquid formulation is sprayed onto the pelleted animal feed described above (in this case the animal feed additive would not include the alpha-galactosidase of the invention present).

Example 10: Cloning of GH36 Alpha-Galactosidase (SEQ ID NO: 17)

The alpha-galactosidase with nucleotide sequence SEQ ID NO: 17 and the peptide translation of the protein shown in SEQ ID NO: 18 was PCR amplified from genomic DNA isolated from *Aspergillus sydowii* and cloned into the expression vector pDAu222 as described in WO 2013024021 using BamHI and XhoI restriction sites.

The sequence of the alpha-galactosidase encoding gene cloned in the expression vector was confirmed and the expression construct was transformed into the *Aspergillus oryzae* strain MT3568 (WO 11/057140) to produce the secreted mature peptide with protein sequence SEQ ID NO: 18. Transformants were selected on acetamide during regeneration from protoplasts and subsequently re-isolated under selection (Christensen et al., 1988, *Biotechnology* 6, 1419-1422 and WO 04/032648).

For production of the recombinant alpha-galactosidase, a single *Aspergillus transformant* was cultured in two 500 ml baffled flasks each containing 150 ml of DAP-4C-1 medium (WO 12/103350). The cultures were shaken on a rotary table at 100 RPM at 30° C. for 4 days. The culture broth subsequently was separated from cellular material by passage through a 0.22 um filter and purified as described in Example 11.

Example 11: Purification of GH36 Alpha-Galactosidase (SEQ ID NO: 19)

The broth was diluted 50:50 with 1.8M ammonium sulphate, stirred for 30 minutes and then filtered through a 0.2 μm filter. The sample was applied to a 5 ml HiTrap™ Phenyl (FF) column (GE Healthcare, Piscataway, N.J., USA) on an Äkta Explorer. Prior to loading, the column had been equilibrated in 5 column volumes (CV) of 50 mM HEPES+1.8M ammonium sulphate pH 7. In order to remove unbound material, the column was washed with 5 CV of 50 mM HEPES+1.8M ammonium sulphate pH 7. The target protein was eluted from the column into a 10 ml loop using 50 mM HEPES+20% ethanol pH 7. From the loop, the sample was loaded onto a desalting column (HiPrep™ 26/10 Desalting), which had been equilibrated with 3CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

Example 12: Hydrolysis of Soybean Meal (SBM) with GH36 Alpha-Galactosidases

The release of galactose from soybean meal of two GH36 alpha-galactosidases of the invention (SEQ ID NO: 3 and 19) and a prior art GH36 alpha-galactosidases (SEQ ID NO: 16) were determined using the Galactose SBM Assay and the results are presented in table 9 below.

TABLE 9

Release of galactose from soybean meal using a GH36 alpha-galactosidase (SEQ ID NO: 3, 15 and 16)

| GH36 alpha-galactosidase | Conc. [mg EP/kg] | Mean Galactose Release (g gal/kg SBM) | Significance[1] |
|---|---|---|---|
| SEQ ID NO: 19 | 20 | 23.1 | B |
| SEQ ID NO: 3 | 20 | 25.2 | A |
| SEQ ID NO: 16 | 20 | 19.2 | C |
| Blank | — | 1.1 | D |

[1]Means not sharing a common letter are significantly different ($p < 0.05$).

The results show that the alpha-galactosidases of the invention (SEQ ID NO: 3 and 19) are significantly more active in releasing galactose from soybean meal than the prior art sequence (SEQ ID NO: 16).

Example 13: Hydrolysis of Soybean Meal (SBM) with GH36 Alpha-Galactosidases

The release of galactose from soybean meal of a GH36 alpha-galactosidase of the invention (SEQ ID NO: 3) was compared to the prior art GH36 alpha-galactosidase SEQ ID NO: 16 and a close analogue to the prior art GH36 alpha-galactosidase disclosed as SEQ ID NO: 597 in WO2009/108941 (AXR38459). SEQ ID NO: 20 is 97.3% identical to AXR38459. The release of galactose from soybean meal was determined using the Galactose SBM Assay and the results are presented in table 10 below.

TABLE 10

Release of galactose from soybean meal using a GH36 alpha-galactosidase (SEQ ID NO: 3, 16 and 20)

| GH36 alpha-galactosidase | Conc. [mg EP/kg] | Mean Galactose Release (g gal/kg SBM) | Significance[1] |
|---|---|---|---|
| SEQ ID NO: 3 | 20 | 25.7 | A |
| SEQ ID NO: 16 | 20 | 18.7 | B |
| SEQ ID NO: 20 | 20 | 4.0 | C |
| Blank | — | −0.3 | D |

[1]Means not sharing a common letter are significantly different ($p < 0.05$).

The results show that the close analogue to prior art sequence AXR38459 (i.e. SEQ ID NO: 20) is not very effective at releasing galactose from soybean meal compared to the other prior art GH36 alpha-galactosidase SEQ ID NO: 16 or a GH36 alpha-galactosidase of the invention (SEQ ID NO: 3).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method of releasing galactose from plant-based material, comprising treating the plant-based material with a GH36 polypeptide having alpha-galactosidase activity, wherein the GH36 polypeptide having alpha-galactosidase activity has at least 80% sequence identity to the polypeptide of SEQ ID NO: 2.

2. The method of claim 1, wherein the GH36 polypeptide having alpha-galactosidase activity has at least 85% sequence identity to the polypeptide of SEQ ID NO: 2.

3. The method of claim 1, wherein the GH36 polypeptide having alpha-galactosidase activity has at least 95% sequence identity to the polypeptide of SEQ ID NO: 2.

4. The method of claim 1, wherein the GH36 polypeptide having alpha-galactosidase activity comprises an N-terminal and/or C-terminal His-tag and/or HQ-tag.

5. The method of claim 1, wherein the GH36 polypeptide having alpha-galactosidase activity comprises an N-terminal and/or C-terminal extension of up to 10 amino acids.

6. The method of claim 1, wherein the GH36 polypeptide having alpha-galactosidase activity is a fragment of the polypeptide of SEQ ID NO:2 which comprises alpha-galactosidase activity.

7. The method of claim 1, wherein the plant-based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

8. The method of claim 1, wherein the GH36 polypeptide releases at least 19 g galactose per kg soybean meal when performed under the reaction conditions 20 mg polypeptide per kg soybean meal in 10% w/v 0.1M citric acid-phosphate buffer pH 6.5 incubating at 40° C. for 2 hours.

* * * * *

UNITED STATES PATENT AND TRADEMARK OFFICE
CERTIFICATE OF CORRECTION

PATENT NO. : 10,808,268 B2
APPLICATION NO. : 16/094368
DATED : October 20, 2020
INVENTOR(S) : Lone Carstensen et al.

It is certified that error appears in the above-identified patent and that said Letters Patent is hereby corrected as shown below:

In the Claims

Please amend Claim 1 at Column 173, Lines 40-45 as follows:
1. A method of releasing galactose from plant-based material, comprising treating the plant-based material with a GH36 polypeptide having alpha-galactosidase activity, wherein the GH36 polypeptide having alpha-galactosidase activity has at least 90% sequence identity to the polypeptide of SEQ ID NO: 2.

Please amend Claim 2 at Column 173, Lines 46-48 as follows:
2. The method of claim 1, wherein the GH36 polypeptide comprises the polypeptide sequence of SEQ ID NO: 2.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 20

<210> SEQ ID NO 1
<211> LENGTH: 2187
<212> TYPE: DNA
<213> ORGANISM: Bacillus deramificans
<220> FEATURE:
<221> NAME/KEY: CDS
<222> LOCATION: (1)..(2184)
<220> FEATURE:
<221> NAME/KEY: mat_peptide
<222> LOCATION: (1)..(2184)

<400> SEQUENCE: 1 atg ggc atc tca tat gat tcc gag aat cgc att ttt cat cta caa ggt      48
Met Gly Ile Ser Tyr Asp Ser Glu Asn Arg Ile Phe His Leu Gln Gly
1               5                   10                  15 aaa ggt acc agt tat ctc atg cag gta tta aaa gac ggt tat ctg gct      96
Lys Gly Thr Ser Tyr Leu Met Gln Val Leu Lys Asp Gly Tyr Leu Ala
                20                  25                  30 cat ctt tac tgg ggg aga ggg gtt cgt caa tat agt gga ggg att cca     144
His Leu Tyr Trp Gly Arg Gly Val Arg Gln Tyr Ser Gly Gly Ile Pro
            35                  40                  45 ata acg ttt ttt gat cgc ggt ttt tca cca aac cct gac cct tct gac     192
Ile Thr Phe Phe Asp Arg Gly Phe Ser Pro Asn Pro Asp Pro Ser Asp
        50                  55                  60 cga acc ttc tct ctt gat acg ctg ccg caa gaa tac cct gct tat ggg     240
Arg Thr Phe Ser Leu Asp Thr Leu Pro Gln Glu Tyr Pro Ala Tyr Gly
65                  70                  75                  80 aac acg gat ttt cgc aca ccg gct tat caa gtt cag tta gag aat ggt     288
Asn Thr Asp Phe Arg Thr Pro Ala Tyr Gln Val Gln Leu Glu Asn Gly
                85                  90                  95 tcc acc att tca gac ctc cgc tat aaa gga cac gcc ata tat aaa ggg     336
Ser Thr Ile Ser Asp Leu Arg Tyr Lys Gly His Ala Ile Tyr Lys Gly
```

```
            100              105              110
aag cct aag tta gaa gga ttg cca gcg gtg tat gtt gaa gac gac cgt    384
Lys Pro Lys Leu Glu Gly Leu Pro Ala Val Tyr Val Glu Asp Asp Arg
        115              120              125 gaa gcc gaa aca tta gaa ata aca ctg gaa gat tcg cta att ggt ttg    432
Glu Ala Glu Thr Leu Glu Ile Thr Leu Glu Asp Ser Leu Ile Gly Leu
    130              135              140 gaa atg gtc tta gtt tat aca gta ttt gaa aac ttt agt gct atc acg    480
Glu Met Val Leu Val Tyr Thr Val Phe Glu Asn Phe Ser Ala Ile Thr
145             150              155              160 cgt tca gtt cgt ttt gag aat aaa ggc acc cag gac tta aaa atc ctt    528
Arg Ser Val Arg Phe Glu Asn Lys Gly Thr Gln Asp Leu Lys Ile Leu
            165              170              175 cga gca tta agc gca aat att gat ttt aga gat gat gat ttt gag tta    576
Arg Ala Leu Ser Ala Asn Ile Asp Phe Arg Asp Asp Asp Phe Glu Leu
        180              185              190 atc act tta tac ggt tcg cat att aat gag cga aat ata gca agg cgt    624
Ile Thr Leu Tyr Gly Ser His Ile Asn Glu Arg Asn Ile Ala Arg Arg
    195              200              205 cct att caa cct gga act caa tct att gaa agc cgg cgc gga gcg agc    672
Pro Ile Gln Pro Gly Thr Gln Ser Ile Glu Ser Arg Arg Gly Ala Ser
210             215              220 agc cac cag cag aat ccg ttt ctt gct ttg cta aga ccg aat gca aca    720
Ser His Gln Gln Asn Pro Phe Leu Ala Leu Leu Arg Pro Asn Ala Thr
225             230              235              240 gaa gac caa gga gat gta tac ggg ctg aat ctt gtc tac agc ggg aac    768
Glu Asp Gln Gly Asp Val Tyr Gly Leu Asn Leu Val Tyr Ser Gly Asn
            245              250              255 ttt ctt ggg caa gtg gaa gtg aac cag ttt caa aca aca aga gta tcc    816
Phe Leu Gly Gln Val Glu Val Asn Gln Phe Gln Thr Thr Arg Val Ser
        260              265              270 att ggc att aat cct ttt gat ttt tcg tgg ctt ttg cag ccc ggt gaa    864
Ile Gly Ile Asn Pro Phe Asp Phe Ser Trp Leu Leu Gln Pro Gly Glu
    275              280              285 aac ttt cag gcg cca gaa gca gtc atg gtc tac tcc tca gaa gga tta    912
Asn Phe Gln Ala Pro Glu Ala Val Met Val Tyr Ser Ser Glu Gly Leu
290             295              300 gcg ggt atg tcg caa acc tat cat gag ctt tat cga aca cgc ctt agc    960
Ala Gly Met Ser Gln Thr Tyr His Glu Leu Tyr Arg Thr Arg Leu Ser
305             310              315              320 cgc ggt gag cat cga gac aag gtt cgt cct att tta atc aat aat tgg   1008
Arg Gly Glu His Arg Asp Lys Val Arg Pro Ile Leu Ile Asn Asn Trp
            325              330              335 gag gct act tac ttc gac ttt aat gcg gat aaa att gtt gag att gct   1056
Glu Ala Thr Tyr Phe Asp Phe Asn Ala Asp Lys Ile Val Glu Ile Ala
        340              345              350 caa gtg gga aaa gaa cta ggc atg gag ctt atg gtg cta gac gat gga   1104
Gln Val Gly Lys Glu Leu Gly Met Glu Leu Met Val Leu Asp Asp Gly
    355              360              365 tgg ttt gga aaa cga gat gat gac ttt acc tca tta gga gat tgg gtg   1152
Trp Phe Gly Lys Arg Asp Asp Asp Phe Thr Ser Leu Gly Asp Trp Val
370             375              380 gtt gat aaa cga aaa ctg cct cat ggt tta act gat ctt gca gag cgt   1200
Val Asp Lys Arg Lys Leu Pro His Gly Leu Thr Asp Leu Ala Glu Arg
385             390              395              400 gtt cgt tca tta gga atg gag ttt ggt tta tgg ttt gaa ccg gaa atg   1248
Val Arg Ser Leu Gly Met Glu Phe Gly Leu Trp Phe Glu Pro Glu Met
            405              410              415 gtt tca atg gag agt gat ctg tat aaa agg cac ccg gat tgg tgt ctt   1296
```

```
                Val Ser Met Glu Ser Asp Leu Tyr Lys Arg His Pro Asp Trp Cys Leu
                            420                 425                 430 cat gtg ccg aat cgt cca aaa agt gag ggg cgc aat caa ctc atc ctt     1344
His Val Pro Asn Arg Pro Lys Ser Glu Gly Arg Asn Gln Leu Ile Leu
            435                 440                 445 gat tta tcg cga caa gaa gtt tgt gac tat gtc att gag tca gta tcc     1392
Asp Leu Ser Arg Gln Glu Val Cys Asp Tyr Val Ile Glu Ser Val Ser
450                 455                 460 agt att cta tca act gtt cca att agt tat gtg aag tgg gat atg aac     1440
Ser Ile Leu Ser Thr Val Pro Ile Ser Tyr Val Lys Trp Asp Met Asn
465                 470                 475                 480 cgt cat atg act gaa atc gga tcc gct gat ctg ctt cca gag aga caa     1488
Arg His Met Thr Glu Ile Gly Ser Ala Asp Leu Leu Pro Glu Arg Gln
            485                 490                 495 agg gaa aca gcg cat cgt tat atg ctg gga ctt tac tat gtt cta gaa     1536
Arg Glu Thr Ala His Arg Tyr Met Leu Gly Leu Tyr Tyr Val Leu Glu
            500                 505                 510 acg att gtt act cgg ttt cca cat gtc ttg ttt gaa agc tgc tct gga     1584
Thr Ile Val Thr Arg Phe Pro His Val Leu Phe Glu Ser Cys Ser Gly
            515                 520                 525 ggc ggc ggc cgt ttt gat cca gga atg ctc tat tac atg cca caa gta     1632
Gly Gly Gly Arg Phe Asp Pro Gly Met Leu Tyr Tyr Met Pro Gln Val
530                 535                 540 tgg acg agt gat aac acc gat gcc atc agc cgt tta aaa att caa tac     1680
Trp Thr Ser Asp Asn Thr Asp Ala Ile Ser Arg Leu Lys Ile Gln Tyr
545                 550                 555                 560 ggg acg agc ctt gtt tac cct ata agt tca atg ggt tca cat gtg tcg     1728
Gly Thr Ser Leu Val Tyr Pro Ile Ser Ser Met Gly Ser His Val Ser
                565                 570                 575 gcg gtt ccg aac cat caa gta gga aga gta aca ccg ctc gat att cgc     1776
Ala Val Pro Asn His Gln Val Gly Arg Val Thr Pro Leu Asp Ile Arg
            580                 585                 590 gga cat gct gcg atg tcg ggt aat ttg ggt tat gag ctc gat tta acc     1824
Gly His Ala Ala Met Ser Gly Asn Leu Gly Tyr Glu Leu Asp Leu Thr
            595                 600                 605 aag ctg tcc gac caa gaa aaa gaa gaa gtc aaa ctg cag att gcg cag     1872
Lys Leu Ser Asp Gln Glu Lys Glu Glu Val Lys Leu Gln Ile Ala Gln
610                 615                 620 tat aaa gaa atc cgt caa ctc gta caa ttt ggc tcc ttt tat cgg ttg     1920
Tyr Lys Glu Ile Arg Gln Leu Val Gln Phe Gly Ser Phe Tyr Arg Leu
625                 630                 635                 640 ctc agt ccg ttt gag ggg aat gag aca gct tgg gtc ttt gta tca tct     1968
Leu Ser Pro Phe Glu Gly Asn Glu Thr Ala Trp Val Phe Val Ser Ser
                645                 650                 655 gat caa aag gaa tgc ctt ttc ggt tat ttc aga gtc ctc tcc caa cca     2016
Asp Gln Lys Glu Cys Leu Phe Gly Tyr Phe Arg Val Leu Ser Gln Pro
            660                 665                 670 aat gca cct act aaa atc atc aaa tta aaa ggg cta aat ctg ggt gag     2064
Asn Ala Pro Thr Lys Ile Ile Lys Leu Lys Gly Leu Asn Leu Gly Glu
            675                 680                 685 cgc tat aaa aaa acg gga tcc gat gag tcg ttt ttt ggg gat gaa ctc     2112
Arg Tyr Lys Lys Thr Gly Ser Asp Glu Ser Phe Phe Gly Asp Glu Leu
            690                 695                 700 atg tat tta ggc att aat atc cct gaa cta aag gga gat ttc caa agt     2160
Met Tyr Leu Gly Ile Asn Ile Pro Glu Leu Lys Gly Asp Phe Gln Ser
705                 710                 715                 720 gtg ttt tgg cat ttc gaa gcg gaa taa                                  2187
Val Phe Trp His Phe Glu Ala Glu
                725
```

<210> SEQ ID NO 2
<211> LENGTH: 728
<212> TYPE: PRT
<213> ORGANISM: Bacillus deramificans

<400> SEQUENCE: 2

```
Met Gly Ile Ser Tyr Asp Ser Glu Asn Arg Ile Phe His Leu Gln Gly
1               5                   10                  15

Lys Gly Thr Ser Tyr Leu Met Gln Val Leu Lys Asp Gly Tyr Leu Ala
            20                  25                  30

His Leu Tyr Trp Gly Arg Gly Val Arg Gln Tyr Ser Gly Gly Ile Pro
        35                  40                  45

Ile Thr Phe Phe Asp Arg Gly Phe Ser Pro Asn Pro Asp Pro Ser Asp
    50                  55                  60

Arg Thr Phe Ser Leu Asp Thr Leu Pro Gln Glu Tyr Pro Ala Tyr Gly
65                  70                  75                  80

Asn Thr Asp Phe Arg Thr Pro Ala Tyr Gln Val Gln Leu Glu Asn Gly
                85                  90                  95

Ser Thr Ile Ser Asp Leu Arg Tyr Lys Gly His Ala Ile Tyr Lys Gly
            100                 105                 110

Lys Pro Lys Leu Glu Gly Leu Pro Ala Val Tyr Val Glu Asp Asp Arg
        115                 120                 125

Glu Ala Glu Thr Leu Glu Ile Thr Leu Glu Asp Ser Leu Ile Gly Leu
    130                 135                 140

Glu Met Val Leu Val Tyr Thr Val Phe Glu Asn Phe Ser Ala Ile Thr
145                 150                 155                 160

Arg Ser Val Arg Phe Glu Asn Lys Gly Thr Gln Asp Leu Lys Ile Leu
                165                 170                 175

Arg Ala Leu Ser Ala Asn Ile Asp Phe Arg Asp Asp Phe Glu Leu
            180                 185                 190

Ile Thr Leu Tyr Gly Ser His Ile Asn Glu Arg Asn Ile Ala Arg Arg
        195                 200                 205

Pro Ile Gln Pro Gly Thr Gln Ser Ile Glu Ser Arg Arg Gly Ala Ser
    210                 215                 220

Ser His Gln Gln Asn Pro Phe Leu Ala Leu Leu Arg Pro Asn Ala Thr
225                 230                 235                 240

Glu Asp Gln Gly Asp Val Tyr Gly Leu Asn Leu Val Tyr Ser Gly Asn
                245                 250                 255

Phe Leu Gly Gln Val Glu Val Asn Gln Phe Gln Thr Thr Arg Val Ser
            260                 265                 270

Ile Gly Ile Asn Pro Phe Asp Phe Ser Trp Leu Leu Gln Pro Gly Glu
        275                 280                 285

Asn Phe Gln Ala Pro Glu Ala Val Met Val Tyr Ser Ser Glu Gly Leu
    290                 295                 300

Ala Gly Met Ser Gln Thr Tyr His Glu Leu Tyr Arg Thr Arg Leu Ser
305                 310                 315                 320

Arg Gly Glu His Arg Asp Lys Val Arg Pro Ile Leu Ile Asn Asn Trp
                325                 330                 335

Glu Ala Thr Tyr Phe Asp Phe Asn Ala Asp Lys Ile Val Glu Ile Ala
            340                 345                 350

Gln Val Gly Lys Glu Leu Gly Met Glu Leu Met Val Leu Asp Asp Gly
        355                 360                 365

Trp Phe Gly Lys Arg Asp Asp Asp Phe Thr Ser Leu Gly Asp Trp Val
    370                 375                 380
```

Val Asp Lys Arg Lys Leu Pro His Gly Leu Thr Asp Leu Ala Glu Arg
385                 390                 395                 400

Val Arg Ser Leu Gly Met Glu Phe Gly Leu Trp Phe Glu Pro Glu Met
            405                 410                 415

Val Ser Met Glu Ser Asp Leu Tyr Lys Arg His Pro Asp Trp Cys Leu
        420                 425                 430

His Val Pro Asn Arg Pro Lys Ser Glu Gly Arg Asn Gln Leu Ile Leu
            435                 440                 445

Asp Leu Ser Arg Gln Glu Val Cys Asp Tyr Val Ile Glu Ser Val Ser
    450                 455                 460

Ser Ile Leu Ser Thr Val Pro Ile Ser Tyr Val Lys Trp Asp Met Asn
465                 470                 475                 480

Arg His Met Thr Glu Ile Gly Ser Ala Asp Leu Leu Pro Glu Arg Gln
                485                 490                 495

Arg Glu Thr Ala His Arg Tyr Met Leu Gly Leu Tyr Tyr Val Leu Glu
            500                 505                 510

Thr Ile Val Thr Arg Phe Pro His Val Leu Phe Glu Ser Cys Ser Gly
        515                 520                 525

Gly Gly Gly Arg Phe Asp Pro Gly Met Leu Tyr Tyr Met Pro Gln Val
530                 535                 540

Trp Thr Ser Asp Asn Thr Asp Ala Ile Ser Arg Leu Lys Ile Gln Tyr
545                 550                 555                 560

Gly Thr Ser Leu Val Tyr Pro Ile Ser Ser Met Gly Ser His Val Ser
                565                 570                 575

Ala Val Pro Asn His Gln Val Gly Arg Val Thr Pro Leu Asp Ile Arg
            580                 585                 590

Gly His Ala Ala Met Ser Gly Asn Leu Gly Tyr Glu Leu Asp Leu Thr
        595                 600                 605

Lys Leu Ser Asp Gln Glu Lys Glu Val Lys Leu Gln Ile Ala Gln
    610                 615                 620

Tyr Lys Glu Ile Arg Gln Leu Val Gln Phe Gly Ser Phe Tyr Arg Leu
625                 630                 635                 640

Leu Ser Pro Phe Glu Gly Asn Glu Thr Ala Trp Val Phe Val Ser Ser
                645                 650                 655

Asp Gln Lys Glu Cys Leu Phe Gly Tyr Phe Arg Val Leu Ser Gln Pro
            660                 665                 670

Asn Ala Pro Thr Lys Ile Ile Lys Leu Lys Gly Leu Asn Leu Gly Glu
        675                 680                 685

Arg Tyr Lys Lys Thr Gly Ser Asp Glu Ser Phe Gly Asp Glu Leu
    690                 695                 700

Met Tyr Leu Gly Ile Asn Ile Pro Glu Leu Lys Gly Asp Phe Gln Ser
705                 710                 715                 720

Val Phe Trp His Phe Glu Ala Glu
                725

<210> SEQ ID NO 3
<211> LENGTH: 734
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(734)

<400> SEQUENCE: 3

```
Met Gly Ile Ser Tyr Asp Ser Glu Asn Arg Ile Phe His Leu Gln Gly
1               5                   10                  15

Lys Gly Thr Ser Tyr Leu Met Gln Val Leu Lys Asp Gly Tyr Leu Ala
                20                  25                  30

His Leu Tyr Trp Gly Arg Gly Val Arg Gln Tyr Ser Gly Gly Ile Pro
            35                  40                  45

Ile Thr Phe Phe Asp Arg Gly Phe Ser Pro Asn Pro Asp Pro Ser Asp
        50                  55                  60

Arg Thr Phe Ser Leu Asp Thr Leu Pro Gln Glu Tyr Pro Ala Tyr Gly
65                  70                  75                  80

Asn Thr Asp Phe Arg Thr Pro Ala Tyr Gln Val Gln Leu Glu Asn Gly
                85                  90                  95

Ser Thr Ile Ser Asp Leu Arg Tyr Lys Gly His Ala Ile Tyr Lys Gly
                100                 105                 110

Lys Pro Lys Leu Glu Gly Leu Pro Ala Val Tyr Val Glu Asp Asp Arg
            115                 120                 125

Glu Ala Glu Thr Leu Glu Ile Thr Leu Glu Asp Ser Leu Ile Gly Leu
        130                 135                 140

Glu Met Val Leu Val Tyr Thr Val Phe Glu Asn Phe Ser Ala Ile Thr
145                 150                 155                 160

Arg Ser Val Arg Phe Glu Asn Lys Gly Thr Gln Asp Leu Lys Ile Leu
                165                 170                 175

Arg Ala Leu Ser Ala Asn Ile Asp Phe Arg Asp Asp Phe Glu Leu
                180                 185                 190

Ile Thr Leu Tyr Gly Ser His Ile Asn Glu Arg Asn Ile Ala Arg Arg
            195                 200                 205

Pro Ile Gln Pro Gly Thr Gln Ser Ile Glu Ser Arg Arg Gly Ala Ser
        210                 215                 220

Ser His Gln Gln Asn Pro Phe Leu Ala Leu Leu Arg Pro Asn Ala Thr
225                 230                 235                 240

Glu Asp Gln Gly Asp Val Tyr Gly Leu Asn Leu Val Tyr Ser Gly Asn
                245                 250                 255

Phe Leu Gly Gln Val Glu Val Asn Gln Phe Gln Thr Thr Arg Val Ser
                260                 265                 270

Ile Gly Ile Asn Pro Phe Asp Phe Ser Trp Leu Leu Gln Pro Gly Glu
            275                 280                 285

Asn Phe Gln Ala Pro Glu Ala Val Met Val Tyr Ser Ser Glu Gly Leu
        290                 295                 300

Ala Gly Met Ser Gln Thr Tyr His Glu Leu Tyr Arg Thr Arg Leu Ser
305                 310                 315                 320

Arg Gly Glu His Arg Asp Lys Val Arg Pro Ile Leu Ile Asn Asn Trp
                325                 330                 335

Glu Ala Thr Tyr Phe Asp Phe Asn Ala Asp Lys Ile Val Glu Ile Ala
            340                 345                 350

Gln Val Gly Lys Glu Leu Gly Met Glu Leu Met Val Leu Asp Asp Gly
        355                 360                 365

Trp Phe Gly Lys Arg Asp Asp Asp Phe Thr Ser Leu Gly Asp Trp Val
370                 375                 380

Val Asp Lys Arg Lys Leu Pro His Gly Leu Thr Asp Leu Ala Glu Arg
385                 390                 395                 400

Val Arg Ser Leu Gly Met Glu Phe Gly Leu Trp Phe Glu Pro Glu Met
                405                 410                 415
```

```
Val Ser Met Glu Ser Asp Leu Tyr Lys Arg His Pro Asp Trp Cys Leu
            420                 425                 430

His Val Pro Asn Arg Pro Lys Ser Glu Gly Arg Asn Gln Leu Ile Leu
                435                 440                 445

Asp Leu Ser Arg Gln Glu Val Cys Asp Tyr Val Ile Glu Ser Val Ser
            450                 455                 460

Ser Ile Leu Ser Thr Val Pro Ile Ser Tyr Val Lys Trp Asp Met Asn
465                 470                 475                 480

Arg His Met Thr Glu Ile Gly Ser Ala Asp Leu Leu Pro Glu Arg Gln
                485                 490                 495

Arg Glu Thr Ala His Arg Tyr Met Leu Gly Leu Tyr Tyr Val Leu Glu
            500                 505                 510

Thr Ile Val Thr Arg Phe Pro His Val Leu Phe Glu Ser Cys Ser Gly
            515                 520                 525

Gly Gly Gly Arg Phe Asp Pro Gly Met Leu Tyr Tyr Met Pro Gln Val
            530                 535                 540

Trp Thr Ser Asp Asn Thr Asp Ala Ile Ser Arg Leu Lys Ile Gln Tyr
545                 550                 555                 560

Gly Thr Ser Leu Val Tyr Pro Ile Ser Ser Met Gly Ser His Val Ser
                565                 570                 575

Ala Val Pro Asn His Gln Val Gly Arg Val Thr Pro Leu Asp Ile Arg
            580                 585                 590

Gly His Ala Ala Met Ser Gly Asn Leu Gly Tyr Glu Leu Asp Leu Thr
            595                 600                 605

Lys Leu Ser Asp Gln Lys Glu Glu Val Lys Leu Gln Ile Ala Gln
            610                 615                 620

Tyr Lys Glu Ile Arg Gln Leu Val Gln Phe Gly Ser Phe Tyr Arg Leu
625                 630                 635                 640

Leu Ser Pro Phe Glu Gly Asn Glu Thr Ala Trp Val Phe Val Ser Ser
                645                 650                 655

Asp Gln Lys Glu Cys Leu Phe Gly Tyr Phe Arg Val Leu Ser Gln Pro
            660                 665                 670

Asn Ala Pro Thr Lys Ile Ile Lys Leu Lys Gly Leu Asn Leu Gly Glu
            675                 680                 685

Arg Tyr Lys Lys Thr Gly Ser Asp Glu Ser Phe Phe Gly Asp Glu Leu
            690                 695                 700

Met Tyr Leu Gly Ile Asn Ile Pro Glu Leu Lys Gly Asp Phe Gln Ser
705                 710                 715                 720

Val Phe Trp His Phe Glu Ala Glu His His His His His
                725                 730

<210> SEQ ID NO 4
<211> LENGTH: 2196
<212> TYPE: DNA
<213> ORGANISM: Bacillus acidopullulyticus
<220> FEATURE:
<221> NAME/KEY: CDS
<222> LOCATION: (1)..(2193)
<220> FEATURE:
<221> NAME/KEY: mat_peptide
<222> LOCATION: (1)..(2193)

<400> SEQUENCE: 4 atg gca att caa ttc aat tca aca aag aga att ttc cat tta aaa gcc    48
Met Ala Ile Gln Phe Asn Ser Thr Lys Arg Ile Phe His Leu Lys Ala
1               5                  10                  15 aaa gat acc agc tat gta atg gaa att gta cgt gac ggt ttt ctg ctt    96
```

```
                Lys Asp Thr Ser Tyr Val Met Glu Ile Val Arg Asp Gly Phe Leu Leu
                        20                  25                  30 cat cat tat tgg gga aga aaa ata aac gaa tat aac caa tca aat aat      144
His His Tyr Trp Gly Arg Lys Ile Asn Glu Tyr Asn Gln Ser Asn Asn
            35                  40                  45 att caa ctg atg gat agg ggg ttt tcc gga aat ccc tat aaa gag gac      192
Ile Gln Leu Met Asp Arg Gly Phe Ser Gly Asn Pro Tyr Lys Glu Asp
50                  55                  60 cgg acg ttc tca ctc gat act cta ccg cag gaa tat ccg caa tat ggg      240
Arg Thr Phe Ser Leu Asp Thr Leu Pro Gln Glu Tyr Pro Gln Tyr Gly
65                  70                  75                  80 aat act gat ttt cgg aaa cct gca tac cag gtt caa tta gag aat ggg      288
Asn Thr Asp Phe Arg Lys Pro Ala Tyr Gln Val Gln Leu Glu Asn Gly
            85                  90                  95 tca acc att act gat ttg cga tat gaa tca cat gaa att ttt aaa ggt      336
Ser Thr Ile Thr Asp Leu Arg Tyr Glu Ser His Glu Ile Phe Lys Gly
                100                 105                 110 aaa att ccg ttg gaa ggg ctt cct gct acc tat gtt gaa gac gaa aat      384
Lys Ile Pro Leu Glu Gly Leu Pro Ala Thr Tyr Val Glu Asp Glu Asn
            115                 120                 125 gaa gct gaa aca cta gaa atc acg atg agg gat tcc tta aca ggt tta      432
Glu Ala Glu Thr Leu Glu Ile Thr Met Arg Asp Ser Leu Thr Gly Leu
130                 135                 140 aag gtg att cta agt tat acg gtt ttt gag cat ttt aat gtt att aca      480
Lys Val Ile Leu Ser Tyr Thr Val Phe Glu His Phe Asn Val Ile Thr
145                 150                 155                 160 aga tcg gca cga ttt gta aat gaa gga act gaa gga ctg acg tta tta      528
Arg Ser Ala Arg Phe Val Asn Glu Gly Thr Glu Gly Leu Thr Leu Leu
                165                 170                 175 agt gct tta agt tta tcc gtt gat ttc aga gat gcg gat ttt gac ttc      576
Ser Ala Leu Ser Leu Ser Val Asp Phe Arg Asp Ala Asp Phe Asp Phe
            180                 185                 190 ctg cat ctc cac gga gca cat gta aaa gaa aga cat atc gaa cgg cag      624
Leu His Leu His Gly Ala His Val Lys Glu Arg His Ile Glu Arg Gln
        195                 200                 205 cct ctc cgt cat gga atc cag tcc ata gaa agc aca aga ggc gcc agc      672
Pro Leu Arg His Gly Ile Gln Ser Ile Glu Ser Thr Arg Gly Ala Ser
210                 215                 220 agt cat cag cat aat cct ttt att gcc ttg tta aga aaa gaa aca aat      720
Ser His Gln His Asn Pro Phe Ile Ala Leu Leu Arg Lys Glu Thr Asn
225                 230                 235                 240 gaa gat gtc ggg gaa gtc ttt gct ttt aac ttt gta tat agt ggc aat      768
Glu Asp Val Gly Glu Val Phe Ala Phe Asn Phe Val Tyr Ser Gly Asn
                245                 250                 255 ttc tta gcc cag gca gaa gtg gat caa ttt aac aac aca cgc gta aca      816
Phe Leu Ala Gln Ala Glu Val Asp Gln Phe Asn Asn Thr Arg Val Thr
            260                 265                 270 cta ggg att aat cct ttt gat ttc agc tgg aaa ttg caa ccg ggt gaa      864
Leu Gly Ile Asn Pro Phe Asp Phe Ser Trp Lys Leu Gln Pro Gly Glu
        275                 280                 285 acg ttt caa act ccc gag gca gtc atg gtt tat tca tca gaa ggg ctg      912
Thr Phe Gln Thr Pro Glu Ala Val Met Val Tyr Ser Ser Glu Gly Leu
290                 295                 300 ggg gat atg tcc cgg aca ttc cat cag ata tat aag act cgg ctt gta      960
Gly Asp Met Ser Arg Thr Phe His Gln Ile Tyr Lys Thr Arg Leu Val
305                 310                 315                 320 aga gga aca ttc cgg gat aag gaa cgt cct att tta gtc aac aac tgg     1008
Arg Gly Thr Phe Arg Asp Lys Glu Arg Pro Ile Leu Val Asn Asn Trp
                325                 330                 335
```

```
                                                             -continued gaa gca acc tat ttt gat ttt aat gct gaa aaa atc gaa gat att gct    1056
Glu Ala Thr Tyr Phe Asp Phe Asn Ala Glu Lys Ile Glu Asp Ile Ala
            340                 345                 350 aaa gca gga agc gaa tta ggg ata gaa tta ttt gtt ctt gat gat gga    1104
Lys Ala Gly Ser Glu Leu Gly Ile Glu Leu Phe Val Leu Asp Asp Gly
        355                 360                 365 tgg ttt ggc aag cgg aac aat gat acg acc tca cta ggt gac tgg ttt    1152
Trp Phe Gly Lys Arg Asn Asn Asp Thr Thr Ser Leu Gly Asp Trp Phe
370                 375                 380 gta gat cgg gaa aaa ctt cca gaa gga ctt gat cag ctt gca cat cgt    1200
Val Asp Arg Glu Lys Leu Pro Glu Gly Leu Asp Gln Leu Ala His Arg
385                 390                 395                 400 gta acg gat ttg ggt atg gaa ttt ggt ctt tgg ttt gaa ccg gaa atg    1248
Val Thr Asp Leu Gly Met Glu Phe Gly Leu Trp Phe Glu Pro Glu Met
                405                 410                 415 atc tcg gtt gat agt gat tta tat cgg gag cat cct gat tgg tgt cta    1296
Ile Ser Val Asp Ser Asp Leu Tyr Arg Glu His Pro Asp Trp Cys Leu
            420                 425                 430 cat gtt cca aat cgc aat cgt tcg gaa agc aga aat caa tta atc ctt    1344
His Val Pro Asn Arg Asn Arg Ser Glu Ser Arg Asn Gln Leu Ile Leu
        435                 440                 445 gat ttt tca aga gaa gat gta tgt gca gaa att aca aaa aga gtt tca    1392
Asp Phe Ser Arg Glu Asp Val Cys Ala Glu Ile Thr Lys Arg Val Ser
450                 455                 460 gat atc ctt tcg agt tta ccg att tcc tat gtg aaa tgg gat atg aac    1440
Asp Ile Leu Ser Ser Leu Pro Ile Ser Tyr Val Lys Trp Asp Met Asn
465                 470                 475                 480 cgg cat atg act gaa atc ggt tct gca gcg tta ccg ccg gag cgt caa    1488
Arg His Met Thr Glu Ile Gly Ser Ala Ala Leu Pro Pro Glu Arg Gln
                485                 490                 495 cgg gag act gcc cat cgc tat atg tta ggg cta tat aaa gta ttg gag    1536
Arg Glu Thr Ala His Arg Tyr Met Leu Gly Leu Tyr Lys Val Leu Glu
            500                 505                 510 gaa att act tct gga ttc cct aac atc cta ttt gaa agc tgt tcc gga    1584
Glu Ile Thr Ser Gly Phe Pro Asn Ile Leu Phe Glu Ser Cys Ser Gly
        515                 520                 525 ggt ggc ggc aga ttt gat cca ggg att ctc tat tac atg ccg caa act    1632
Gly Gly Gly Arg Phe Asp Pro Gly Ile Leu Tyr Tyr Met Pro Gln Thr
530                 535                 540 tgg aca agt gac aac aca gat gcg gtt tcc cga ttg aaa att caa tac    1680
Trp Thr Ser Asp Asn Thr Asp Ala Val Ser Arg Leu Lys Ile Gln Tyr
545                 550                 555                 560 gga aca agt ctt gtt tat cca att gtt tcc atg ggt gct cac gtt tct    1728
Gly Thr Ser Leu Val Tyr Pro Ile Val Ser Met Gly Ala His Val Ser
                565                 570                 575 gct gtt cca aat cac cag gtc gac aga atc aca acg ttg acc atg cgc    1776
Ala Val Pro Asn His Gln Val Asp Arg Ile Thr Thr Leu Thr Met Arg
            580                 585                 590 ggg gat gtt gcc atg tca ggg aat ttg ggg tat gaa ttg gat tta acc    1824
Gly Asp Val Ala Met Ser Gly Asn Leu Gly Tyr Glu Leu Asp Leu Thr
        595                 600                 605 aaa ttg cct gaa atg gaa aaa gct gaa gtt aag aaa cag gtt tcc ctc    1872
Lys Leu Pro Glu Met Glu Lys Ala Glu Val Lys Lys Gln Val Ser Leu
610                 615                 620 tat aaa gaa ata cgc tcc tta atc caa ttt ggc gat ttt tat cga atc    1920
Tyr Lys Glu Ile Arg Ser Leu Ile Gln Phe Gly Asp Phe Tyr Arg Ile
625                 630                 635                 640 aag agt ccc ttt gaa ggc aat gaa aca gca tgg gtc ttt acg aac gag    1968
Lys Ser Pro Phe Glu Gly Asn Glu Thr Ala Trp Val Phe Thr Asn Glu
                645                 650                 655
```

```
gat aaa tca gaa gca att gtc ttc tat ttc cgg gta ctg gct gaa ccg      2016
Asp Lys Ser Glu Ala Ile Val Phe Tyr Phe Arg Val Leu Ala Glu Pro
        660                 665                 670 gct gca ccg ttt agt ttc tta aag gta aag ggc gtt gat att gcc aag      2064
Ala Ala Pro Phe Ser Phe Leu Lys Val Lys Gly Val Asp Ile Ala Lys
675                 680                 685 aaa tat caa gtg gtc gga acc ggt cag gtt ttc ggt gga gat gaa ctt      2112
Lys Tyr Gln Val Val Gly Thr Gly Gln Val Phe Gly Gly Asp Glu Leu
        690                 695                 700 tct tat gca ggt ttg agc atc ccg gca tct att aaa ggg gat ttt cag      2160
Ser Tyr Ala Gly Leu Ser Ile Pro Ala Ser Ile Lys Gly Asp Phe Gln
705                 710                 715                 720 agc tat gtt tgg cat tta aaa gaa gta aat tgt taa                      2196
Ser Tyr Val Trp His Leu Lys Glu Val Asn Cys
        725                 730

<210> SEQ ID NO 5
<211> LENGTH: 731
<212> TYPE: PRT
<213> ORGANISM: Bacillus acidopullulyticus

<400> SEQUENCE: 5

Met Ala Ile Gln Phe Asn Ser Thr Lys Arg Ile Phe His Leu Lys Ala
1               5                   10                  15

Lys Asp Thr Ser Tyr Val Met Glu Ile Val Arg Asp Gly Phe Leu Leu
            20                  25                  30

His His Tyr Trp Gly Arg Lys Ile Asn Glu Tyr Asn Gln Ser Asn Asn
        35                  40                  45

Ile Gln Leu Met Asp Arg Gly Phe Ser Gly Asn Pro Tyr Lys Glu Asp
    50                  55                  60

Arg Thr Phe Ser Leu Asp Thr Leu Pro Gln Glu Tyr Pro Gln Tyr Gly
65                  70                  75                  80

Asn Thr Asp Phe Arg Lys Pro Ala Tyr Gln Val Gln Leu Glu Asn Gly
                85                  90                  95

Ser Thr Ile Thr Asp Leu Arg Tyr Glu Ser His Glu Ile Phe Lys Gly
            100                 105                 110

Lys Ile Pro Leu Glu Gly Leu Pro Ala Thr Tyr Val Glu Asp Glu Asn
        115                 120                 125

Glu Ala Glu Thr Leu Glu Ile Thr Met Arg Asp Ser Leu Thr Gly Leu
    130                 135                 140

Lys Val Ile Leu Ser Tyr Thr Val Phe Glu His Phe Asn Val Ile Thr
145                 150                 155                 160

Arg Ser Ala Arg Phe Val Asn Glu Gly Thr Glu Gly Leu Thr Leu Leu
                165                 170                 175

Ser Ala Leu Ser Leu Ser Val Asp Phe Arg Asp Ala Asp Phe Asp Phe
            180                 185                 190

Leu His Leu His Gly Ala His Val Lys Glu Arg His Ile Glu Arg Gln
        195                 200                 205

Pro Leu Arg His Gly Ile Gln Ser Ile Glu Ser Thr Arg Gly Ala Ser
    210                 215                 220

Ser His Gln His Asn Pro Phe Ile Ala Leu Leu Arg Lys Glu Thr Asn
225                 230                 235                 240

Glu Asp Val Gly Glu Val Phe Ala Phe Asn Phe Val Tyr Ser Gly Asn
                245                 250                 255

Phe Leu Ala Gln Ala Glu Val Asp Gln Phe Asn Asn Thr Arg Val Thr
            260                 265                 270
```

```
Leu Gly Ile Asn Pro Phe Asp Phe Ser Trp Lys Leu Gln Pro Gly Glu
            275                 280                 285

Thr Phe Gln Thr Pro Glu Ala Val Met Val Tyr Ser Ser Glu Gly Leu
    290                 295                 300

Gly Asp Met Ser Arg Thr Phe His Gln Ile Tyr Lys Thr Arg Leu Val
305                 310                 315                 320

Arg Gly Thr Phe Arg Asp Lys Glu Arg Pro Ile Leu Val Asn Asn Trp
                325                 330                 335

Glu Ala Thr Tyr Phe Asp Phe Asn Ala Glu Lys Ile Glu Asp Ile Ala
                340                 345                 350

Lys Ala Gly Ser Glu Leu Gly Ile Glu Leu Phe Val Leu Asp Asp Gly
            355                 360                 365

Trp Phe Gly Lys Arg Asn Asn Asp Thr Thr Ser Leu Gly Asp Trp Phe
    370                 375                 380

Val Asp Arg Glu Lys Leu Pro Glu Gly Leu Asp Gln Leu Ala His Arg
385                 390                 395                 400

Val Thr Asp Leu Gly Met Glu Phe Gly Leu Trp Phe Glu Pro Glu Met
                405                 410                 415

Ile Ser Val Asp Ser Asp Leu Tyr Arg Glu His Pro Asp Trp Cys Leu
            420                 425                 430

His Val Pro Asn Arg Asn Arg Ser Glu Ser Arg Asn Gln Leu Ile Leu
    435                 440                 445

Asp Phe Ser Arg Glu Asp Val Cys Ala Glu Ile Thr Lys Arg Val Ser
450                 455                 460

Asp Ile Leu Ser Ser Leu Pro Ile Ser Tyr Val Lys Trp Asp Met Asn
465                 470                 475                 480

Arg His Met Thr Glu Ile Gly Ser Ala Ala Leu Pro Pro Glu Arg Gln
                485                 490                 495

Arg Glu Thr Ala His Arg Tyr Met Leu Gly Leu Tyr Lys Val Leu Glu
            500                 505                 510

Glu Ile Thr Ser Gly Phe Pro Asn Ile Leu Phe Glu Ser Cys Ser Gly
    515                 520                 525

Gly Gly Gly Arg Phe Asp Pro Gly Ile Leu Tyr Tyr Met Pro Gln Thr
530                 535                 540

Trp Thr Ser Asp Asn Thr Asp Ala Val Ser Arg Leu Lys Ile Gln Tyr
545                 550                 555                 560

Gly Thr Ser Leu Val Tyr Pro Ile Val Ser Met Gly Ala His Val Ser
                565                 570                 575

Ala Val Pro Asn His Gln Val Asp Arg Ile Thr Thr Leu Thr Met Arg
            580                 585                 590

Gly Asp Val Ala Met Ser Gly Asn Leu Gly Tyr Glu Leu Asp Leu Thr
    595                 600                 605

Lys Leu Pro Glu Met Glu Lys Ala Glu Val Lys Lys Gln Val Ser Leu
610                 615                 620

Tyr Lys Glu Ile Arg Ser Leu Ile Gln Phe Gly Asp Phe Tyr Arg Ile
625                 630                 635                 640

Lys Ser Pro Phe Glu Gly Asn Glu Thr Ala Trp Val Phe Thr Asn Glu
                645                 650                 655

Asp Lys Ser Glu Ala Ile Val Phe Tyr Phe Arg Val Leu Ala Glu Pro
            660                 665                 670

Ala Ala Pro Phe Ser Phe Leu Lys Val Lys Gly Val Asp Ile Ala Lys
    675                 680                 685
```

```
Lys Tyr Gln Val Val Gly Thr Gly Gln Val Phe Gly Gly Asp Glu Leu
690                 695                 700

Ser Tyr Ala Gly Leu Ser Ile Pro Ala Ser Ile Lys Gly Asp Phe Gln
705                 710                 715                 720

Ser Tyr Val Trp His Leu Lys Glu Val Asn Cys
                725                 730

<210> SEQ ID NO 6
<211> LENGTH: 737
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(737)

<400> SEQUENCE: 6

Met Ala Ile Gln Phe Asn Ser Thr Lys Arg Ile Phe His Leu Lys Ala
1               5                   10                  15

Lys Asp Thr Ser Tyr Val Met Glu Ile Val Arg Asp Gly Phe Leu Leu
                20                  25                  30

His His Tyr Trp Gly Arg Lys Ile Asn Glu Tyr Asn Gln Ser Asn Asn
            35                  40                  45

Ile Gln Leu Met Asp Arg Gly Phe Ser Gly Asn Pro Tyr Lys Glu Asp
        50                  55                  60

Arg Thr Phe Ser Leu Asp Thr Leu Pro Gln Glu Tyr Pro Gln Tyr Gly
65                  70                  75                  80

Asn Thr Asp Phe Arg Lys Pro Ala Tyr Gln Val Gln Leu Glu Asn Gly
                85                  90                  95

Ser Thr Ile Thr Asp Leu Arg Tyr Glu Ser His Glu Ile Phe Lys Gly
            100                 105                 110

Lys Ile Pro Leu Glu Gly Leu Pro Ala Thr Tyr Val Glu Asp Glu Asn
        115                 120                 125

Glu Ala Glu Thr Leu Glu Ile Thr Met Arg Asp Ser Leu Thr Gly Leu
130                 135                 140

Lys Val Ile Leu Ser Tyr Thr Val Phe Glu His Phe Asn Val Ile Thr
145                 150                 155                 160

Arg Ser Ala Arg Phe Val Asn Glu Gly Thr Glu Gly Leu Thr Leu Leu
                165                 170                 175

Ser Ala Leu Ser Leu Ser Val Asp Phe Arg Asp Ala Asp Phe Asp Phe
            180                 185                 190

Leu His Leu His Gly Ala His Val Lys Glu Arg His Ile Glu Arg Gln
        195                 200                 205

Pro Leu Arg His Gly Ile Gln Ser Ile Glu Ser Thr Arg Gly Ala Ser
210                 215                 220

Ser His Gln His Asn Pro Phe Ile Ala Leu Leu Arg Lys Glu Thr Asn
225                 230                 235                 240

Glu Asp Val Gly Glu Val Phe Ala Phe Asn Phe Val Tyr Ser Gly Asn
                245                 250                 255

Phe Leu Ala Gln Ala Glu Val Asp Gln Phe Asn Asn Thr Arg Val Thr
            260                 265                 270

Leu Gly Ile Asn Pro Phe Asp Phe Ser Trp Lys Leu Gln Pro Gly Glu
        275                 280                 285

Thr Phe Gln Thr Pro Glu Ala Val Met Val Tyr Ser Ser Glu Gly Leu
290                 295                 300
```

```
Gly Asp Met Ser Arg Thr Phe His Gln Ile Tyr Lys Thr Arg Leu Val
305                 310                 315                 320

Arg Gly Thr Phe Arg Asp Lys Glu Arg Pro Ile Leu Val Asn Asn Trp
            325                 330                 335

Glu Ala Thr Tyr Phe Asp Phe Asn Ala Glu Lys Ile Glu Asp Ile Ala
            340                 345                 350

Lys Ala Gly Ser Glu Leu Gly Ile Glu Leu Phe Val Leu Asp Asp Gly
            355                 360                 365

Trp Phe Gly Lys Arg Asn Asn Asp Thr Thr Ser Leu Gly Asp Trp Phe
    370                 375                 380

Val Asp Arg Glu Lys Leu Pro Glu Gly Leu Asp Gln Leu Ala His Arg
385                 390                 395                 400

Val Thr Asp Leu Gly Met Glu Phe Gly Leu Trp Phe Glu Pro Glu Met
                405                 410                 415

Ile Ser Val Asp Ser Asp Leu Tyr Arg Glu His Pro Asp Trp Cys Leu
                420                 425                 430

His Val Pro Asn Arg Asn Arg Ser Glu Ser Arg Asn Gln Leu Ile Leu
            435                 440                 445

Asp Phe Ser Arg Glu Asp Val Cys Ala Glu Ile Thr Lys Arg Val Ser
450                 455                 460

Asp Ile Leu Ser Ser Leu Pro Ile Ser Tyr Val Lys Trp Asp Met Asn
465                 470                 475                 480

Arg His Met Thr Glu Ile Gly Ser Ala Ala Leu Pro Pro Glu Arg Gln
                485                 490                 495

Arg Glu Thr Ala His Arg Tyr Met Leu Gly Leu Tyr Lys Val Leu Glu
            500                 505                 510

Glu Ile Thr Ser Gly Phe Pro Asn Ile Leu Phe Glu Ser Cys Ser Gly
            515                 520                 525

Gly Gly Gly Arg Phe Asp Pro Gly Ile Leu Tyr Tyr Met Pro Gln Thr
    530                 535                 540

Trp Thr Ser Asp Asn Thr Asp Ala Val Ser Arg Leu Lys Ile Gln Tyr
545                 550                 555                 560

Gly Thr Ser Leu Val Tyr Pro Ile Val Ser Met Gly Ala His Val Ser
                565                 570                 575

Ala Val Pro Asn His Gln Val Asp Arg Ile Thr Thr Leu Thr Met Arg
            580                 585                 590

Gly Asp Val Ala Met Ser Gly Asn Leu Gly Tyr Glu Leu Asp Leu Thr
            595                 600                 605

Lys Leu Pro Glu Met Glu Lys Ala Glu Val Lys Lys Gln Val Ser Leu
610                 615                 620

Tyr Lys Glu Ile Arg Ser Leu Ile Gln Phe Gly Asp Phe Tyr Arg Ile
625                 630                 635                 640

Lys Ser Pro Phe Glu Gly Asn Glu Thr Ala Trp Val Phe Thr Asn Glu
                645                 650                 655

Asp Lys Ser Glu Ala Ile Val Phe Tyr Phe Arg Val Leu Ala Glu Pro
            660                 665                 670

Ala Ala Pro Phe Ser Phe Leu Lys Val Lys Gly Val Asp Ile Ala Lys
            675                 680                 685

Lys Tyr Gln Val Val Gly Thr Gly Gln Val Phe Gly Asp Glu Leu
            690                 695                 700

Ser Tyr Ala Gly Leu Ser Ile Pro Ala Ser Ile Lys Gly Asp Phe Gln
705                 710                 715                 720

Ser Tyr Val Trp His Leu Lys Glu Val Asn Cys His His His His His
```

His

```
<210> SEQ ID NO 7
<211> LENGTH: 2199
<212> TYPE: DNA
<213> ORGANISM: Anoxybacillus bogrovensis
<220> FEATURE:
<221> NAME/KEY: CDS
<222> LOCATION: (1)..(2196)
<220> FEATURE:
<221> NAME/KEY: mat_peptide
<222> LOCATION: (1)..(2196)

<400> SEQUENCE: 7
```

| | | | | | | | | | | | | | | | | |
|---|---|---|---|---|---|---|---|---|---|---|---|---|---|---|---|---|
| atg | gca | att | atg | ttc | gat | tct | ata | aac | caa | aca | ttt | cat | tta | cag | gca | 48 |
| Met | Ala | Ile | Met | Phe | Asp | Ser | Ile | Asn | Gln | Thr | Phe | His | Leu | Gln | Ala | |
| 1 | | | | 5 | | | | | 10 | | | | | 15 | | |
| aaa | gac | aca | agc | tat | gtt | atg | caa | att | ttc | cgt | gac | ggg | tat | tta | gcc | 96 |
| Lys | Asp | Thr | Ser | Tyr | Val | Met | Gln | Ile | Phe | Arg | Asp | Gly | Tyr | Leu | Ala | |
| | | | 20 | | | | | 25 | | | | | 30 | | | |
| cat | ctt | tat | ttc | ggg | aaa | aaa | gtt | cgc | aac | tat | cac | cat | tcg | aat | aaa | 144 |
| His | Leu | Tyr | Phe | Gly | Lys | Lys | Val | Arg | Asn | Tyr | His | His | Ser | Asn | Lys | |
| | 35 | | | | | 40 | | | | | 45 | | | | | |
| tta | cag | ttt | tta | gat | cga | gga | ttc | tct | ccg | aat | cct | gac | cca | tct | gat | 192 |
| Leu | Gln | Phe | Leu | Asp | Arg | Gly | Phe | Ser | Pro | Asn | Pro | Asp | Pro | Ser | Asp | |
| 50 | | | | | 55 | | | | | 60 | | | | | | |
| cga | aca | ttt | tca | tta | gat | aca | ttg | ccg | caa | gaa | tat | cca | gca | tac | ggc | 240 |
| Arg | Thr | Phe | Ser | Leu | Asp | Thr | Leu | Pro | Gln | Glu | Tyr | Pro | Ala | Tyr | Gly | |
| 65 | | | | | 70 | | | | | 75 | | | | | 80 | |
| aat | aca | gac | ttt | cgc | aca | ccg | gct | tat | caa | ata | caa | ctt | gaa | aat | ggg | 288 |
| Asn | Thr | Asp | Phe | Arg | Thr | Pro | Ala | Tyr | Gln | Ile | Gln | Leu | Glu | Asn | Gly | |
| | | | | 85 | | | | | 90 | | | | | 95 | | |
| tct | acc | gta | tcg | gat | ttg | cgc | tat | aaa | aca | cat | aaa | atc | tac | aaa | gga | 336 |
| Ser | Thr | Val | Ser | Asp | Leu | Arg | Tyr | Lys | Thr | His | Lys | Ile | Tyr | Lys | Gly | |
| | | | 100 | | | | | 105 | | | | | 110 | | | |
| aag | ccg | aaa | tta | aat | gga | ttg | cca | gcg | act | tat | gtc | gaa | aca | gaa | gat | 384 |
| Lys | Pro | Lys | Leu | Asn | Gly | Leu | Pro | Ala | Thr | Tyr | Val | Glu | Thr | Glu | Asp | |
| | | 115 | | | | | 120 | | | | | 125 | | | | |
| gaa | gcg | gag | acg | ctg | gaa | atc | gag | tta | gag | gat | aat | atc | aca | aaa | cta | 432 |
| Glu | Ala | Glu | Thr | Leu | Glu | Ile | Glu | Leu | Glu | Asp | Asn | Ile | Thr | Lys | Leu | |
| | 130 | | | | | 135 | | | | | 140 | | | | | |
| aaa | gta | att | ctt | tct | tat | acc | gta | ttt | gaa | cat | ttc | aat | gcg | att | aca | 480 |
| Lys | Val | Ile | Leu | Ser | Tyr | Thr | Val | Phe | Glu | His | Phe | Asn | Ala | Ile | Thr | |
| 145 | | | | | 150 | | | | | 155 | | | | | 160 | |
| cgt | ttt | gtt | cgc | ttt | gaa | aat | caa | ggt | tca | gaa | aat | ata | aaa | att | tta | 528 |
| Arg | Phe | Val | Arg | Phe | Glu | Asn | Gln | Gly | Ser | Glu | Asn | Ile | Lys | Ile | Leu | |
| | | | | 165 | | | | | 170 | | | | | 175 | | |
| cgt | gcg | tta | agt | atg | aat | atc | gat | ttt | cgc | gat | gca | aac | ttc | gat | ttt | 576 |
| Arg | Ala | Leu | Ser | Met | Asn | Ile | Asp | Phe | Arg | Asp | Ala | Asn | Phe | Asp | Phe | |
| | | | 180 | | | | | 185 | | | | | 190 | | | |
| ctg | cat | ctt | tca | ggc | gca | cat | tgc | cga | gaa | cga | tat | gta | gaa | aga | aaa | 624 |
| Leu | His | Leu | Ser | Gly | Ala | His | Cys | Arg | Glu | Arg | Tyr | Val | Glu | Arg | Lys | |
| | | 195 | | | | | 200 | | | | | 205 | | | | |
| ccg | ctt | ttt | gtc | ggc | act | caa | tcg | atc | gaa | agc | cga | aga | ggg | gca | agc | 672 |
| Pro | Leu | Phe | Val | Gly | Thr | Gln | Ser | Ile | Glu | Ser | Arg | Arg | Gly | Ala | Ser | |
| | 210 | | | | | 215 | | | | | 220 | | | | | |
| agc | cat | caa | caa | aac | cca | ttc | atc | gcg | ttg | tta | aga | aaa | aat | gcc | aat | 720 |
| Ser | His | Gln | Gln | Asn | Pro | Phe | Ile | Ala | Leu | Leu | Arg | Lys | Asn | Ala | Asn | |
| 225 | | | | | 230 | | | | | 235 | | | | | 240 | |
| gaa | gac | gaa | ggt | gaa | gta | ttt | ggt | ttt | agc | ctt | gtg | tac | agc | ggc | aat | 768 |

|   |   |   |   |   |   |   |   |   |   |   |   |   |   |   |
|---|---|---|---|---|---|---|---|---|---|---|---|---|---|---|
| Glu | Asp | Glu | Gly | Glu | Val | Phe | Gly | Phe | Ser | Leu | Val | Tyr | Ser | Gly | Asn |
|   |   |   |   | 245 |   |   |   | 250 |   |   |   | 255 |   |

```
ttc ctt gct caa gtg gaa gtt gat caa ttt cac aca gca cgt gtg tcg      816
Phe Leu Ala Gln Val Glu Val Asp Gln Phe His Thr Ala Arg Val Ser
        260                 265                 270 cta gga att aat ccg ttt gat ttt act tgg cta tta gag cct ggc gaa      864
Leu Gly Ile Asn Pro Phe Asp Phe Thr Trp Leu Leu Glu Pro Gly Glu
            275                 280                 285 tcg ttt caa aca ccg gaa gtg gtg atg gtc tat tcc gat caa gga cta      912
Ser Phe Gln Thr Pro Glu Val Val Met Val Tyr Ser Asp Gln Gly Leu
    290                 295                 300 aac ggg atg tcg caa acg ttt cat cga cta tac cga act cgt ttg gct      960
Asn Gly Met Ser Gln Thr Phe His Arg Leu Tyr Arg Thr Arg Leu Ala
305                 310                 315                 320 cgc gga ccg ttc cga gac aaa gaa cgt cca att ctc att aac aac tgg     1008
Arg Gly Pro Phe Arg Asp Lys Glu Arg Pro Ile Leu Ile Asn Asn Trp
                325                 330                 335 gaa gct acc tat ttt gat ttt aac gaa gag aaa att ttg gaa att gtg     1056
Glu Ala Thr Tyr Phe Asp Phe Asn Glu Glu Lys Ile Leu Glu Ile Val
            340                 345                 350 aaa gca ggt aaa gaa tta gga atc gag tta ttt gta tta gat gac ggt     1104
Lys Ala Gly Lys Glu Leu Gly Ile Glu Leu Phe Val Leu Asp Asp Gly
        355                 360                 365 tgg ttt ggc aaa cgg gac gat gat aaa agc tct tta gga gat tgg ttc     1152
Trp Phe Gly Lys Arg Asp Asp Asp Lys Ser Ser Leu Gly Asp Trp Phe
    370                 375                 380 gtt gac aaa agg aag ctt tca aat gga tta gta gga cta gct aca aaa     1200
Val Asp Lys Arg Lys Leu Ser Asn Gly Leu Val Gly Leu Ala Thr Lys
385                 390                 395                 400 atc cga gag atg gga atg cag ttt gga cta tgg gtt gaa ccg gag atg     1248
Ile Arg Glu Met Gly Met Gln Phe Gly Leu Trp Val Glu Pro Glu Met
                405                 410                 415 att tcg atc gat agc gat tta tat cgc aag cat cca gac tgg tgc ctc     1296
Ile Ser Ile Asp Ser Asp Leu Tyr Arg Lys His Pro Asp Trp Cys Leu
            420                 425                 430 cat gtt cca aaa cgg ccg cgt tca gaa gga cgt aat cag ctt att ctg     1344
His Val Pro Lys Arg Pro Arg Ser Glu Gly Arg Asn Gln Leu Ile Leu
        435                 440                 445 gat tac tca cgt aaa gaa gtg tgt gat tac att atc aaa gta atg tcc     1392
Asp Tyr Ser Arg Lys Glu Val Cys Asp Tyr Ile Ile Lys Val Met Ser
    450                 455                 460 gat att tta tca agc gcc ccc att tcg tat gtg aaa tgg gat atg aat     1440
Asp Ile Leu Ser Ser Ala Pro Ile Ser Tyr Val Lys Trp Asp Met Asn
465                 470                 475                 480 cgt cac atg acc gaa atc gga tct gct tcc ttg ccg cca gaa aga caa     1488
Arg His Met Thr Glu Ile Gly Ser Ala Ser Leu Pro Pro Glu Arg Gln
                485                 490                 495 aga gaa aca gcc cac cgt tat atg tta ggg ttg tat cgc gta atg gag     1536
Arg Glu Thr Ala His Arg Tyr Met Leu Gly Leu Tyr Arg Val Met Glu
            500                 505                 510 gaa atc acc tcc aag ttt ccg cac gtt tta ttt gaa agt tgt tca ggc     1584
Glu Ile Thr Ser Lys Phe Pro His Val Leu Phe Glu Ser Cys Ser Gly
        515                 520                 525 gga ggt ggg cgt ttt gat cca ggg att ctt tat tac atg ccg caa acg     1632
Gly Gly Gly Arg Phe Asp Pro Gly Ile Leu Tyr Tyr Met Pro Gln Thr
    530                 535                 540 tgg acg agc gac aat aca gat gcg atc tct cgt tta aaa att caa tac     1680
Trp Thr Ser Asp Asn Thr Asp Ala Ile Ser Arg Leu Lys Ile Gln Tyr
545                 550                 555                 560
```

-continued

| | | |
|---|---|---|
| ggc aca agt atc gtt tat cca atc agc gca atg gga gca cat gtg tca<br>Gly Thr Ser Ile Val Tyr Pro Ile Ser Ala Met Gly Ala His Val Ser<br>565                             570                        575 | 1728 |
| gca gtt cca aac cat caa gtt cat cgc atc act tca ctg gat att cgc<br>Ala Val Pro Asn His Gln Val His Arg Ile Thr Ser Leu Asp Ile Arg<br>580                         585                       590 | 1776 |
| ggg cat gtg gcg atg tca gga aac ttt ggc tat gaa ctc gat tta acg<br>Gly His Val Ala Met Ser Gly Asn Phe Gly Tyr Glu Leu Asp Leu Thr<br>595                         600                       605 | 1824 |
| aaa tta acc gat gaa gag aag gaa aaa gtg aaa gag caa gtg gcc ttt<br>Lys Leu Thr Asp Glu Glu Lys Glu Lys Val Lys Glu Gln Val Ala Phe<br>610                         615                       620 | 1872 |
| tat aaa gaa att cgc cgt tta gtg caa tat gga aac ttt tat cga atc<br>Tyr Lys Glu Ile Arg Arg Leu Val Gln Tyr Gly Asn Phe Tyr Arg Ile<br>625                         630                       635               640 | 1920 |
| cta agc cca ttt gaa gga aat gaa acg gcg tgg atg ttc gtt tca gaa<br>Leu Ser Pro Phe Glu Gly Asn Glu Thr Ala Trp Met Phe Val Ser Glu<br>645                         650                       655 | 1968 |
| gac caa tcc gaa gcg ttt gtc gct tac ttt aga gta tta gcg gag gcg<br>Asp Gln Ser Glu Ala Phe Val Ala Tyr Phe Arg Val Leu Ala Glu Ala<br>660                         665                       670 | 2016 |
| aat gct cca att tct tct att cgt ctg aaa gga ctg aac ccc cgt aaa<br>Asn Ala Pro Ile Ser Ser Ile Arg Leu Lys Gly Leu Asn Pro Arg Lys<br>675                         680                       685 | 2064 |
| caa tac tat cta gtt gga aaa ggg gaa gta tat ggt ggt gat gag ttg<br>Gln Tyr Tyr Leu Val Gly Lys Gly Glu Val Tyr Gly Gly Asp Glu Leu<br>690                         695                       700 | 2112 |
| atg tat gtg ggg ata aat att cca tat att cta gga gac ttc atg agt<br>Met Tyr Val Gly Ile Asn Ile Pro Tyr Ile Leu Gly Asp Phe Met Ser<br>705                         710                       715               720 | 2160 |
| ttt act tgg gta tta aag gaa tgg gag aag gat ttc tga<br>Phe Thr Trp Val Leu Lys Glu Trp Glu Lys Asp Phe<br>725                         730 | 2199 |

<210> SEQ ID NO 8
<211> LENGTH: 732
<212> TYPE: PRT
<213> ORGANISM: Anoxybacillus bogrovensis

<400> SEQUENCE: 8

Met Ala Ile Met Phe Asp Ser Ile Asn Gln Thr Phe His Leu Gln Ala
1               5                   10                  15

Lys Asp Thr Ser Tyr Val Met Gln Ile Phe Arg Asp Gly Tyr Leu Ala
            20                  25                  30

His Leu Tyr Phe Gly Lys Lys Val Arg Asn Tyr His Ser Asn Lys
        35                  40                  45

Leu Gln Phe Leu Asp Arg Gly Phe Ser Pro Asn Pro Asp Pro Ser Asp
    50                  55                  60

Arg Thr Phe Ser Leu Asp Thr Leu Pro Gln Glu Tyr Pro Ala Tyr Gly
65                  70                  75                  80

Asn Thr Asp Phe Arg Thr Pro Ala Tyr Gln Ile Gln Leu Glu Asn Gly
                85                  90                  95

Ser Thr Val Ser Asp Leu Arg Tyr Lys Thr His Lys Ile Tyr Lys Gly
            100                 105                 110

Lys Pro Lys Leu Asn Gly Leu Pro Ala Thr Tyr Val Glu Thr Glu Asp
        115                 120                 125

Glu Ala Glu Thr Leu Glu Ile Glu Leu Glu Asp Asn Ile Thr Lys Leu
    130                 135                 140

-continued

```
Lys Val Ile Leu Ser Tyr Thr Val Phe Glu His Phe Asn Ala Ile Thr
145                 150                 155                 160

Arg Phe Val Arg Phe Glu Asn Gln Gly Ser Glu Asn Ile Lys Ile Leu
                165                 170                 175

Arg Ala Leu Ser Met Asn Ile Asp Phe Arg Asp Ala Asn Phe Asp Phe
                180                 185                 190

Leu His Leu Ser Gly Ala His Cys Arg Glu Arg Tyr Val Glu Arg Lys
                195                 200                 205

Pro Leu Phe Val Gly Thr Gln Ser Ile Glu Ser Arg Arg Gly Ala Ser
                210                 215                 220

Ser His Gln Gln Asn Pro Phe Ile Ala Leu Leu Arg Lys Asn Ala Asn
225                 230                 235                 240

Glu Asp Glu Gly Glu Val Phe Gly Phe Ser Leu Val Tyr Ser Gly Asn
                245                 250                 255

Phe Leu Ala Gln Val Glu Val Asp Gln Phe His Thr Ala Arg Val Ser
                260                 265                 270

Leu Gly Ile Asn Pro Phe Asp Phe Thr Trp Leu Leu Glu Pro Gly Glu
                275                 280                 285

Ser Phe Gln Thr Pro Glu Val Val Met Val Tyr Ser Asp Gln Gly Leu
                290                 295                 300

Asn Gly Met Ser Gln Thr Phe His Arg Leu Tyr Arg Thr Arg Leu Ala
305                 310                 315                 320

Arg Gly Pro Phe Arg Asp Lys Glu Arg Pro Ile Leu Ile Asn Asn Trp
                325                 330                 335

Glu Ala Thr Tyr Phe Asp Phe Asn Glu Glu Lys Ile Leu Glu Ile Val
                340                 345                 350

Lys Ala Gly Lys Glu Leu Gly Ile Glu Leu Phe Val Leu Asp Asp Gly
                355                 360                 365

Trp Phe Gly Lys Arg Asp Asp Asp Lys Ser Ser Leu Gly Asp Trp Phe
                370                 375                 380

Val Asp Lys Arg Lys Leu Ser Asn Gly Leu Val Gly Leu Ala Thr Lys
385                 390                 395                 400

Ile Arg Glu Met Gly Met Gln Phe Gly Leu Trp Val Glu Pro Glu Met
                405                 410                 415

Ile Ser Ile Asp Ser Asp Leu Tyr Arg Lys His Pro Asp Trp Cys Leu
                420                 425                 430

His Val Pro Lys Arg Pro Arg Ser Glu Gly Arg Asn Gln Leu Ile Leu
                435                 440                 445

Asp Tyr Ser Arg Lys Glu Val Cys Asp Tyr Ile Ile Lys Val Met Ser
450                 455                 460

Asp Ile Leu Ser Ser Ala Pro Ile Ser Tyr Val Lys Trp Asp Met Asn
465                 470                 475                 480

Arg His Met Thr Glu Ile Gly Ser Ala Ser Leu Pro Pro Glu Arg Gln
                485                 490                 495

Arg Glu Thr Ala His Arg Tyr Met Leu Gly Leu Tyr Arg Val Met Glu
                500                 505                 510

Glu Ile Thr Ser Lys Phe Pro His Val Leu Phe Glu Ser Cys Ser Gly
                515                 520                 525

Gly Gly Gly Arg Phe Asp Pro Gly Ile Leu Tyr Tyr Met Pro Gln Thr
                530                 535                 540

Trp Thr Ser Asp Asn Thr Asp Ala Ile Ser Arg Leu Lys Ile Gln Tyr
545                 550                 555                 560

Gly Thr Ser Ile Val Tyr Pro Ile Ser Ala Met Gly Ala His Val Ser
```

-continued

```
                   565                 570                 575
Ala Val Pro Asn His Gln Val His Arg Ile Thr Ser Leu Asp Ile Arg
            580                 585                 590

Gly His Val Ala Met Ser Gly Asn Phe Gly Tyr Glu Leu Asp Leu Thr
            595                 600                 605

Lys Leu Thr Asp Glu Glu Lys Glu Val Lys Glu Gln Val Ala Phe
            610                 615                 620

Tyr Lys Glu Ile Arg Arg Leu Val Gln Tyr Gly Asn Phe Tyr Arg Ile
625                 630                 635                 640

Leu Ser Pro Phe Glu Gly Asn Glu Thr Ala Trp Met Phe Val Ser Glu
                645                 650                 655

Asp Gln Ser Glu Ala Phe Val Ala Tyr Phe Arg Val Leu Ala Glu Ala
                660                 665                 670

Asn Ala Pro Ile Ser Ser Ile Arg Leu Lys Gly Leu Asn Pro Arg Lys
            675                 680                 685

Gln Tyr Tyr Leu Val Gly Lys Gly Val Tyr Gly Gly Asp Glu Leu
690                 695                 700

Met Tyr Val Gly Ile Asn Ile Pro Tyr Ile Leu Gly Asp Phe Met Ser
705                 710                 715                 720

Phe Thr Trp Val Leu Lys Glu Trp Glu Lys Asp Phe
                725                 730
```

```
<210> SEQ ID NO 9
<211> LENGTH: 738
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(738)

<400> SEQUENCE: 9

Met Ala Ile Met Phe Asp Ser Ile Asn Gln Thr Phe His Leu Gln Ala
1               5                   10                  15

Lys Asp Thr Ser Tyr Val Met Gln Ile Phe Arg Asp Gly Tyr Leu Ala
            20                  25                  30

His Leu Tyr Phe Gly Lys Lys Val Arg Asn Tyr His His Ser Asn Lys
        35                  40                  45

Leu Gln Phe Leu Asp Arg Gly Phe Ser Pro Asn Pro Asp Pro Ser Asp
    50                  55                  60

Arg Thr Phe Ser Leu Asp Thr Leu Pro Gln Glu Tyr Pro Ala Tyr Gly
65                  70                  75                  80

Asn Thr Asp Phe Arg Thr Pro Ala Tyr Gln Ile Gln Leu Glu Asn Gly
                85                  90                  95

Ser Thr Val Ser Asp Leu Arg Tyr Lys Thr His Lys Ile Tyr Lys Gly
            100                 105                 110

Lys Pro Lys Leu Asn Gly Leu Pro Ala Thr Tyr Val Glu Thr Glu Asp
        115                 120                 125

Glu Ala Glu Thr Leu Glu Ile Glu Leu Glu Asp Asn Ile Thr Lys Leu
    130                 135                 140

Lys Val Ile Leu Ser Tyr Thr Val Phe Glu His Phe Asn Ala Ile Thr
145                 150                 155                 160

Arg Phe Val Arg Phe Glu Asn Gln Gly Ser Glu Asn Ile Lys Ile Leu
                165                 170                 175

Arg Ala Leu Ser Met Asn Ile Asp Phe Arg Asp Ala Asn Phe Asp Phe
```

```
                180             185             190
Leu His Leu Ser Gly Ala His Cys Arg Glu Arg Tyr Val Glu Arg Lys
            195                 200                 205
Pro Leu Phe Val Gly Thr Gln Ser Ile Glu Ser Arg Arg Gly Ala Ser
        210                 215                 220
Ser His Gln Gln Asn Pro Phe Ile Ala Leu Leu Arg Lys Asn Ala Asn
225                 230                 235                 240
Glu Asp Glu Gly Glu Val Phe Gly Phe Ser Leu Val Tyr Ser Gly Asn
                245                 250                 255
Phe Leu Ala Gln Val Glu Val Asp Gln Phe His Thr Ala Arg Val Ser
            260                 265                 270
Leu Gly Ile Asn Pro Phe Asp Phe Thr Trp Leu Leu Glu Pro Gly Glu
        275                 280                 285
Ser Phe Gln Thr Pro Glu Val Val Met Val Tyr Ser Asp Gln Gly Leu
        290                 295                 300
Asn Gly Met Ser Gln Thr Phe His Arg Leu Tyr Arg Thr Arg Leu Ala
305                 310                 315                 320
Arg Gly Pro Phe Arg Asp Lys Glu Arg Pro Ile Leu Ile Asn Asn Trp
                325                 330                 335
Glu Ala Thr Tyr Phe Asp Phe Asn Glu Glu Lys Ile Leu Glu Ile Val
            340                 345                 350
Lys Ala Gly Lys Glu Leu Gly Ile Glu Leu Phe Val Leu Asp Asp Gly
        355                 360                 365
Trp Phe Gly Lys Arg Asp Asp Asp Lys Ser Ser Leu Gly Asp Trp Phe
        370                 375                 380
Val Asp Lys Arg Lys Leu Ser Asn Gly Leu Val Gly Leu Ala Thr Lys
385                 390                 395                 400
Ile Arg Glu Met Gly Met Gln Phe Gly Leu Trp Val Glu Pro Glu Met
                405                 410                 415
Ile Ser Ile Asp Ser Asp Leu Tyr Arg Lys His Pro Asp Trp Cys Leu
            420                 425                 430
His Val Pro Lys Arg Pro Arg Ser Glu Gly Arg Asn Gln Leu Ile Leu
        435                 440                 445
Asp Tyr Ser Arg Lys Glu Val Cys Asp Tyr Ile Ile Lys Val Met Ser
        450                 455                 460
Asp Ile Leu Ser Ser Ala Pro Ile Ser Tyr Val Lys Trp Asp Met Asn
465                 470                 475                 480
Arg His Met Thr Glu Ile Gly Ser Ala Ser Leu Pro Pro Glu Arg Gln
                485                 490                 495
Arg Glu Thr Ala His Arg Tyr Met Leu Gly Leu Tyr Arg Val Met Glu
            500                 505                 510
Glu Ile Thr Ser Lys Phe Pro His Val Leu Phe Glu Ser Cys Ser Gly
        515                 520                 525
Gly Gly Gly Arg Phe Asp Pro Gly Ile Leu Tyr Tyr Met Pro Gln Thr
        530                 535                 540
Trp Thr Ser Asp Asn Thr Asp Ala Ile Ser Arg Leu Lys Ile Gln Tyr
545                 550                 555                 560
Gly Thr Ser Ile Val Tyr Pro Ile Ser Ala Met Gly Ala His Val Ser
                565                 570                 575
Ala Val Pro Asn His Gln Val His Arg Ile Thr Ser Leu Asp Ile Arg
            580                 585                 590
Gly His Val Ala Met Ser Gly Asn Phe Gly Tyr Glu Leu Asp Leu Thr
        595                 600                 605
```

-continued

```
Lys Leu Thr Asp Glu Glu Lys Glu Lys Val Lys Glu Gln Val Ala Phe
610                 615                 620

Tyr Lys Glu Ile Arg Arg Leu Val Gln Tyr Gly Asn Phe Tyr Arg Ile
625                 630                 635                 640

Leu Ser Pro Phe Glu Gly Asn Glu Thr Ala Trp Met Phe Val Ser Glu
            645                 650                 655

Asp Gln Ser Glu Ala Phe Val Ala Tyr Phe Arg Val Leu Ala Glu Ala
                660                 665                 670

Asn Ala Pro Ile Ser Ser Ile Arg Leu Lys Gly Leu Asn Pro Arg Lys
            675                 680                 685

Gln Tyr Tyr Leu Val Gly Lys Gly Glu Val Tyr Gly Gly Asp Glu Leu
                690                 695                 700

Met Tyr Val Gly Ile Asn Ile Pro Tyr Ile Leu Gly Asp Phe Met Ser
705                 710                 715                 720

Phe Thr Trp Val Leu Lys Glu Trp Glu Lys Asp Phe His His His His
                    725                 730                 735

His His
```

```
<210> SEQ ID NO 10
<211> LENGTH: 2326
<212> TYPE: DNA
<213> ORGANISM: Aspergillus sydowii
<220> FEATURE:
<221> NAME/KEY: CDS
<222> LOCATION: (1)..(85)
<220> FEATURE:
<221> NAME/KEY: sig_peptide
<222> LOCATION: (1)..(69)
<220> FEATURE:
<221> NAME/KEY: mat_peptide
<222> LOCATION: (70)..(2364)
<220> FEATURE:
<221> NAME/KEY: CDS
<222> LOCATION: (131)..(734)
<220> FEATURE:
<221> NAME/KEY: CDS
<222> LOCATION: (787)..(2323)

<400> SEQUENCE: 10 atg gtt gcg ttt tct cct gtg gcc ctg ggc ctt ttg gcg ctt gcc agc      48
Met Val Ala Phe Ser Pro Val Ala Leu Gly Leu Leu Ala Leu Ala Ser
            -20                 -15                 -10 cac tcc aca atg gct tct gcg cag tcg gat tca gct g gttcgtattc         95
His Ser Thr Met Ala Ser Ala Gln Ser Asp Ser Ala
        -5                  -1  1               5 ctgaatgcct cgaggaaacg agactaattc tgtag tt  gtc gcc gat ggc act       147
                                          Val Val Ala Asp Gly Thr
                                                              10 acc ttc gcg ctg aat ggt gac aat gta tcc tac cga ttc cac gtc aac      195
Thr Phe Ala Leu Asn Gly Asp Asn Val Ser Tyr Arg Phe His Val Asn
            15                  20                  25 gag acc acc ggt gat ctt gta tcc gac cac ttt ggc ggc cgt gtc ggc      243
Glu Thr Thr Gly Asp Leu Val Ser Asp His Phe Gly Gly Arg Val Gly
        30                  35                  40 ggc gat atc ccc tcg ccc aag gaa cca gtc gtc aac ggc tgg gtc ggc      291
Gly Asp Ile Pro Ser Pro Lys Glu Pro Val Val Asn Gly Trp Val Gly
45                  50                  55 atg cct ggt cga atc cgg cgc gag ttc ccc gac cag ggc cgt ggc gac      339
Met Pro Gly Arg Ile Arg Arg Glu Phe Pro Asp Gln Gly Arg Gly Asp
60                  65                  70                  75 ttc cgc att cct gct gtt cgc att cgg cag tcg gct ggg tat act gtg      387
```

```
              Phe Arg Ile Pro Ala Val Arg Ile Arg Gln Ser Ala Gly Tyr Thr Val
                              80                  85                  90 agc gat ctg cag tat aaa tcg cac gag gtg gtt gag ggc aag agc ggg         435
Ser Asp Leu Gln Tyr Lys Ser His Glu Val Val Glu Gly Lys Ser Gly
            95                 100                 105 ctg cct gga ctg ccg gcg acc ttt ggg gac gca gag gat gtg acg acg         483
Leu Pro Gly Leu Pro Ala Thr Phe Gly Asp Ala Glu Asp Val Thr Thr
                110                 115                 120 cta gtt gtg cat ctt tat gac aat tat agc tct gtt gct gcg gat ttg         531
Leu Val Val His Leu Tyr Asp Asn Tyr Ser Ser Val Ala Ala Asp Leu
            125                 130                 135 tcg tac tcg atc ttt ccc aag tat gat gct gtg gtg agg agc gtc aat         579
Ser Tyr Ser Ile Phe Pro Lys Tyr Asp Ala Val Val Arg Ser Val Asn
140                 145                 150                 155 gtt acg aac aag ggc gag ggc aat atc act atc gag tcg ctg gcc agt         627
Val Thr Asn Lys Gly Glu Gly Asn Ile Thr Ile Glu Ser Leu Ala Ser
                160                 165                 170 ctg agc gtc gac ttt aac tat gag gat ctg gag atg atc agc cta cga         675
Leu Ser Val Asp Phe Asn Tyr Glu Asp Leu Glu Met Ile Ser Leu Arg
            175                 180                 185 ggc gac tgg gcc aga gaa gcg aat gtc cag agg agc aag atc gac tat         723
Gly Asp Trp Ala Arg Glu Ala Asn Val Gln Arg Ser Lys Ile Asp Tyr
                190                 195                 200 ggc gtg cat gg  gtatgttgcc gcaagattta tatcagacgg gctatactga             774
Gly Val His Gly
            205 ctgacagcac ag a ttc gga agc aac act ggc tac tcg tct cac ctg cac         823
                Phe Gly Ser Asn Thr Gly Tyr Ser Ser His Leu His
                                210                 215 aat ccc ttc ctc gca ata gtc gag cca tcg act acg gaa tcc caa ggc         871
Asn Pro Phe Leu Ala Ile Val Glu Pro Ser Thr Thr Glu Ser Gln Gly
220                 225                 230                 235 gag gca tgg ggc ttc aac ctc atc tac acc ggc tcc ttc tcc gct gaa         919
Glu Ala Trp Gly Phe Asn Leu Ile Tyr Thr Gly Ser Phe Ser Ala Glu
                240                 245                 250 gtc gaa aaa gga tcc caa ggt ctg acc cga gcc ctc ctc ggc ttc aac         967
Val Glu Lys Gly Ser Gln Gly Leu Thr Arg Ala Leu Leu Gly Phe Asn
            255                 260                 265 cct gac cgt cta tca tgg acc ctt ggc cct gac gag acc ctc acc acc        1015
Pro Asp Arg Leu Ser Trp Thr Leu Gly Pro Asp Glu Thr Leu Thr Thr
                270                 275                 280 cct gaa tgc gtt gca gtc tac tca aag aac ggt atc gga ggc atg tct        1063
Pro Glu Cys Val Ala Val Tyr Ser Lys Asn Gly Ile Gly Gly Met Ser
285                 290                 295 cgc aag ttc cac cgg ctc tac cgc aac cac ttg atc aag agc aag ttc        1111
Arg Lys Phe His Arg Leu Tyr Arg Asn His Leu Ile Lys Ser Lys Phe
                300                 305                 310                 315 gca aca tca gac cgc ccc gtc ctc ctc aac agc tgg gag ggc gtc tac        1159
Ala Thr Ser Asp Arg Pro Val Leu Leu Asn Ser Trp Glu Gly Val Tyr
                    320                 325                 330 ttc gac ttc aac cag agc atc atc gag act ctt gcc gag caa tcc gcc        1207
Phe Asp Phe Asn Gln Ser Ile Ile Glu Thr Leu Ala Glu Gln Ser Ala
                335                 340                 345 gct cta gga atc cac ctg ttc gtc atg gat gac ggc tgg ttc ggt gac        1255
Ala Leu Gly Ile His Leu Phe Val Met Asp Asp Gly Trp Phe Gly Asp
                350                 355                 360 aag tac ccc aga act tca gac aac gcg ggc ctg ggc gac tgg aca ccc        1303
Lys Tyr Pro Arg Thr Ser Asp Asn Ala Gly Leu Gly Asp Trp Thr Pro
365                 370                 375
```

```
aac cca gat cgc ttc cca gac ggt ctc tcc ccg gtc gta gaa gac atc    1351
Asn Pro Asp Arg Phe Pro Asp Gly Leu Ser Pro Val Val Glu Asp Ile
380             385                 390                 395 aca agc atg tcc gtc aat gga aca caa gat aca aag ctc cgc ttc gga    1399
Thr Ser Met Ser Val Asn Gly Thr Gln Asp Thr Lys Leu Arg Phe Gly
                400                 405                 410 atc tgg gtc gag ccc gag atg gtc aat ccc aac tcc agc ctg tac cgt    1447
Ile Trp Val Glu Pro Glu Met Val Asn Pro Asn Ser Ser Leu Tyr Arg
            415                 420                 425 gaa cat ccg gac tgg gtc ctc cac gca ggg ccc tac cca cgc aca gaa    1495
Glu His Pro Asp Trp Val Leu His Ala Gly Pro Tyr Pro Arg Thr Glu
        430                 435                 440 cga cgc aac caa ctt gtc ttg aac gtc gcc ttg cca gag gtc cag gac    1543
Arg Arg Asn Gln Leu Val Leu Asn Val Ala Leu Pro Glu Val Gln Asp
    445                 450                 455 ttc atc atc gac ttc atg aca aac ctg ctg aat ggt tcc gac att tcc    1591
Phe Ile Ile Asp Phe Met Thr Asn Leu Leu Asn Gly Ser Asp Ile Ser
460                 465                 470                 475 tac ata aaa tgg gac aat aac cgc gga atg cac gag aca cca tcc ccg    1639
Tyr Ile Lys Trp Asp Asn Asn Arg Gly Met His Glu Thr Pro Ser Pro
                480                 485                 490 agc aac gac cac aag tac atg ctc ggc ctc tac cgc gtc ttc gac aca    1687
Ser Asn Asp His Lys Tyr Met Leu Gly Leu Tyr Arg Val Phe Asp Thr
            495                 500                 505 ttg acc acc cgt ttc gcc gac gtc ctc tgg gaa gga tgc gcc tca ggc    1735
Leu Thr Thr Arg Phe Ala Asp Val Leu Trp Glu Gly Cys Ala Ser Gly
        510                 515                 520 ggt ggg cgc ttc gat gcc ggc gtc ctg cag tac ttc ccc cag atc tgg    1783
Gly Gly Arg Phe Asp Ala Gly Val Leu Gln Tyr Phe Pro Gln Ile Trp
    525                 530                 535 acc tcc gat aac acc gac ggg gtc gac aga gtc acc atc caa ttc ggg    1831
Thr Ser Asp Asn Thr Asp Gly Val Asp Arg Val Thr Ile Gln Phe Gly
540                 545                 550                 555 acc tcc ctt gca tac cct ccc tcg gcg atg ggg gcg cat ctc tcg gcc    1879
Thr Ser Leu Ala Tyr Pro Pro Ser Ala Met Gly Ala His Leu Ser Ala
                560                 565                 570 gta cca aac cac caa aca ggc cgg acc gtg ccg atg gaa ttc cgc gcg    1927
Val Pro Asn His Gln Thr Gly Arg Thr Val Pro Met Glu Phe Arg Ala
            575                 580                 585 cac gtc gca atg atg ggc ggg tca ttc ggg ctg gaa ctc gac ccg gcc    1975
His Val Ala Met Met Gly Gly Ser Phe Gly Leu Glu Leu Asp Pro Ala
        590                 595                 600 acg atc cag aat aac acc gcc gtg ccg gaa ctg ttg aag ctg gcg gag    2023
Thr Ile Gln Asn Asn Thr Ala Val Pro Glu Leu Leu Lys Leu Ala Glu
    605                 610                 615 aag att aac ccg att atc ctg act ggg gat ctg tat cgg ttg agg gca    2071
Lys Ile Asn Pro Ile Ile Leu Thr Gly Asp Leu Tyr Arg Leu Arg Ala
620                 625                 630                 635 ccc gag gac tcg cag tgg ccg gct gcg ttg ttt gtg gcg gag gat ggg    2119
Pro Glu Asp Ser Gln Trp Pro Ala Ala Leu Phe Val Ala Glu Asp Gly
                640                 645                 650 tcc cag gct gtg ctg ttt tat ttc cag ctt agt ccg aat gtc aac cat    2167
Ser Gln Ala Val Leu Phe Tyr Phe Gln Leu Ser Pro Asn Val Asn His
            655                 660                 665 gcg gcg ccg tgg gtg aag ctt cag ggg ttg gat gag acg gcg caa tat    2215
Ala Ala Pro Trp Val Lys Leu Gln Gly Leu Asp Glu Thr Ala Gln Tyr
        670                 675                 680 aag gtc gag gga gag ggg aca ttc tct ggc gcg acg ctg atg aat atg    2263
Lys Val Glu Gly Glu Gly Thr Phe Ser Gly Ala Thr Leu Met Asn Met
    685                 690                 695
```

```
ggg ctg cag tat acg ttt gat acg gag tat ggc agt aag gtg gtg gtt      2311
Gly Leu Gln Tyr Thr Phe Asp Thr Glu Tyr Gly Ser Lys Val Val Val
700                 705                 710                 715 att gag agg cag tag                                                   2326
Ile Glu Arg Gln
```

<210> SEQ ID NO 11
<211> LENGTH: 742
<212> TYPE: PRT
<213> ORGANISM: Aspergillus sydowii

<400> SEQUENCE: 11

```
Met Val Ala Phe Ser Pro Val Ala Leu Gly Leu Leu Ala Leu Ala Ser
                -20                 -15                 -10

His Ser Thr Met Ala Ser Ala Gln Ser Asp Ser Ala Val Val Ala Asp
        -5              -1  1                   5

Gly Thr Thr Phe Ala Leu Asn Gly Asp Asn Val Ser Tyr Arg Phe His
10                  15                  20                  25

Val Asn Glu Thr Thr Gly Asp Leu Val Ser Asp His Phe Gly Gly Arg
                30                  35                  40

Val Gly Gly Asp Ile Pro Ser Pro Lys Glu Pro Val Val Asn Gly Trp
            45                  50                  55

Val Gly Met Pro Gly Arg Ile Arg Arg Glu Phe Pro Asp Gln Gly Arg
        60                  65                  70

Gly Asp Phe Arg Ile Pro Ala Val Arg Ile Arg Gln Ser Ala Gly Tyr
    75                  80                  85

Thr Val Ser Asp Leu Gln Tyr Lys Ser His Glu Val Val Glu Gly Lys
90                  95                  100                 105

Ser Gly Leu Pro Gly Leu Pro Ala Thr Phe Gly Asp Ala Glu Asp Val
                110                 115                 120

Thr Thr Leu Val Val His Leu Tyr Asp Asn Tyr Ser Ser Val Ala Ala
            125                 130                 135

Asp Leu Ser Tyr Ser Ile Phe Pro Lys Tyr Asp Ala Val Val Arg Ser
        140                 145                 150

Val Asn Val Thr Asn Lys Gly Glu Gly Asn Ile Thr Ile Glu Ser Leu
    155                 160                 165

Ala Ser Leu Ser Val Asp Phe Asn Tyr Glu Asp Leu Glu Met Ile Ser
170                 175                 180                 185

Leu Arg Gly Asp Trp Ala Arg Glu Ala Asn Val Gln Arg Ser Lys Ile
                190                 195                 200

Asp Tyr Gly Val His Gly Phe Gly Ser Asn Thr Gly Tyr Ser Ser His
            205                 210                 215

Leu His Asn Pro Phe Leu Ala Ile Val Glu Pro Ser Thr Thr Glu Ser
        220                 225                 230

Gln Gly Glu Ala Trp Gly Phe Asn Leu Ile Tyr Thr Gly Ser Phe Ser
    235                 240                 245

Ala Glu Val Glu Lys Gly Ser Gln Gly Leu Thr Arg Ala Leu Leu Gly
250                 255                 260                 265

Phe Asn Pro Asp Arg Leu Ser Trp Thr Leu Gly Pro Asp Glu Thr Leu
                270                 275                 280

Thr Thr Pro Glu Cys Val Ala Val Tyr Ser Lys Asn Gly Ile Gly Gly
            285                 290                 295

Met Ser Arg Lys Phe His Arg Leu Tyr Arg Asn His Leu Ile Lys Ser
        300                 305                 310
```

```
Lys Phe Ala Thr Ser Asp Arg Pro Val Leu Leu Asn Ser Trp Glu Gly
315                 320                 325
Val Tyr Phe Asp Phe Asn Gln Ser Ile Ile Glu Thr Leu Ala Glu Gln
330                 335                 340                 345
Ser Ala Ala Leu Gly Ile His Leu Phe Val Met Asp Asp Gly Trp Phe
            350                 355                 360
Gly Asp Lys Tyr Pro Arg Thr Ser Asp Asn Ala Gly Leu Gly Asp Trp
        365                 370                 375
Thr Pro Asn Pro Asp Arg Phe Pro Asp Gly Leu Ser Pro Val Val Glu
    380                 385                 390
Asp Ile Thr Ser Met Ser Val Asn Gly Thr Gln Asp Thr Lys Leu Arg
395                 400                 405
Phe Gly Ile Trp Val Glu Pro Glu Met Val Asn Pro Asn Ser Ser Leu
410                 415                 420                 425
Tyr Arg Glu His Pro Asp Trp Val Leu His Ala Gly Pro Tyr Pro Arg
                430                 435                 440
Thr Glu Arg Arg Asn Gln Leu Val Leu Asn Val Ala Leu Pro Glu Val
            445                 450                 455
Gln Asp Phe Ile Ile Asp Phe Met Thr Asn Leu Leu Asn Gly Ser Asp
        460                 465                 470
Ile Ser Tyr Ile Lys Trp Asp Asn Asn Arg Gly Met His Glu Thr Pro
475                 480                 485
Ser Pro Ser Asn Asp His Lys Tyr Met Leu Gly Leu Tyr Arg Val Phe
490                 495                 500                 505
Asp Thr Leu Thr Thr Arg Phe Ala Asp Val Leu Trp Glu Gly Cys Ala
                510                 515                 520
Ser Gly Gly Gly Arg Phe Asp Ala Gly Val Leu Gln Tyr Phe Pro Gln
            525                 530                 535
Ile Trp Thr Ser Asp Asn Thr Asp Gly Val Asp Arg Val Thr Ile Gln
        540                 545                 550
Phe Gly Thr Ser Leu Ala Tyr Pro Pro Ser Ala Met Gly Ala His Leu
555                 560                 565
Ser Ala Val Pro Asn His Gln Thr Gly Arg Thr Val Pro Met Glu Phe
570                 575                 580                 585
Arg Ala His Val Ala Met Met Gly Gly Ser Phe Gly Leu Glu Leu Asp
                590                 595                 600
Pro Ala Thr Ile Gln Asn Asn Thr Ala Val Pro Glu Leu Leu Lys Leu
            605                 610                 615
Ala Glu Lys Ile Asn Pro Ile Ile Leu Thr Gly Asp Leu Tyr Arg Leu
        620                 625                 630
Arg Ala Pro Glu Asp Ser Gln Trp Pro Ala Ala Leu Phe Val Ala Glu
635                 640                 645
Asp Gly Ser Gln Ala Val Leu Phe Tyr Phe Gln Leu Ser Pro Asn Val
650                 655                 660                 665
Asn His Ala Ala Pro Trp Val Lys Leu Gln Gly Leu Asp Glu Thr Ala
                670                 675                 680
Gln Tyr Lys Val Glu Gly Gly Thr Phe Ser Gly Ala Thr Leu Met
            685                 690                 695
Asn Met Gly Leu Gln Tyr Thr Phe Asp Thr Glu Tyr Gly Ser Lys Val
        700                 705                 710
Val Val Ile Glu Arg Gln
    715
```

```
<210> SEQ ID NO 12
<211> LENGTH: 719
<212> TYPE: PRT
<213> ORGANISM: Aspergillus sydowii
<220> FEATURE:
<221> NAME/KEY: mat_peptide
<222> LOCATION: (1)..(719)

<400> SEQUENCE: 12
```

| | | | | | | | | | | | | | | |
|---|---|---|---|---|---|---|---|---|---|---|---|---|---|---|
| Gln | Ser | Asp | Ser | Ala | Val | Val | Ala | Asp | Gly | Thr | Thr | Phe | Ala | Leu | Asn |
| 1 | | | | 5 | | | | | 10 | | | | | 15 | |
| Gly | Asp | Asn | Val | Ser | Tyr | Arg | Phe | His | Val | Asn | Glu | Thr | Thr | Gly | Asp |
| | | | 20 | | | | | 25 | | | | | 30 | | |
| Leu | Val | Ser | Asp | His | Phe | Gly | Gly | Arg | Val | Gly | Gly | Asp | Ile | Pro | Ser |
| | | 35 | | | | | 40 | | | | | 45 | | | |
| Pro | Lys | Glu | Pro | Val | Val | Asn | Gly | Trp | Val | Gly | Met | Pro | Gly | Arg | Ile |
| | 50 | | | | | 55 | | | | | 60 | | | | |
| Arg | Arg | Glu | Phe | Pro | Asp | Gln | Gly | Arg | Gly | Asp | Phe | Arg | Ile | Pro | Ala |
| 65 | | | | | 70 | | | | | 75 | | | | | 80 |
| Val | Arg | Ile | Arg | Gln | Ser | Ala | Gly | Tyr | Thr | Val | Ser | Asp | Leu | Gln | Tyr |
| | | | | 85 | | | | | 90 | | | | | 95 | |
| Lys | Ser | His | Glu | Val | Val | Glu | Gly | Lys | Ser | Gly | Leu | Pro | Gly | Leu | Pro |
| | | | 100 | | | | | 105 | | | | | 110 | | |
| Ala | Thr | Phe | Gly | Asp | Ala | Glu | Asp | Val | Thr | Thr | Leu | Val | Val | His | Leu |
| | | 115 | | | | | 120 | | | | | 125 | | | |
| Tyr | Asp | Asn | Tyr | Ser | Ser | Val | Ala | Ala | Asp | Leu | Ser | Tyr | Ser | Ile | Phe |
| | 130 | | | | | 135 | | | | | 140 | | | | |
| Pro | Lys | Tyr | Asp | Ala | Val | Val | Arg | Ser | Val | Asn | Val | Thr | Asn | Lys | Gly |
| 145 | | | | | 150 | | | | | 155 | | | | | 160 |
| Glu | Gly | Asn | Ile | Thr | Ile | Glu | Ser | Leu | Ala | Ser | Leu | Ser | Val | Asp | Phe |
| | | | | 165 | | | | | 170 | | | | | 175 | |
| Asn | Tyr | Glu | Asp | Leu | Glu | Met | Ile | Ser | Leu | Arg | Gly | Asp | Trp | Ala | Arg |
| | | | 180 | | | | | 185 | | | | | 190 | | |
| Glu | Ala | Asn | Val | Gln | Arg | Ser | Lys | Ile | Asp | Tyr | Gly | Val | His | Gly | Phe |
| | | 195 | | | | | 200 | | | | | 205 | | | |
| Gly | Ser | Asn | Thr | Gly | Tyr | Ser | Ser | His | Leu | His | Asn | Pro | Phe | Leu | Ala |
| | 210 | | | | | 215 | | | | | 220 | | | | |
| Ile | Val | Glu | Pro | Ser | Thr | Thr | Glu | Ser | Gln | Gly | Glu | Ala | Trp | Gly | Phe |
| 225 | | | | | 230 | | | | | 235 | | | | | 240 |
| Asn | Leu | Ile | Tyr | Thr | Gly | Ser | Phe | Ser | Ala | Glu | Val | Glu | Lys | Gly | Ser |
| | | | | 245 | | | | | 250 | | | | | 255 | |
| Gln | Gly | Leu | Thr | Arg | Ala | Leu | Leu | Gly | Phe | Asn | Pro | Asp | Arg | Leu | Ser |
| | | | 260 | | | | | 265 | | | | | 270 | | |
| Trp | Thr | Leu | Gly | Pro | Asp | Glu | Thr | Leu | Thr | Thr | Pro | Glu | Cys | Val | Ala |
| | | 275 | | | | | 280 | | | | | 285 | | | |
| Val | Tyr | Ser | Lys | Asn | Gly | Ile | Gly | Gly | Met | Ser | Arg | Lys | Phe | His | Arg |
| | 290 | | | | | 295 | | | | | 300 | | | | |
| Leu | Tyr | Arg | Asn | His | Leu | Ile | Lys | Ser | Lys | Phe | Ala | Thr | Ser | Asp | Arg |
| 305 | | | | | 310 | | | | | 315 | | | | | 320 |
| Pro | Val | Leu | Leu | Asn | Ser | Trp | Glu | Gly | Val | Tyr | Phe | Asp | Phe | Asn | Gln |
| | | | | 325 | | | | | 330 | | | | | 335 | |
| Ser | Ile | Ile | Glu | Thr | Leu | Ala | Glu | Gln | Ser | Ala | Ala | Leu | Gly | Ile | His |
| | | | 340 | | | | | 345 | | | | | 350 | | |
| Leu | Phe | Val | Met | Asp | Asp | Gly | Trp | Phe | Gly | Asp | Lys | Tyr | Pro | Arg | Thr |
| | | 355 | | | | | 360 | | | | | 365 | | | |

Ser Asp Asn Ala Gly Leu Gly Asp Trp Thr Pro Asn Pro Asp Arg Phe
370                 375                 380

Pro Asp Gly Leu Ser Pro Val Val Glu Asp Ile Thr Ser Met Ser Val
385                 390                 395                 400

Asn Gly Thr Gln Asp Thr Lys Leu Arg Phe Gly Ile Trp Val Glu Pro
            405                 410                 415

Glu Met Val Asn Pro Asn Ser Ser Leu Tyr Arg Glu His Pro Asp Trp
            420                 425                 430

Val Leu His Ala Gly Pro Tyr Pro Arg Thr Glu Arg Asn Gln Leu
            435                 440                 445

Val Leu Asn Val Ala Leu Pro Glu Val Gln Asp Phe Ile Ile Asp Phe
450                 455                 460

Met Thr Asn Leu Leu Asn Gly Ser Asp Ile Ser Tyr Ile Lys Trp Asp
465                 470                 475                 480

Asn Asn Arg Gly Met His Glu Thr Pro Ser Pro Ser Asn Asp His Lys
            485                 490                 495

Tyr Met Leu Gly Leu Tyr Arg Val Phe Asp Thr Leu Thr Thr Arg Phe
            500                 505                 510

Ala Asp Val Leu Trp Glu Gly Cys Ala Ser Gly Gly Gly Arg Phe Asp
515                 520                 525

Ala Gly Val Leu Gln Tyr Phe Pro Gln Ile Trp Thr Ser Asp Asn Thr
530                 535                 540

Asp Gly Val Asp Arg Val Thr Ile Gln Phe Gly Thr Ser Leu Ala Tyr
545                 550                 555                 560

Pro Pro Ser Ala Met Gly Ala His Leu Ser Ala Val Pro Asn His Gln
            565                 570                 575

Thr Gly Arg Thr Val Pro Met Glu Phe Arg Ala His Val Ala Met Met
            580                 585                 590

Gly Gly Ser Phe Gly Leu Glu Leu Asp Pro Ala Thr Ile Gln Asn Asn
            595                 600                 605

Thr Ala Val Pro Glu Leu Leu Lys Leu Ala Glu Lys Ile Asn Pro Ile
610                 615                 620

Ile Leu Thr Gly Asp Leu Tyr Arg Leu Arg Ala Pro Glu Asp Ser Gln
625                 630                 635                 640

Trp Pro Ala Ala Leu Phe Val Ala Glu Asp Gly Ser Gln Ala Val Leu
            645                 650                 655

Phe Tyr Phe Gln Leu Ser Pro Asn Val Asn His Ala Ala Pro Trp Val
            660                 665                 670

Lys Leu Gln Gly Leu Asp Glu Thr Ala Gln Tyr Lys Val Glu Gly Glu
            675                 680                 685

Gly Thr Phe Ser Gly Ala Thr Leu Met Asn Met Gly Leu Gln Tyr Thr
            690                 695                 700

Phe Asp Thr Glu Tyr Gly Ser Lys Val Val Val Ile Glu Arg Gln
705                 710                 715

<210> SEQ ID NO 13
<211> LENGTH: 2196
<212> TYPE: DNA
<213> ORGANISM: Bacillus sp-19140
<220> FEATURE:
<221> NAME/KEY: CDS
<222> LOCATION: (1)..(2193)
<220> FEATURE:
<221> NAME/KEY: mat_peptide
<222> LOCATION: (1)..(2193)

<400> SEQUENCE: 13

```
atg gga att aca tat caa gag gaa ggg caa atc ttc cat ctg caa gga        48
Met Gly Ile Thr Tyr Gln Glu Glu Gly Gln Ile Phe His Leu Gln Gly
1               5                   10                  15 aaa gat acg agt tac gtt atg cag gta tta aag gat ggc tat ttg acc        96
Lys Asp Thr Ser Tyr Val Met Gln Val Leu Lys Asp Gly Tyr Leu Thr
                20                  25                  30 cat ctc tac tgg ggg aaa cgt gtg agg ggc tac aat caa agt atc cca       144
His Leu Tyr Trp Gly Lys Arg Val Arg Gly Tyr Asn Gln Ser Ile Pro
            35                  40                  45 gtg aca ttt ttt gac cga gga ttt tcg gcc aat cca gat ccg act gat       192
Val Thr Phe Phe Asp Arg Gly Phe Ser Ala Asn Pro Asp Pro Thr Asp
        50                  55                  60 cgg acg ttc tct ttg gat acg tta cct caa gag tac cct gct tac ggg       240
Arg Thr Phe Ser Leu Asp Thr Leu Pro Gln Glu Tyr Pro Ala Tyr Gly
65                  70                  75                  80 aat aca gat ttc cga acc cct gcg tat caa att caa ttg gaa aat ggt       288
Asn Thr Asp Phe Arg Thr Pro Ala Tyr Gln Ile Gln Leu Glu Asn Gly
                85                  90                  95 tct acc atc tca gat tta cgt tat agc tcg cat aaa atc tat aaa ggt       336
Ser Thr Ile Ser Asp Leu Arg Tyr Ser Ser His Lys Ile Tyr Lys Gly
            100                 105                 110 aaa cca aaa ctt gag ggg ctt cca tca act tat gcg gaa cgc gat gaa       384
Lys Pro Lys Leu Glu Gly Leu Pro Ser Thr Tyr Ala Glu Arg Asp Glu
        115                 120                 125 gaa gcg gag aca tta gaa atc atc ctt gaa gat gat act att ggc ttg       432
Glu Ala Glu Thr Leu Glu Ile Ile Leu Glu Asp Asp Thr Ile Gly Leu
130                 135                 140 aaa gta acc ctc atc tat aca gtt ttt gaa gcg tat aac gca ctt act       480
Lys Val Thr Leu Ile Tyr Thr Val Phe Glu Ala Tyr Asn Ala Leu Thr
145                 150                 155                 160 cga tct gtt cgt ttt gaa aac agt ggt cgt acg gta att aaa ttg tta       528
Arg Ser Val Arg Phe Glu Asn Ser Gly Arg Thr Val Ile Lys Leu Leu
                165                 170                 175 agg gcg ctt tcg ctt aat tta gat ttt cgc gac caa gat ttt gaa tta       576
Arg Ala Leu Ser Leu Asn Leu Asp Phe Arg Asp Gln Asp Phe Glu Leu
            180                 185                 190 att act tta tat ggt tct cac aat aat gaa cgt aac ctt gct agg cgg       624
Ile Thr Leu Tyr Gly Ser His Asn Asn Glu Arg Asn Leu Ala Arg Arg
        195                 200                 205 cca gtg gct cca gga ctt caa gca att gaa agc agg aga ggg gcg agc       672
Pro Val Ala Pro Gly Leu Gln Ala Ile Glu Ser Arg Arg Gly Ala Ser
210                 215                 220 agt cac caa caa aat cct ttt cta gct ttg gtg aga cca act tca acg       720
Ser His Gln Gln Asn Pro Phe Leu Ala Leu Val Arg Pro Thr Ser Thr
225                 230                 235                 240 gaa gac agt gga gaa gtt ttt gct tta aat tta gtt tac agc ggg aat       768
Glu Asp Ser Gly Glu Val Phe Ala Leu Asn Leu Val Tyr Ser Gly Asn
                245                 250                 255 ttt ctt ggg cag gtg gaa gtc aac caa ttt aaa acc acc agg ttg tcc       816
Phe Leu Gly Gln Val Glu Val Asn Gln Phe Lys Thr Thr Arg Leu Ser
            260                 265                 270 tta gga att aat ccc ttt gat ttc act tgg caa cta aac cct aag gaa       864
Leu Gly Ile Asn Pro Phe Asp Phe Thr Trp Gln Leu Asn Pro Lys Glu
        275                 280                 285 gcc ttt caa act cct gaa gca gtt atg gtt tat tct tca aat gga tta       912
Ala Phe Gln Thr Pro Glu Ala Val Met Val Tyr Ser Ser Asn Gly Leu
290                 295                 300 aac gaa atg tcg caa act ttt cat gat ctc tat acg aat cgt ctt tgc       960
Asn Glu Met Ser Gln Thr Phe His Asp Leu Tyr Thr Asn Arg Leu Cys
```

```
                305                 310                 315                 320
cgg ggc cag ttc cgg aat caa att cgc cca att ctt att aat aat tgg    1008
Arg Gly Gln Phe Arg Asn Gln Ile Arg Pro Ile Leu Ile Asn Asn Trp
                    325                 330                 335 gaa gca act tat ttt aat ttt aat gcg gaa aaa gtt ctt gag att gca    1056
Glu Ala Thr Tyr Phe Asn Phe Asn Ala Glu Lys Val Leu Glu Ile Ala
            340                 345                 350 aaa gtg gga aaa gag ctt ggg atg gaa tta gtt gta ctg gat gac ggt    1104
Lys Val Gly Lys Glu Leu Gly Met Glu Leu Val Val Leu Asp Asp Gly
        355                 360                 365 tgg ttc ggt gaa cgt gat gat gat tgt cgt tca ctt ggc gat tgg gtg    1152
Trp Phe Gly Glu Arg Asp Asp Asp Cys Arg Ser Leu Gly Asp Trp Val
    370                 375                 380 gtt gat cgc agg aag ctg ccg gat ggc ctt gat aat ctt gca aaa cgt    1200
Val Asp Arg Arg Lys Leu Pro Asp Gly Leu Asp Asn Leu Ala Lys Arg
385                 390                 395                 400 gtc agg gag atg ggt tta gag ttt gga tta tgg ttt gag cct gag atg    1248
Val Arg Glu Met Gly Leu Glu Phe Gly Leu Trp Phe Glu Pro Glu Met
                    405                 410                 415 gtt tca gtt aac agt aat tta tat cgt gag cat cca gac tgg tgt ttg    1296
Val Ser Val Asn Ser Asn Leu Tyr Arg Glu His Pro Asp Trp Cys Leu
            420                 425                 430 cat gtt cca aac cgt cca aaa agt gaa agt cga aac cag ctc att tta    1344
His Val Pro Asn Arg Pro Lys Ser Glu Ser Arg Asn Gln Leu Ile Leu
        435                 440                 445 gat tta tct cgt cag gaa gtt tgc gag tat gtg att gaa tct gtt tcg    1392
Asp Leu Ser Arg Gln Glu Val Cys Glu Tyr Val Ile Glu Ser Val Ser
    450                 455                 460 tct att ctt tca act gtt cct att tct tat gta aag tgg gat atg aac    1440
Ser Ile Leu Ser Thr Val Pro Ile Ser Tyr Val Lys Trp Asp Met Asn
465                 470                 475                 480 cgg cat atg aca gaa gtt ggg tca gca gat ctt cca gcg gag cgg cag    1488
Arg His Met Thr Glu Val Gly Ser Ala Asp Leu Pro Ala Glu Arg Gln
                    485                 490                 495 cgt gaa acg gct cac cgt tat atg cta gga ctt tat cgc gta ctc gag    1536
Arg Glu Thr Ala His Arg Tyr Met Leu Gly Leu Tyr Arg Val Leu Glu
            500                 505                 510 gct ata acc tct cgt ttt cct aat gtg ttg ttt gaa agc tgt tct gga    1584
Ala Ile Thr Ser Arg Phe Pro Asn Val Leu Phe Glu Ser Cys Ser Gly
        515                 520                 525 ggg gga ggt cgc ttt gat cca gga ttc cta tat tat atg ccg caa acc    1632
Gly Gly Gly Arg Phe Asp Pro Gly Phe Leu Tyr Tyr Met Pro Gln Thr
    530                 535                 540 tgg acc agc gat aat aca gat gcg gtt agc cgc ttg aaa atc caa tac    1680
Trp Thr Ser Asp Asn Thr Asp Ala Val Ser Arg Leu Lys Ile Gln Tyr
545                 550                 555                 560 gga acg agc ctt gcc tat cca ata agt tct atg ggt tct cat gtt tcc    1728
Gly Thr Ser Leu Ala Tyr Pro Ile Ser Ser Met Gly Ser His Val Ser
                    565                 570                 575 gct gtt cct aat cat cag ctt cat cgt tca aca cct att gaa aca aga    1776
Ala Val Pro Asn His Gln Leu His Arg Ser Thr Pro Ile Glu Thr Arg
            580                 585                 590 ggg gat gtg gca atg tcc ggg aac ctg gga tat gag ctt gat tta aca    1824
Gly Asp Val Ala Met Ser Gly Asn Leu Gly Tyr Glu Leu Asp Leu Thr
        595                 600                 605 aag ctt tca gat caa gaa aaa gag gcg gta aaa gcc cag att tcc ttc    1872
Lys Leu Ser Asp Gln Glu Lys Glu Ala Val Lys Ala Gln Ile Ser Phe
    610                 615                 620 tat aaa gac att cgt gaa gtt att cag ttt gga aag ttt tac agg att    1920
```

```
Tyr Lys Asp Ile Arg Glu Val Ile Gln Phe Gly Lys Phe Tyr Arg Ile
625                 630                 635                 640 tta agc cca ttc gaa gga aat gaa gca ggt tgg gta ttt gtg tca cat    1968
Leu Ser Pro Phe Glu Gly Asn Glu Ala Gly Trp Val Phe Val Ser His
                    645                 650                 655 gat caa tct gaa tgt gtt gca gga tat ttc aga gtg ttg gcg gaa cct    2016
Asp Gln Ser Glu Cys Val Ala Gly Tyr Phe Arg Val Leu Ala Glu Pro
                660                 665                 670 tat gaa cca acc aaa att tta aaa ata aag ggg ctt aat cca gaa ttg    2064
Tyr Glu Pro Thr Lys Ile Leu Lys Ile Lys Gly Leu Asn Pro Glu Leu
            675                 680                 685 aat tat cgt tta gct gga act gag caa gtc ttc ggc ggt gat gag ctt    2112
Asn Tyr Arg Leu Ala Gly Thr Glu Gln Val Phe Gly Gly Asp Glu Leu
        690                 695                 700 atg ttc atg ggt tta aat ata cct gac tta aaa ggt gat ttt agg agt    2160
Met Phe Met Gly Leu Asn Ile Pro Asp Leu Lys Gly Asp Phe Arg Ser
705                 710                 715                 720 gtt ctt tgg cac ttt aag gca ggg tct att cat taa                    2196
Val Leu Trp His Phe Lys Ala Gly Ser Ile His
                    725                 730

<210> SEQ ID NO 14
<211> LENGTH: 731
<212> TYPE: PRT
<213> ORGANISM: Bacillus sp-19140

<400> SEQUENCE: 14

Met Gly Ile Thr Tyr Gln Glu Glu Gly Gln Ile Phe His Leu Gln Gly
1               5                   10                  15

Lys Asp Thr Ser Tyr Val Met Gln Val Leu Lys Asp Gly Tyr Leu Thr
            20                  25                  30

His Leu Tyr Trp Gly Lys Arg Val Arg Gly Tyr Asn Gln Ser Ile Pro
        35                  40                  45

Val Thr Phe Phe Asp Arg Gly Phe Ser Ala Asn Pro Asp Pro Thr Asp
    50                  55                  60

Arg Thr Phe Ser Leu Asp Thr Leu Pro Gln Glu Tyr Pro Ala Tyr Gly
65                  70                  75                  80

Asn Thr Asp Phe Arg Thr Pro Ala Tyr Gln Ile Gln Leu Glu Asn Gly
                85                  90                  95

Ser Thr Ile Ser Asp Leu Arg Tyr Ser Ser His Lys Ile Tyr Lys Gly
            100                 105                 110

Lys Pro Lys Leu Glu Gly Leu Pro Ser Thr Tyr Ala Glu Arg Asp Glu
        115                 120                 125

Glu Ala Glu Thr Leu Glu Ile Ile Leu Glu Asp Asp Thr Ile Gly Leu
    130                 135                 140

Lys Val Thr Leu Ile Tyr Thr Val Phe Glu Ala Tyr Asn Ala Leu Thr
145                 150                 155                 160

Arg Ser Val Arg Phe Glu Asn Ser Gly Arg Thr Val Ile Lys Leu Leu
                165                 170                 175

Arg Ala Leu Ser Leu Asn Leu Asp Phe Arg Asp Gln Asp Phe Glu Leu
            180                 185                 190

Ile Thr Leu Tyr Gly Ser His Asn Asn Glu Arg Asn Leu Ala Arg Arg
        195                 200                 205

Pro Val Ala Pro Gly Leu Gln Ala Ile Glu Ser Arg Arg Gly Ala Ser
    210                 215                 220

Ser His Gln Gln Asn Pro Phe Leu Ala Leu Val Arg Pro Thr Ser Thr
225                 230                 235                 240
```

```
Glu Asp Ser Gly Glu Val Phe Ala Leu Asn Leu Val Tyr Ser Gly Asn
                245                 250                 255

Phe Leu Gly Gln Val Glu Val Asn Gln Phe Lys Thr Thr Arg Leu Ser
            260                 265                 270

Leu Gly Ile Asn Pro Phe Asp Phe Thr Trp Gln Leu Asn Pro Lys Glu
        275                 280                 285

Ala Phe Gln Thr Pro Glu Ala Val Met Val Tyr Ser Ser Asn Gly Leu
    290                 295                 300

Asn Glu Met Ser Gln Thr Phe His Asp Leu Tyr Thr Asn Arg Leu Cys
305                 310                 315                 320

Arg Gly Gln Phe Arg Asn Gln Ile Arg Pro Ile Leu Ile Asn Asn Trp
                325                 330                 335

Glu Ala Thr Tyr Phe Asn Phe Asn Ala Glu Lys Val Leu Glu Ile Ala
            340                 345                 350

Lys Val Gly Lys Glu Leu Gly Met Glu Leu Val Val Leu Asp Asp Gly
        355                 360                 365

Trp Phe Gly Glu Arg Asp Asp Cys Arg Ser Leu Gly Asp Trp Val
    370                 375                 380

Val Asp Arg Arg Lys Leu Pro Asp Gly Leu Asp Asn Leu Ala Lys Arg
385                 390                 395                 400

Val Arg Glu Met Gly Leu Glu Phe Gly Leu Trp Phe Glu Pro Glu Met
                405                 410                 415

Val Ser Val Asn Ser Asn Leu Tyr Arg Glu His Pro Asp Trp Cys Leu
            420                 425                 430

His Val Pro Asn Arg Pro Lys Ser Glu Ser Arg Asn Gln Leu Ile Leu
        435                 440                 445

Asp Leu Ser Arg Gln Glu Val Cys Glu Tyr Val Ile Glu Ser Val Ser
    450                 455                 460

Ser Ile Leu Ser Thr Val Pro Ile Ser Tyr Val Lys Trp Asp Met Asn
465                 470                 475                 480

Arg His Met Thr Glu Val Gly Ser Ala Asp Leu Pro Ala Glu Arg Gln
                485                 490                 495

Arg Glu Thr Ala His Arg Tyr Met Leu Gly Leu Tyr Arg Val Leu Glu
            500                 505                 510

Ala Ile Thr Ser Arg Phe Pro Asn Val Leu Phe Glu Ser Cys Ser Gly
        515                 520                 525

Gly Gly Gly Arg Phe Asp Pro Gly Phe Leu Tyr Tyr Met Pro Gln Thr
    530                 535                 540

Trp Thr Ser Asp Asn Thr Asp Ala Val Ser Arg Leu Lys Ile Gln Tyr
545                 550                 555                 560

Gly Thr Ser Leu Ala Tyr Pro Ile Ser Ser Met Gly Ser His Val Ser
                565                 570                 575

Ala Val Pro Asn His Gln Leu His Arg Ser Thr Pro Ile Glu Thr Arg
            580                 585                 590

Gly Asp Val Ala Met Ser Gly Asn Leu Gly Tyr Glu Leu Asp Leu Thr
        595                 600                 605

Lys Leu Ser Asp Gln Glu Lys Glu Ala Val Lys Ala Gln Ile Ser Phe
    610                 615                 620

Tyr Lys Asp Ile Arg Glu Val Ile Gln Phe Gly Lys Phe Tyr Arg Ile
625                 630                 635                 640

Leu Ser Pro Phe Glu Gly Asn Glu Ala Gly Trp Val Phe Val Ser His
                645                 650                 655
```

-continued

Asp Gln Ser Glu Cys Val Ala Gly Tyr Phe Arg Val Leu Ala Glu Pro
            660                 665                 670

Tyr Glu Pro Thr Lys Ile Leu Lys Ile Lys Gly Leu Asn Pro Glu Leu
            675                 680                 685

Asn Tyr Arg Leu Ala Gly Thr Glu Gln Val Phe Gly Gly Asp Glu Leu
690                 695                 700

Met Phe Met Gly Leu Asn Ile Pro Asp Leu Lys Gly Asp Phe Arg Ser
705                 710                 715                 720

Val Leu Trp His Phe Lys Ala Gly Ser Ile His
                725                 730

<210> SEQ ID NO 15
<211> LENGTH: 737
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(737)

<400> SEQUENCE: 15

Met Gly Ile Thr Tyr Gln Glu Gly Gln Ile Phe His Leu Gln Gly
1               5                   10                  15

Lys Asp Thr Ser Tyr Val Met Gln Val Leu Lys Asp Gly Tyr Leu Thr
                20                  25                  30

His Leu Tyr Trp Gly Lys Arg Val Arg Gly Tyr Asn Gln Ser Ile Pro
            35                  40                  45

Val Thr Phe Phe Asp Arg Gly Phe Ser Ala Asn Pro Asp Pro Thr Asp
        50                  55                  60

Arg Thr Phe Ser Leu Asp Thr Leu Pro Gln Glu Tyr Pro Ala Tyr Gly
65                  70                  75                  80

Asn Thr Asp Phe Arg Thr Pro Ala Tyr Gln Ile Gln Leu Glu Asn Gly
                85                  90                  95

Ser Thr Ile Ser Asp Leu Arg Tyr Ser Ser His Lys Ile Tyr Lys Gly
            100                 105                 110

Lys Pro Lys Leu Glu Gly Leu Pro Ser Thr Tyr Ala Gly Arg Asp Glu
        115                 120                 125

Glu Ala Glu Thr Leu Glu Ile Ile Leu Glu Asp Asp Thr Ile Gly Leu
130                 135                 140

Lys Val Thr Leu Ile Tyr Thr Val Phe Glu Ala Tyr Asn Ala Leu Thr
145                 150                 155                 160

Arg Ser Val Arg Phe Glu Asn Ser Gly Arg Thr Val Ile Lys Leu Leu
                165                 170                 175

Arg Ala Leu Ser Leu Asn Leu Asp Phe Arg Asp Gln Asp Phe Glu Leu
            180                 185                 190

Ile Thr Leu Tyr Gly Ser His Asn Asn Glu Arg Asn Leu Ala Arg Arg
        195                 200                 205

Pro Val Ala Pro Gly Leu Gln Ala Ile Glu Ser Arg Arg Gly Ala Ser
210                 215                 220

Ser His Gln Gln Asn Pro Phe Leu Ala Leu Val Arg Pro Thr Ser Thr
225                 230                 235                 240

Glu Asp Ser Gly Glu Val Phe Ala Leu Asn Leu Val Tyr Ser Gly Asn
                245                 250                 255

Phe Leu Gly Gln Val Glu Val Asn Gln Phe Lys Thr Thr Arg Leu Ser
            260                 265                 270

-continued

```
Leu Gly Ile Asn Pro Phe Asp Phe Thr Trp Gln Leu Asn Pro Lys Glu
            275                 280                 285

Ala Phe Gln Thr Pro Glu Ala Val Met Val Tyr Ser Ser Asn Gly Leu
290                 295                 300

Asn Glu Met Ser Gln Thr Phe His Asp Leu Tyr Thr Asn Arg Leu Cys
305                 310                 315                 320

Arg Gly Gln Phe Arg Asn Gln Ile Arg Pro Ile Leu Ile Asn Asn Trp
                325                 330                 335

Glu Ala Thr Tyr Phe Asn Phe Asn Ala Glu Lys Val Leu Glu Ile Ala
            340                 345                 350

Lys Val Gly Lys Glu Leu Gly Met Glu Leu Val Val Leu Asp Asp Gly
            355                 360                 365

Trp Phe Gly Glu Arg Asp Asp Cys Arg Ser Leu Gly Asp Trp Val
            370                 375                 380

Val Asp Arg Arg Lys Leu Pro Asp Gly Leu Asp Asn Leu Ala Lys Arg
385                 390                 395                 400

Val Arg Glu Met Gly Leu Glu Phe Gly Leu Trp Phe Glu Pro Glu Met
                405                 410                 415

Val Ser Val Asn Ser Asn Leu Tyr Arg Glu His Pro Asp Trp Cys Leu
            420                 425                 430

His Val Pro Asn Arg Pro Lys Ser Glu Ser Arg Asn Gln Leu Ile Leu
            435                 440                 445

Asp Leu Ser Arg Gln Glu Val Cys Glu Tyr Val Ile Glu Ser Val Ser
            450                 455                 460

Ser Ile Leu Ser Thr Val Pro Ile Ser Tyr Val Lys Trp Asp Met Asn
465                 470                 475                 480

Arg His Met Thr Glu Val Gly Ser Ala Asp Leu Pro Ala Glu Arg Gln
                485                 490                 495

Arg Glu Thr Ala His Arg Tyr Met Leu Gly Leu Tyr Arg Val Leu Glu
            500                 505                 510

Ala Ile Thr Ser Arg Phe Pro Asn Val Leu Phe Glu Ser Cys Ser Gly
            515                 520                 525

Gly Gly Gly Arg Phe Asp Pro Gly Phe Leu Tyr Tyr Met Pro Gln Thr
530                 535                 540

Trp Thr Ser Asp Asn Thr Asp Ala Val Ser Arg Leu Lys Ile Gln Tyr
545                 550                 555                 560

Gly Thr Ser Leu Ala Tyr Pro Ile Ser Ser Met Gly Ser His Val Ser
                565                 570                 575

Ala Val Pro Asn His Gln Leu His Arg Ser Thr Pro Ile Glu Thr Arg
            580                 585                 590

Gly Asp Val Ala Met Ser Gly Asn Leu Gly Tyr Glu Leu Asp Leu Thr
            595                 600                 605

Lys Leu Ser Asp Gln Glu Lys Glu Ala Val Lys Ala Gln Ile Ser Phe
610                 615                 620

Tyr Lys Asp Ile Arg Glu Val Ile Gln Phe Gly Lys Phe Tyr Arg Ile
625                 630                 635                 640

Leu Ser Pro Phe Glu Gly Asn Glu Ala Gly Trp Val Phe Val Ser His
                645                 650                 655

Asp Gln Ser Glu Cys Val Ala Gly Tyr Phe Arg Val Leu Ala Glu Pro
            660                 665                 670

Tyr Glu Pro Thr Lys Ile Leu Lys Ile Lys Gly Leu Asn Pro Glu Leu
            675                 680                 685

Asn Tyr Arg Leu Ala Gly Thr Glu Gln Val Phe Gly Gly Asp Glu Leu
```

```
                  690                 695                 700
Met Phe Met Gly Leu Asn Ile Pro Asp Leu Lys Gly Asp Phe Arg Ser
705                 710                 715                 720

Val Leu Trp His Phe Lys Ala Gly Ser Ile His His His His His His
                    725                 730                 735

His
```

<210> SEQ ID NO 16
<211> LENGTH: 747
<212> TYPE: PRT
<213> ORGANISM: Aspergillus niger

<400> SEQUENCE: 16

```
Met Ile Gly Ser Ser His Ala Val Val Ala Leu Gly Leu Phe Thr Leu
1               5                   10                  15

Tyr Gly His Ser Ala Ala Pro Ala Thr Gly Ala Ser Asn Ser Gln
                20                  25                  30

Thr Ile Val Thr Asn Gly Thr Ser Phe Ala Leu Asn Gly Asp Asn Val
                35                  40                  45

Ser Tyr Arg Phe His Val Asn Ser Thr Thr Gly Asp Leu Ile Ser Asp
50                  55                  60

His Phe Gly Gly Val Val Ser Gly Thr Ile Pro Ser Pro Val Glu Pro
65                  70                  75                  80

Ala Val Asn Gly Trp Val Gly Met Pro Gly Arg Ile Arg Arg Glu Phe
                85                  90                  95

Pro Asp Gln Gly Arg Gly Asp Phe Arg Ile Pro Ala Val Arg Ile Arg
                100                 105                 110

Glu Ser Ala Gly Tyr Thr Val Ser Asp Leu Gln Tyr Val Ser His Glu
                115                 120                 125

Val Ile Glu Gly Lys Asn Ala Leu Pro Gly Leu Pro Ala Thr Phe Gly
130                 135                 140

Asp Ala Gln Ala Val Thr Thr Leu Val Val His Leu Tyr Asp Asn Tyr
145                 150                 155                 160

Ser Ser Val Ala Ala Asp Leu Ser Tyr Ser Ile Phe Pro Lys Tyr Asp
                165                 170                 175

Ala Ile Val Arg Ser Val Asn Val Ile Asn Gln Gly Pro Gly Asn Ile
                180                 185                 190

Thr Ile Glu Ala Leu Ala Ser Ile Ser Ile Asp Phe Pro Tyr Glu Asp
                195                 200                 205

Leu Asp Met Val Ser Leu Arg Gly Asp Trp Ala Arg Glu Ala Asn Val
210                 215                 220

Gln Arg Ser Lys Val Gln Tyr Gly Val Gln Gly Phe Ser Ser Thr
225                 230                 235                 240

Gly Tyr Ser Ser His Leu His Asn Pro Phe Leu Ala Ile Val Asp Pro
                245                 250                 255

Ala Thr Thr Glu Ser Gln Gly Glu Ala Trp Gly Phe Asn Leu Val Tyr
                260                 265                 270

Thr Gly Ser Phe Ser Ala Gln Val Glu Lys Gly Ser Gln Gly Phe Thr
                275                 280                 285

Arg Ala Leu Leu Gly Phe Asn Pro Asp Gln Leu Ser Trp Asn Leu Gly
                290                 295                 300

Pro Gly Glu Thr Leu Thr Ser Pro Glu Cys Val Ala Val Tyr Ser Asp
305                 310                 315                 320

Lys Gly Leu Gly Ser Val Ser Arg Lys Phe His Arg Leu Tyr Arg Asn
```

```
                    325                 330                 335
His Leu Met Lys Ser Lys Phe Ala Thr Ser Asp Arg Pro Val Leu Leu
            340                 345                 350
Asn Ser Trp Glu Gly Val Tyr Phe Asp Tyr Asn Gln Ser Ser Ile Glu
            355                 360                 365
Thr Leu Ala Glu Glu Ser Ala Ala Leu Gly Val His Leu Phe Val Met
            370                 375                 380
Asp Asp Gly Trp Phe Gly Asp Lys Tyr Pro Arg Val Ser Asp Asn Ala
385                 390                 395                 400
Gly Leu Gly Asp Trp Met Pro Asn Pro Ala Arg Phe Pro Asp Gly Leu
            405                 410                 415
Thr Pro Val Val Gln Asp Ile Thr Asn Leu Thr Val Asn Gly Thr Glu
            420                 425                 430
Ser Thr Lys Leu Arg Phe Gly Ile Trp Val Glu Pro Glu Met Val Asn
            435                 440                 445
Pro Asn Ser Thr Leu Tyr His Glu His Pro Glu Trp Ala Leu His Ala
            450                 455                 460
Gly Pro Tyr Pro Arg Thr Glu Arg Asn Gln Leu Val Leu Asn Leu
465                 470                 475                 480
Ala Leu Pro Ala Val Gln Asp Phe Ile Ile Asp Phe Met Thr Asn Leu
            485                 490                 495
Leu Gln Asp Thr Gly Ile Ser Tyr Val Lys Trp Asp Asn Asn Arg Gly
            500                 505                 510
Ile His Glu Thr Pro Ser Pro Ser Thr Asp His Gln Tyr Met Leu Gly
            515                 520                 525
Leu Tyr Arg Val Phe Asp Thr Leu Thr Thr Arg Phe Pro Asp Val Leu
            530                 535                 540
Trp Glu Gly Cys Ala Ser Gly Gly Gly Arg Phe Asp Ala Gly Met Leu
545                 550                 555                 560
Gln Tyr Val Pro Gln Ile Trp Thr Ser Asp Asn Thr Asp Ala Ile Asp
            565                 570                 575
Arg Ile Thr Ile Gln Phe Gly Thr Ser Leu Ala Tyr Pro Pro Ser Ala
            580                 585                 590
Met Gly Ala His Leu Ser Ala Val Pro Asn Ala Gln Thr Gly Arg Thr
            595                 600                 605
Val Pro Ile Thr Phe Arg Ala His Val Ala Met Met Gly Gly Ser Phe
            610                 615                 620
Gly Leu Glu Leu Asp Pro Ala Thr Val Glu Gly Asp Glu Ile Val Pro
625                 630                 635                 640
Glu Leu Leu Ala Leu Ala Glu Lys Val Asn Pro Ile Ile Leu Asn Gly
            645                 650                 655
Asp Leu Tyr Arg Leu Arg Leu Pro Gln Asp Ser Gln Trp Pro Ala Ala
            660                 665                 670
Leu Phe Val Thr Gln Asp Gly Ala Gln Ala Val Leu Phe Tyr Phe Gln
            675                 680                 685
Val Gln Pro Asn Val Asn His Ala Val Pro Trp Val Arg Leu Gln Gly
            690                 695                 700
Leu Asp Pro Lys Ala Asp Tyr Thr Val Asp Gly Asp Gln Thr Tyr Ser
705                 710                 715                 720
Gly Ala Thr Leu Met Asn Leu Gly Leu Gln Tyr Ser Phe Asp Thr Glu
            725                 730                 735
Tyr Gly Ser Lys Val Val Phe Leu Glu Arg Gln
            740                 745
```

-continued

```
<210> SEQ ID NO 17
<211> LENGTH: 2442
<212> TYPE: DNA
<213> ORGANISM: Aspergillus puniceus
<220> FEATURE:
<221> NAME/KEY: CDS
<222> LOCATION: (1)..(109)
<220> FEATURE:
<221> NAME/KEY: sig_peptide
<222> LOCATION: (1)..(87)
<220> FEATURE:
<221> NAME/KEY: mat_peptide
<222> LOCATION: (88)..(2439)
<220> FEATURE:
<221> NAME/KEY: CDS
<222> LOCATION: (173)..(779)
<220> FEATURE:
<221> NAME/KEY: CDS
<222> LOCATION: (864)..(2439)

<400> SEQUENCE: 17 atg ttt ggg tct tct acc tcg acc atc gct gct gcg gct gtg acg ggc         48
Met Phe Gly Ser Ser Thr Ser Thr Ile Ala Ala Ala Ala Val Thr Gly
            -25                 -20                 -15 ctc ttg aca gtc tgc agt caa tcc ccc ttg gtt ctg gct cag gag tcg         96
Leu Leu Thr Val Cys Ser Gln Ser Pro Leu Val Leu Ala Gln Glu Ser
        -10                  -5              -1  1 agc agt cag gat g gttcgtctcc ctttcatccc ctcgaattac tactaccccc          149
Ser Ser Gln Asp
   5 ccgagattcc taacgctatc cag ca  atc gtc gcc tct ggt aca acg ttc tcc       201
                              Ala Ile Val Ala Ser Gly Thr Thr Phe Ser
                                           10                  15 cta aat ggc gac aac gtc tcg tac aac ttc cac gtc gac aac agc act         249
Leu Asn Gly Asp Asn Val Ser Tyr Asn Phe His Val Asp Asn Ser Thr
         20                  25                  30 ggc gac ctc ata acc gac cac ttt ggc agc ccc gta tcc ggc gcg cta         297
Gly Asp Leu Ile Thr Asp His Phe Gly Ser Pro Val Ser Gly Ala Leu
     35                  40                  45 ccc agc cca gtc gag cca gcc ata aac ggc tgg gtc gga ctc ccc ggc         345
Pro Ser Pro Val Glu Pro Ala Ile Asn Gly Trp Val Gly Leu Pro Gly
 50                  55                  60                  65 cgc gtg cgc cgc gag ttc ccg gac aca ggc cgc ggc gac ttt cgc atc         393
Arg Val Arg Arg Glu Phe Pro Asp Thr Gly Arg Gly Asp Phe Arg Ile
             70                  75                  80 ccc gcg atc cgc atc cgt caa acc gca ggg tac gag gtt agc gat ctg         441
Pro Ala Ile Arg Ile Arg Gln Thr Ala Gly Tyr Glu Val Ser Asp Leu
         85                  90                  95 cag tac cag tcg cac gag att gtg cag ggg aaa cct gcc ttg ccg ggg         489
Gln Tyr Gln Ser His Glu Ile Val Gln Gly Lys Pro Ala Leu Pro Gly
     100                 105                 110 ctg ccc tcc acg ttc ggt gat gca ggg gat gtg agt act ttg att gtg         537
Leu Pro Ser Thr Phe Gly Asp Ala Gly Asp Val Ser Thr Leu Ile Val
 115                 120                 125 cac ctg tac gac aat tac agt tcc gtt gcg gcg gat ctg gtg tat tcg         585
His Leu Tyr Asp Asn Tyr Ser Ser Val Ala Ala Asp Leu Val Tyr Ser
130                 135                 140                 145 gtg ttt cca aag tat gat gcc atc gtg cgg agt gtg aat gtt acg aat         633
Val Phe Pro Lys Tyr Asp Ala Ile Val Arg Ser Val Asn Val Thr Asn
                150                 155                 160 cgg ggc gag ggc aac gtg agt atc gag gcg ctg gcg agc ttt agt gtg         681
Arg Gly Glu Gly Asn Val Ser Ile Glu Ala Leu Ala Ser Phe Ser Val
            165                 170                 175
```

```
gat ttt ccg gat gag gag ctg gag atg gtg agc ttg agg ggg gac tgg      729
Asp Phe Pro Asp Glu Glu Leu Glu Met Val Ser Leu Arg Gly Asp Trp
        180                 185                 190 gcg cgc gag gcg aat agg cag cgg agg aag gtt gag tat ggg gtt cag      777
Ala Arg Glu Ala Asn Arg Gln Arg Arg Lys Val Glu Tyr Gly Val Gln
    195                 200                 205 gg gtgagtactc gcataccggt tttctcaatg ttgaggcggt ttccatgggt            829
Gly
210 tgattggctt ggaggtatgc tgatgagggt gcag g ttt gga agt acg act ggt      882
                                       Phe Gly Ser Thr Thr Gly
                                                       215 tac tcg tcg cat ttg cat aat ccc ttc ctt gcg ctc gtg cat ccg tct      930
Tyr Ser Ser His Leu His Asn Pro Phe Leu Ala Leu Val His Pro Ser
                220                 225                 230 act acc gaa tct caa ggc gag acc tgg gga ttc tcg ctg gtc tac acg      978
Thr Thr Glu Ser Gln Gly Glu Thr Trp Gly Phe Ser Leu Val Tyr Thr
            235                 240                 245 ggg tct ttc tcg gtg gaa gta gag aag gga tcg caa ggc ttg acg cga     1026
Gly Ser Phe Ser Val Glu Val Glu Lys Gly Ser Gln Gly Leu Thr Arg
        250                 255                 260 gcc ctg ctt gga ctc aac ccc aac caa ctc tca tgg aac ctt ggc ccc     1074
Ala Leu Leu Gly Leu Asn Pro Asn Gln Leu Ser Trp Asn Leu Gly Pro
265                 270                 275                 280 ggc gag aca ctc acc tcc ccc gag tgt gtt tca gtc tac tcg aaa gac     1122
Gly Glu Thr Leu Thr Ser Pro Glu Cys Val Ser Val Tyr Ser Lys Asp
                285                 290                 295 gga atc ggc ggc atg tct cgt tcg ttc cac cgt cta tat cgc aac cac     1170
Gly Ile Gly Gly Met Ser Arg Ser Phe His Arg Leu Tyr Arg Asn His
            300                 305                 310 ttg atc aag agc caa ttc gcc acc tcc gat agg ccg gcc ctg ctc aac     1218
Leu Ile Lys Ser Gln Phe Ala Thr Ser Asp Arg Pro Ala Leu Leu Asn
        315                 320                 325 agt tgg gaa ggc gtc tac ttt gac ttt aat cag agc aca atc tac aac     1266
Ser Trp Glu Gly Val Tyr Phe Asp Phe Asn Gln Ser Thr Ile Tyr Asn
330                 335                 340 ctc gcc gag gaa gcc gct tcc ctg ggc atc cac ctc ttc gtc atg gat     1314
Leu Ala Glu Glu Ala Ala Ser Leu Gly Ile His Leu Phe Val Met Asp
345                 350                 355                 360 gac ggc tgg ttc ggc gac gaa tac ccg cga gta tca gac gaa gcg ggt     1362
Asp Gly Trp Phe Gly Asp Glu Tyr Pro Arg Val Ser Asp Glu Ala Gly
                365                 370                 375 cta ggc gac tgg acg ccg aat ccc gaa cgg ttc ccc aac ggc tta tcg     1410
Leu Gly Asp Trp Thr Pro Asn Pro Glu Arg Phe Pro Asn Gly Leu Ser
            380                 385                 390 ccc ctc gtc gag ggg gtg aca aac ctc aca gcc aac gac agt agc aac     1458
Pro Leu Val Glu Gly Val Thr Asn Leu Thr Ala Asn Asp Ser Ser Asn
        395                 400                 405 agt agc agt agc agc aat agc agc aca aag ctc cgc ttc ggc atc tgg     1506
Ser Ser Ser Ser Ser Asn Ser Ser Thr Lys Leu Arg Phe Gly Ile Trp
410                 415                 420 gtt gag ccc gaa atg gtc aac ccc aac tcg acc ctc tac cac gaa cac     1554
Val Glu Pro Glu Met Val Asn Pro Asn Ser Thr Leu Tyr His Glu His
425                 430                 435                 440 cca gac tgg gcc ctg cac gca gga ccc tac cca cgc acc gaa cgc cgc     1602
Pro Asp Trp Ala Leu His Ala Gly Pro Tyr Pro Arg Thr Glu Arg Arg
                445                 450                 455 aac caa ctc gtg cta aac ctc gcc ctc ccc gaa gtc cag gaa tac atc     1650
Asn Gln Leu Val Leu Asn Leu Ala Leu Pro Glu Val Gln Glu Tyr Ile
```

```
                     460                 465                 470
atc gac ttc atg acc acc ctg ctc aac tcc gca gac atc acg tac atc      1698
Ile Asp Phe Met Thr Thr Leu Leu Asn Ser Ala Asp Ile Thr Tyr Ile
                475                 480                 485 aaa tgg gac aac aac cgc ggc atg cac gag acc ccc tcc ccc tca aac      1746
Lys Trp Asp Asn Asn Arg Gly Met His Glu Thr Pro Ser Pro Ser Asn
            490                 495                 500 gac cac gcc tac atg ctc ggc ctc tac cac gtc ttc agc acc ctc aca      1794
Asp His Ala Tyr Met Leu Gly Leu Tyr His Val Phe Ser Thr Leu Thr
505                 510                 515                 520 acc cgc ttc ccc gac gtc ctc tgg gaa ggc tgc gcc tcc ggc ggc ggc      1842
Thr Arg Phe Pro Asp Val Leu Trp Glu Gly Cys Ala Ser Gly Gly Gly
                525                 530                 535 cgc ttc gac gca ggc gtg ctg cac tac ttc ccg cag atc tgg acc tcc      1890
Arg Phe Asp Ala Gly Val Leu His Tyr Phe Pro Gln Ile Trp Thr Ser
            540                 545                 550 gac aac acc gac ggc gtc gac cgc gtg aca atc caa ttc ggc acc tcg      1938
Asp Asn Thr Asp Gly Val Asp Arg Val Thr Ile Gln Phe Gly Thr Ser
        555                 560                 565 ctc gcc tac ccg ccc agc gca atg ggc gca cat cta tcc gcc gtc ccc      1986
Leu Ala Tyr Pro Pro Ser Ala Met Gly Ala His Leu Ser Ala Val Pro
570                 575                 580 aac cac caa acg ggc cgc acc gtg ccc ctc acc ctc cgc gcc cac gtc      2034
Asn His Gln Thr Gly Arg Thr Val Pro Leu Thr Leu Arg Ala His Val
585                 590                 595                 600 gcc atg atg ggc ggc tcg ttc ggc ctc gaa ctc gac ccg agc gaa ctc      2082
Ala Met Met Gly Gly Ser Phe Gly Leu Glu Leu Asp Pro Ser Glu Leu
                605                 610                 615 tcc gag gca gag aag gaa tcc gtc tca gac ctc ctc gct ctc gcg gaa      2130
Ser Glu Ala Glu Lys Glu Ser Val Ser Asp Leu Leu Ala Leu Ala Glu
            620                 625                 630 cgc atc aac ccg atc atc cta acg ggc gac ctg tac cgc cta cgg ctc      2178
Arg Ile Asn Pro Ile Ile Leu Thr Gly Asp Leu Tyr Arg Leu Arg Leu
        635                 640                 645 ccc gag gac tcg aaa tgg ccc gcc gcg cag ttc atc tcg caa ggt ggg      2226
Pro Glu Asp Ser Lys Trp Pro Ala Ala Gln Phe Ile Ser Gln Gly Gly
650                 655                 660 ggc gac caa gtc gtg ctg ttt gtc ttc cag ctc gcg ccg aac gtc aac      2274
Gly Asp Gln Val Val Leu Phe Val Phe Gln Leu Ala Pro Asn Val Asn
665                 670                 675                 680 cat gcc gtt ccc tgg atc cgc ttg caa ggg ctg gat gcg cag gcg cgg      2322
His Ala Val Pro Trp Ile Arg Leu Gln Gly Leu Asp Ala Gln Ala Arg
                685                 690                 695 tat gtc gtt gat ggg cgc gcg aac gag acg tac tca ggc gcc gcg ctg      2370
Tyr Val Val Asp Gly Arg Ala Asn Glu Thr Tyr Ser Gly Ala Ala Leu
            700                 705                 710 atg aat cgg gga ctg cag ttt gcg ttt gag acg gag tat ggg agt cgc      2418
Met Asn Arg Gly Leu Gln Phe Ala Phe Glu Thr Glu Tyr Gly Ser Arg
        715                 720                 725 gtt gtg ctt ctg gag aag gag tag                                      2442
Val Val Leu Leu Glu Lys Glu
730                 735

<210> SEQ ID NO 18
<211> LENGTH: 764
<212> TYPE: PRT
<213> ORGANISM: Aspergillus puniceus

<400> SEQUENCE: 18

Met Phe Gly Ser Ser Thr Ser Thr Ile Ala Ala Ala Ala Val Thr Gly
```

-continued

```
                -25                 -20                 -15
Leu Leu Thr Val Cys Ser Gln Ser Pro Leu Val Leu Ala Gln Glu Ser
                -10                 -5                  -1  1

Ser Ser Gln Asp Ala Ile Val Ala Ser Gly Thr Thr Phe Ser Leu Asn
    5                   10                  15

Gly Asp Asn Val Ser Tyr Asn Phe His Val Asp Asn Ser Thr Gly Asp
20                  25                  30                  35

Leu Ile Thr Asp His Phe Gly Ser Pro Val Ser Gly Ala Leu Pro Ser
                40                  45                  50

Pro Val Glu Pro Ala Ile Asn Gly Trp Val Gly Leu Pro Gly Arg Val
            55                  60                  65

Arg Arg Glu Phe Pro Asp Thr Gly Arg Gly Asp Phe Arg Ile Pro Ala
        70                  75                  80

Ile Arg Ile Arg Gln Thr Ala Gly Tyr Glu Val Ser Asp Leu Gln Tyr
    85                  90                  95

Gln Ser His Glu Ile Val Gln Gly Lys Pro Ala Leu Pro Gly Leu Pro
100                 105                 110                 115

Ser Thr Phe Gly Asp Ala Gly Asp Val Ser Thr Leu Ile Val His Leu
            120                 125                 130

Tyr Asp Asn Tyr Ser Ser Val Ala Ala Asp Leu Val Tyr Ser Val Phe
            135                 140                 145

Pro Lys Tyr Asp Ala Ile Val Arg Ser Val Asn Val Thr Asn Arg Gly
        150                 155                 160

Glu Gly Asn Val Ser Ile Glu Ala Leu Ala Ser Phe Ser Val Asp Phe
    165                 170                 175

Pro Asp Glu Glu Leu Glu Met Val Ser Leu Arg Gly Asp Trp Ala Arg
180                 185                 190                 195

Glu Ala Asn Arg Gln Arg Arg Lys Val Glu Tyr Gly Val Gln Gly Phe
            200                 205                 210

Gly Ser Thr Thr Gly Tyr Ser Ser His Leu His Asn Pro Phe Leu Ala
        215                 220                 225

Leu Val His Pro Ser Thr Thr Glu Ser Gln Gly Glu Thr Trp Gly Phe
    230                 235                 240

Ser Leu Val Tyr Thr Gly Ser Phe Ser Val Glu Val Glu Lys Gly Ser
    245                 250                 255

Gln Gly Leu Thr Arg Ala Leu Leu Gly Leu Asn Pro Asn Gln Leu Ser
260                 265                 270                 275

Trp Asn Leu Gly Pro Gly Glu Thr Leu Thr Ser Pro Glu Cys Val Ser
            280                 285                 290

Val Tyr Ser Lys Asp Gly Ile Gly Gly Met Ser Arg Ser Phe His Arg
        295                 300                 305

Leu Tyr Arg Asn His Leu Ile Lys Ser Gln Phe Ala Thr Ser Asp Arg
    310                 315                 320

Pro Ala Leu Leu Asn Ser Trp Glu Gly Val Tyr Phe Asp Phe Asn Gln
325                 330                 335

Ser Thr Ile Tyr Asn Leu Ala Glu Glu Ala Ala Ser Leu Gly Ile His
340                 345                 350                 355

Leu Phe Val Met Asp Asp Gly Trp Phe Gly Asp Glu Tyr Pro Arg Val
            360                 365                 370

Ser Asp Glu Ala Gly Leu Gly Asp Trp Thr Pro Asn Pro Glu Arg Phe
            375                 380                 385

Pro Asn Gly Leu Ser Pro Leu Val Glu Gly Val Thr Asn Leu Thr Ala
        390                 395                 400
```

```
Asn Asp Ser Ser Asn Ser Ser Ser Ser Asn Ser Ser Thr Lys Leu
    405                 410                 415

Arg Phe Gly Ile Trp Val Glu Pro Glu Met Val Asn Pro Asn Ser Thr
420                 425                 430                 435

Leu Tyr His Glu His Pro Asp Trp Ala Leu His Ala Gly Pro Tyr Pro
                440                 445                 450

Arg Thr Glu Arg Arg Asn Gln Leu Val Leu Asn Leu Ala Leu Pro Glu
            455                 460                 465

Val Gln Glu Tyr Ile Ile Asp Phe Met Thr Thr Leu Leu Asn Ser Ala
        470                 475                 480

Asp Ile Thr Tyr Ile Lys Trp Asp Asn Asn Arg Gly Met His Glu Thr
485                 490                 495

Pro Ser Pro Ser Asn Asp His Ala Tyr Met Leu Gly Leu Tyr His Val
500                 505                 510                 515

Phe Ser Thr Leu Thr Thr Arg Phe Pro Asp Val Leu Trp Glu Gly Cys
                520                 525                 530

Ala Ser Gly Gly Gly Arg Phe Asp Ala Gly Val Leu His Tyr Phe Pro
            535                 540                 545

Gln Ile Trp Thr Ser Asp Asn Thr Asp Gly Val Asp Arg Val Thr Ile
        550                 555                 560

Gln Phe Gly Thr Ser Leu Ala Tyr Pro Pro Ser Ala Met Gly Ala His
565                 570                 575

Leu Ser Ala Val Pro Asn His Gln Thr Gly Arg Thr Val Pro Leu Thr
580                 585                 590                 595

Leu Arg Ala His Val Ala Met Met Gly Gly Ser Phe Gly Leu Glu Leu
                600                 605                 610

Asp Pro Ser Glu Leu Ser Glu Ala Glu Lys Glu Ser Val Ser Asp Leu
            615                 620                 625

Leu Ala Leu Ala Glu Arg Ile Asn Pro Ile Ile Leu Thr Gly Asp Leu
        630                 635                 640

Tyr Arg Leu Arg Leu Pro Glu Asp Ser Lys Trp Pro Ala Ala Gln Phe
645                 650                 655

Ile Ser Gln Gly Gly Asp Gln Val Val Leu Phe Val Phe Gln Leu
660                 665                 670                 675

Ala Pro Asn Val Asn His Ala Val Pro Trp Ile Arg Leu Gln Gly Leu
                680                 685                 690

Asp Ala Gln Ala Arg Tyr Val Val Asp Gly Arg Ala Asn Glu Thr Tyr
            695                 700                 705

Ser Gly Ala Ala Leu Met Asn Arg Gly Leu Gln Phe Ala Phe Glu Thr
        710                 715                 720

Glu Tyr Gly Ser Arg Val Val Leu Leu Glu Lys Glu
725                 730                 735
```

<210> SEQ ID NO 19
<211> LENGTH: 735
<212> TYPE: PRT
<213> ORGANISM: Aspergillus puniceus
<220> FEATURE:
<221> NAME/KEY: mat_peptide
<222> LOCATION: (1)..(735)

<400> SEQUENCE: 19

```
Gln Glu Ser Ser Ser Gln Asp Ala Ile Val Ala Ser Gly Thr Thr Phe
1               5                   10                  15

Ser Leu Asn Gly Asp Asn Val Ser Tyr Asn Phe His Val Asp Asn Ser
```

```
                20                  25                  30
Thr Gly Asp Leu Ile Thr Asp His Phe Gly Ser Pro Val Ser Gly Ala
                35                  40                  45
Leu Pro Ser Pro Val Glu Pro Ala Ile Asn Gly Trp Val Gly Leu Pro
            50                  55                  60
Gly Arg Val Arg Arg Glu Phe Pro Asp Thr Arg Gly Asp Phe Arg
65                  70                  75                  80
Ile Pro Ala Ile Arg Ile Arg Gln Thr Ala Gly Tyr Glu Val Ser Asp
                85                  90                  95
Leu Gln Tyr Gln Ser His Glu Ile Val Gln Gly Lys Pro Ala Leu Pro
                100                 105                 110
Gly Leu Pro Ser Thr Phe Gly Asp Ala Gly Asp Val Ser Thr Leu Ile
                115                 120                 125
Val His Leu Tyr Asp Asn Tyr Ser Ser Val Ala Ala Asp Leu Val Tyr
                130                 135                 140
Ser Val Phe Pro Lys Tyr Asp Ala Ile Val Arg Ser Val Asn Val Thr
145                 150                 155                 160
Asn Arg Gly Glu Gly Asn Val Ser Ile Glu Ala Leu Ala Ser Phe Ser
                165                 170                 175
Val Asp Phe Pro Asp Glu Glu Leu Glu Met Val Ser Leu Arg Gly Asp
                180                 185                 190
Trp Ala Arg Glu Ala Asn Arg Gln Arg Arg Lys Val Glu Tyr Gly Val
                195                 200                 205
Gln Gly Phe Gly Ser Thr Thr Gly Tyr Ser Ser His Leu His Asn Pro
                210                 215                 220
Phe Leu Ala Leu Val His Pro Ser Thr Thr Glu Ser Gln Gly Glu Thr
225                 230                 235                 240
Trp Gly Phe Ser Leu Val Tyr Thr Gly Ser Phe Ser Val Glu Val Glu
                245                 250                 255
Lys Gly Ser Gln Gly Leu Thr Arg Ala Leu Leu Gly Leu Asn Pro Asn
                260                 265                 270
Gln Leu Ser Trp Asn Leu Gly Pro Gly Glu Thr Leu Thr Ser Pro Glu
                275                 280                 285
Cys Val Ser Val Tyr Ser Lys Asp Gly Ile Gly Gly Met Ser Arg Ser
                290                 295                 300
Phe His Arg Leu Tyr Arg Asn His Leu Ile Lys Ser Gln Phe Ala Thr
305                 310                 315                 320
Ser Asp Arg Pro Ala Leu Leu Asn Ser Trp Glu Gly Val Tyr Phe Asp
                325                 330                 335
Phe Asn Gln Ser Thr Ile Tyr Asn Leu Ala Glu Glu Ala Ala Ser Leu
                340                 345                 350
Gly Ile His Leu Phe Val Met Asp Asp Gly Trp Phe Gly Asp Glu Tyr
                355                 360                 365
Pro Arg Val Ser Asp Glu Ala Gly Leu Gly Asp Trp Thr Pro Asn Pro
                370                 375                 380
Glu Arg Phe Pro Asn Gly Leu Ser Pro Leu Val Gly Val Thr Asn
385                 390                 395                 400
Leu Thr Ala Asn Asp Ser Ser Asn Ser Ser Ser Ser Asn Ser Ser
                405                 410                 415
Thr Lys Leu Arg Phe Gly Ile Trp Val Glu Pro Glu Met Val Asn Pro
                420                 425                 430
Asn Ser Thr Leu Tyr His Glu His Pro Asp Trp Ala Leu His Ala Gly
                435                 440                 445
```

```
Pro Tyr Pro Arg Thr Glu Arg Arg Asn Gln Leu Val Leu Asn Leu Ala
    450                 455                 460

Leu Pro Glu Val Gln Glu Tyr Ile Ile Asp Phe Met Thr Thr Leu Leu
465                 470                 475                 480

Asn Ser Ala Asp Ile Thr Tyr Ile Lys Trp Asp Asn Asn Arg Gly Met
                485                 490                 495

His Glu Thr Pro Ser Pro Ser Asn Asp His Ala Tyr Met Leu Gly Leu
            500                 505                 510

Tyr His Val Phe Ser Thr Leu Thr Thr Arg Phe Pro Asp Val Leu Trp
        515                 520                 525

Glu Gly Cys Ala Ser Gly Gly Gly Arg Phe Asp Ala Gly Val Leu His
    530                 535                 540

Tyr Phe Pro Gln Ile Trp Thr Ser Asp Asn Thr Asp Gly Val Asp Arg
545                 550                 555                 560

Val Thr Ile Gln Phe Gly Thr Ser Leu Ala Tyr Pro Pro Ser Ala Met
                565                 570                 575

Gly Ala His Leu Ser Ala Val Pro Asn His Gln Thr Gly Arg Thr Val
            580                 585                 590

Pro Leu Thr Leu Arg Ala His Val Ala Met Met Gly Gly Ser Phe Gly
        595                 600                 605

Leu Glu Leu Asp Pro Ser Glu Leu Ser Glu Ala Glu Lys Glu Ser Val
    610                 615                 620

Ser Asp Leu Leu Ala Leu Ala Glu Arg Ile Asn Pro Ile Ile Leu Thr
625                 630                 635                 640

Gly Asp Leu Tyr Arg Leu Arg Leu Pro Glu Asp Ser Lys Trp Pro Ala
                645                 650                 655

Ala Gln Phe Ile Ser Gln Gly Gly Asp Gln Val Val Leu Phe Val
            660                 665                 670

Phe Gln Leu Ala Pro Asn Val Asn His Ala Val Pro Trp Ile Arg Leu
        675                 680                 685

Gln Gly Leu Asp Ala Gln Ala Arg Tyr Val Val Asp Gly Arg Ala Asn
    690                 695                 700

Glu Thr Tyr Ser Gly Ala Ala Leu Met Asn Arg Gly Leu Gln Phe Ala
705                 710                 715                 720

Phe Glu Thr Glu Tyr Gly Ser Arg Val Val Leu Leu Lys Glu
                725                 730                 735

<210> SEQ ID NO 20
<211> LENGTH: 729
<212> TYPE: PRT
<213> ORGANISM: Parageobacillus thermoglucosidans

<400> SEQUENCE: 20

Met Ala Ile Val Phe Asp Pro Thr Asn Lys Thr Phe His Leu Gln Ala
1               5                   10                  15

Asn Asp Thr Ser Tyr Val Met Gln Leu Val Arg Ser Gly Tyr Leu Ser
                20                  25                  30

His Leu Tyr Trp Gly Lys Lys Ile Arg Ser Ala Asn Gly Ser Arg Arg
            35                  40                  45

Phe Gln Phe Phe Asp Arg Pro Phe Ser Pro Asn Pro Asp Pro Ser Asp
        50                  55                  60

Arg Thr Phe Ser Leu Asp Thr Leu Pro Gln Glu Tyr Pro Ala Tyr Gly
65                  70                  75                  80

Asn Thr Asp Phe Arg Ala Pro Ala Tyr Gln Val Gln Leu Glu Asn Gly
```

-continued

```
                85                  90                  95
Ala Thr Ile Ser Asp Leu Arg Tyr Lys Thr His Arg Ile Tyr Lys Gly
            100                 105                 110
Lys Pro Lys Leu Lys Gly Leu Pro Ala Thr Tyr Val Glu Arg Glu Asn
            115                 120                 125
Glu Ala Glu Thr Leu Glu Ile Val Leu Glu Asp Arg Val Ile Gly Leu
130                 135                 140
His Val Thr Leu Leu Tyr Thr Val Tyr Glu Arg Trp Asn Val Val Thr
145                 150                 155                 160
Arg Ser Ala Arg Phe Glu Asn Arg Gly Ala Glu Arg Ile Lys Leu Leu
                165                 170                 175
Arg Ala Leu Ser Met Asn Val Asp Phe Pro His Ala Asp Tyr Glu Trp
            180                 185                 190
Leu His Leu Pro Gly Ala Trp Gly Arg Glu Arg Ala Val Glu Arg Arg
            195                 200                 205
Pro Leu Val Thr Gly Ile Gln Ser Val Glu Ser Arg Arg Gly Ala Ser
            210                 215                 220
Ser His Gln Gln Asn Pro Phe Ile Ala Leu Leu Gly Lys Asn Thr Asn
225                 230                 235                 240
Glu Asp Val Gly Glu Val Tyr Gly Phe Ser Leu Val Tyr Ser Gly Asn
                245                 250                 255
Phe Leu Ala Gln Val Glu Val Asp Gln Phe Gln Thr Thr Arg Val Ser
            260                 265                 270
Met Gly Ile Asn Pro Phe Asp Phe Thr Trp Leu Leu Glu Pro Gly Glu
            275                 280                 285
Ser Phe Gln Thr Pro Glu Val Val Met Val Tyr Ser Asp Lys Gly Leu
            290                 295                 300
Asn Gly Met Ser Gln Thr Tyr His Gln Leu Tyr Arg Thr Arg Leu Ala
305                 310                 315                 320
Arg Gly Ala Phe Arg Asp Arg Glu Arg Pro Ile Leu Ile Asn Asn Trp
                325                 330                 335
Glu Ala Thr Tyr Phe His Phe Asn Glu Glu Lys Ile Leu Arg Leu Ala
            340                 345                 350
Lys Thr Ala Ala Glu Leu Gly Ile Glu Leu Phe Val Leu Asp Asp Gly
            355                 360                 365
Trp Phe Gly Lys Arg Asp Asp Asp His Ser Ser Leu Gly Asp Trp Phe
            370                 375                 380
Val Asn Lys Gln Lys Leu Pro Asn Gly Leu Gly Gly Leu Ala Lys Asn
385                 390                 395                 400
Ile Asn Gln Met Gly Met Lys Phe Gly Leu Trp Val Glu Pro Glu Met
                405                 410                 415
Val Ser Val Asp Ser Glu Leu Tyr Arg Gln His Pro Asp Trp Cys Leu
            420                 425                 430
His Val Pro Asn Arg Pro Arg Ser Glu Gly Arg Asn Gln Leu Val Leu
            435                 440                 445
Asp Tyr Ser Arg Lys Glu Val Cys Asp Tyr Ile Ile Gln Val Ile Ser
            450                 455                 460
Asp Val Leu Ala Ser Ala Pro Ile Ser Tyr Val Lys Trp Asp Met Asn
465                 470                 475                 480
Arg His Met Thr Glu Ile Gly Ser Ala Ala Leu Pro Pro Glu Arg Gln
                485                 490                 495
Arg Glu Thr Ala His Arg Tyr Met Leu Gly Leu Tyr Arg Val Met Glu
            500                 505                 510
```

```
Glu Ile Thr Ser Arg Phe Pro His Val Leu Phe Glu Ser Cys Ser Gly
        515                 520                 525

Gly Gly Gly Arg Phe Asp Pro Gly Met Leu Tyr Tyr Met Pro Gln Thr
        530                 535                 540

Trp Thr Ser Asp Asn Thr Asp Ala Val Ser Arg Leu Lys Ile Gln Tyr
545                 550                 555                 560

Gly Thr Ser Leu Val Tyr Pro Ile Ile Ser Met Gly Ala His Val Ser
                565                 570                 575

Ala Val Pro Asn His Gln Val His Arg Ile Thr Ser Leu Glu Met Arg
            580                 585                 590

Gly His Val Ala Met Ser Gly Asn Phe Gly Tyr Glu Leu Asp Leu Thr
        595                 600                 605

Lys Leu Ser Glu Lys Glu Lys Gln Lys Val Lys Glu Gln Val Ala Phe
        610                 615                 620

Tyr Lys Glu Ile Arg Arg Leu Val Gln Phe Gly Thr Phe Tyr Arg Ile
625                 630                 635                 640

Leu Ser Pro Phe Glu Gly Asn Glu Ala Ala Trp Met Phe Val Ser Glu
                645                 650                 655

Asp Arg Ser Glu Ala Leu Val Ala Tyr Phe Arg Val Leu Ala Glu Ala
            660                 665                 670

Asn Ala Pro Leu Ser Phe Ile Arg Leu Lys Gly Leu Asp Pro Lys Lys
        675                 680                 685

Asp Tyr Lys Leu Val Gly Ser Gly Glu Ile Tyr Gly Gly Asp Glu Leu
        690                 695                 700

Met His Ile Gly Leu Ile Val Pro Gln Arg Arg Gly Asp Phe Val Ser
705                 710                 715                 720

Ile Ile Trp Arg Leu Lys Ala Ala Arg
                725
```